US009968652B2

(12) United States Patent
Deisseroth et al.

(10) Patent No.: US 9,968,652 B2
(45) Date of Patent: May 15, 2018

(54) OPTICALLY-CONTROLLED CNS DYSFUNCTION

(71) Applicant: The Board of Trustees of the Leland Stanford Junior University, Standford, CA (US)

(72) Inventors: Karl Deisseroth, Stanford, CA (US); Kay Tye, Cambridge, MA (US); Lief Fenno, San Francisco, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days. days.

(21) Appl. No.: 15/194,379

(22) Filed: Jun. 27, 2016

(65) Prior Publication Data

US 2016/0303192 A1    Oct. 20, 2016

Related U.S. Application Data

(62) Division of application No. 14/555,048, filed on Nov. 26, 2014, now Pat. No. 9,421,258, which is a division of application No. 13/882,719, filed as application No. PCT/US2011/059298 on Nov. 4, 2011, now Pat. No. 8,932,562.

(60) Provisional application No. 61/464,806, filed on Mar. 8, 2011, provisional application No. 61/410,748, filed on Nov. 5, 2010.

(51) Int. Cl.
| | |
|---|---|
| *A61K 41/00* | (2006.01) |
| *A61K 38/17* | (2006.01) |
| *A01K 67/027* | (2006.01) |
| *A61K 49/00* | (2006.01) |
| *A61B 5/16* | (2006.01) |
| *A61N 5/06* | (2006.01) |
| *A61K 9/00* | (2006.01) |
| *A61K 48/00* | (2006.01) |
| *C07K 14/705* | (2006.01) |
| *C12N 7/00* | (2006.01) |
| *C12N 15/85* | (2006.01) |
| *C12N 15/86* | (2006.01) |
| *G01N 33/50* | (2006.01) |

(52) U.S. Cl.
CPC ........ *A61K 38/177* (2013.01); *A01K 67/0275* (2013.01); *A01K 67/0278* (2013.01); *A61B 5/165* (2013.01); *A61K 9/0019* (2013.01); *A61K 41/00* (2013.01); *A61K 48/0058* (2013.01); *A61K 49/0004* (2013.01); *A61K 49/0008* (2013.01); *A61N 5/062* (2013.01); *C07K 14/705* (2013.01); *C12N 7/00* (2013.01); *C12N 15/8509* (2013.01); *C12N 15/86* (2013.01); *G01N 33/5088* (2013.01); *A01K 2217/072* (2013.01); *A01K 2227/105* (2013.01); *A01K 2267/0356* (2013.01); *A01K 2267/0393* (2013.01); *C12N 2015/859* (2013.01); *C12N 2750/14143* (2013.01); *C12N 2799/025* (2013.01)

(58) Field of Classification Search
None
See application file for complete search history.

(56) References Cited

U.S. PATENT DOCUMENTS

| | | | |
|---|---|---|---|
| 2,968,302 | A | 1/1961 | Fry et al. |
| 3,131,690 | A | 5/1964 | Innis et al. |
| 3,499,437 | A | 3/1970 | Balamuth et al. |
| 3,567,847 | A | 3/1971 | Price |
| 4,343,301 | A | 8/1982 | Indech |
| 4,559,951 | A | 12/1985 | Dahl et al. |
| 4,616,231 | A | 10/1986 | Autrey et al. |
| 4,865,042 | A | 9/1989 | Umemura et al. |
| 4,879,284 | A | 11/1989 | Lang et al. |
| 5,032,123 | A | 7/1991 | Katz et al. |
| 5,041,224 | A | 8/1991 | Ohyama et al. |
| 5,082,670 | A | 1/1992 | Gage et al. |
| 5,249,575 | A | 10/1993 | Di Mino et al. |
| 5,267,152 | A | 11/1993 | Yang et al. |
| 5,290,280 | A | 3/1994 | Daikuzono et al. |
| 5,330,515 | A | 7/1994 | Rutecki et al. |
| 5,382,516 | A | 1/1995 | Bush |
| 5,411,540 | A | 5/1995 | Edell et al. |
| 5,445,608 | A | 8/1995 | Chen et al. |
| 5,460,950 | A | 10/1995 | Barr et al. |
| 5,460,954 | A | 10/1995 | Lee et al. |
| 5,470,307 | A | 11/1995 | Lindall |

(Continued)

FOREIGN PATENT DOCUMENTS

| | | |
|---|---|---|
| CN | 1079464 A | 12/1993 |
| CN | 102076866 A | 5/2011 |

(Continued)

OTHER PUBLICATIONS

Johnson, et al.; "Differential Biodistribution of Adenoviral Vector In Vivo as Monitored by Bioluminescence Imaging and Quantitative Polymerase Chain Reaction"; Human Gene Therapy; vol. 17, pp. 1262-1269 (Dec. 2006).

Schester, et al.; "Biodistribution of adeno-associated virus serotype 9 (AAV9) vector after intrathecal and intravenous delivery in mouse"; Frontiers in Neuroanatomy; vol. 8, Article 42, pp. 1-41 (Jun. 10, 2014).

Adamantidis, et al., "Optogenetic Interrogation of Dopaminergic Modulation of the Multiple Phases of Reward-Seeking Behavior", J. Neurosci, 2011, vol. 31, No. 30, pp. 10829-10835.

(Continued)

*Primary Examiner* — James D Schultz
(74) *Attorney, Agent, or Firm* — Bozicevic, Field & Francis LLP; Paula A. Borden

(57) ABSTRACT

Provided herein are animals expressing light-responsive opsin proteins in the basal lateral amygdala of the brain and methods for producing the same wherein illumination of the light-responsive opsin proteins causes anxiety in the animal. Also provided herein are methods for alleviating and inducing anxiety in an animal as well as methods for screening for a compound that alleviates anxiety in an animal.

12 Claims, 21 Drawing Sheets

(56) References Cited

U.S. PATENT DOCUMENTS

| | | |
|---|---|---|
| 5,495,541 A | 2/1996 | Murray et al. |
| 5,520,188 A | 5/1996 | Hennige et al. |
| 5,527,695 A | 6/1996 | Hodges et al. |
| 5,550,316 A | 8/1996 | Mintz |
| 5,641,650 A | 6/1997 | Turner et al. |
| 5,703,985 A | 12/1997 | Owyang et al. |
| 5,722,426 A | 3/1998 | Kolff |
| 5,738,625 A | 4/1998 | Gluck |
| 5,739,273 A | 4/1998 | Engelman et al. |
| 5,741,316 A | 4/1998 | Chen et al. |
| 5,755,750 A | 5/1998 | Petruska et al. |
| 5,756,351 A | 5/1998 | Isacoff et al. |
| 5,782,896 A | 7/1998 | Chen et al. |
| 5,795,581 A | 8/1998 | Segalman et al. |
| 5,807,285 A | 9/1998 | Vaitekunas et al. |
| 5,816,256 A | 10/1998 | Kissinger et al. |
| 5,836,941 A | 11/1998 | Yoshihara et al. |
| 5,898,058 A | 4/1999 | Nichols |
| 5,939,320 A | 8/1999 | Littman et al. |
| 6,056,738 A | 5/2000 | Marchitto et al. |
| 6,057,114 A | 5/2000 | Akong |
| 6,108,081 A | 8/2000 | Holtom et al. |
| 6,134,474 A | 10/2000 | Fischell et al. |
| 6,161,045 A | 12/2000 | Fischell et al. |
| 6,180,613 B1 | 1/2001 | Kaplitt et al. |
| 6,253,109 B1 | 6/2001 | Gielen |
| 6,303,362 B1 | 10/2001 | Kay et al. |
| 6,334,846 B1 | 1/2002 | Ishibashi et al. |
| 6,336,904 B1 | 1/2002 | Nikolchev |
| 6,346,101 B1 | 2/2002 | Alfano et al. |
| 6,364,831 B1 | 4/2002 | Crowley |
| 6,377,842 B1 | 4/2002 | Pogue et al. |
| 6,436,708 B1 | 8/2002 | Leone et al. |
| 6,473,639 B1 | 10/2002 | Fischell et al. |
| 6,480,743 B1 | 11/2002 | Kirkpatrick et al. |
| 6,489,115 B2 | 12/2002 | Lahue et al. |
| 6,497,872 B1 | 12/2002 | Weiss et al. |
| 6,506,154 B1 | 1/2003 | Ezion et al. |
| 6,536,440 B1 | 3/2003 | Dawson |
| 6,551,346 B2 | 4/2003 | Crossley |
| 6,567,690 B2 | 5/2003 | Giller et al. |
| 6,597,954 B1 | 7/2003 | Pless et al. |
| 6,609,020 B2 | 8/2003 | Gill |
| 6,615,080 B1 | 9/2003 | Unsworth et al. |
| 6,631,283 B2 | 10/2003 | Storrie et al. |
| 6,632,672 B2 | 10/2003 | Calos |
| 6,647,296 B2 | 11/2003 | Fischell et al. |
| 6,685,656 B1 | 2/2004 | Duarte et al. |
| 6,686,193 B2 | 2/2004 | Maher et al. |
| 6,721,603 B2 | 4/2004 | Zabara et al. |
| 6,729,337 B2 | 5/2004 | Dawson |
| 6,780,490 B1 | 8/2004 | Tanaka et al. |
| 6,790,652 B1 | 9/2004 | Terry et al. |
| 6,790,657 B1 | 9/2004 | Arya |
| 6,805,129 B1 | 10/2004 | Pless et al. |
| 6,808,873 B2 | 10/2004 | Murphy et al. |
| 6,810,285 B2 | 10/2004 | Pless et al. |
| 6,889,085 B2 | 5/2005 | Dawson |
| 6,918,872 B2 | 7/2005 | Yokoi |
| 6,921,413 B2 | 7/2005 | Mahadevan-Jansen et al. |
| 6,969,449 B2 | 11/2005 | Maher et al. |
| 6,974,448 B2 | 12/2005 | Petersen |
| 7,045,344 B2 | 5/2006 | Kay et al. |
| 7,091,500 B2 | 8/2006 | Schnitzer |
| 7,144,733 B2 | 12/2006 | Miesenbock et al. |
| 7,175,596 B2 | 2/2007 | Vitek et al. |
| 7,191,018 B2 | 3/2007 | Gielen et al. |
| 7,211,054 B1 | 5/2007 | Francis et al. |
| 7,220,240 B2 | 5/2007 | Struys et al. |
| 7,298,143 B2 | 11/2007 | Jaermann et al. |
| 7,313,442 B2 | 12/2007 | Velasco et al. |
| 7,603,174 B2 | 10/2009 | De Ridder |
| 7,610,100 B2 | 10/2009 | Jaax et al. |
| 7,613,520 B2 | 11/2009 | De Ridder |
| 7,686,839 B2 | 3/2010 | Parker |
| 7,824,869 B2 | 11/2010 | Hegemann et al. |
| 7,883,536 B1 | 2/2011 | Bendett |
| 7,988,688 B2 | 8/2011 | Webb et al. |
| 8,386,312 B2 | 2/2013 | Pradeep et al. |
| 8,398,692 B2 | 3/2013 | Deisseroth et al. |
| 8,401,609 B2 | 3/2013 | Deisseroth et al. |
| 8,603,790 B2 | 12/2013 | Deisseroth et al. |
| 8,696,722 B2 | 4/2014 | Deisseroth et al. |
| 8,716,447 B2 | 5/2014 | Deisseroth et al. |
| 8,729,040 B2 | 5/2014 | Deisseroth et al. |
| 8,815,582 B2 | 8/2014 | Deisseroth et al. |
| 8,834,546 B2 | 9/2014 | Deisseroth et al. |
| 8,864,805 B2 | 10/2014 | Deisseroth et al. |
| 8,906,360 B2 | 12/2014 | Deisseroth et al. |
| 8,926,959 B2 | 1/2015 | Deisseroth et al. |
| 8,932,562 B2 | 1/2015 | Deisseroth et al. |
| 8,956,363 B2 | 2/2015 | Deisseroth et al. |
| 8,962,589 B2 | 2/2015 | Deisseroth et al. |
| 9,057,734 B2 | 6/2015 | Cohen |
| 9,079,940 B2 | 7/2015 | Deisseroth et al. |
| 9,084,885 B2 | 7/2015 | Deisseroth et al. |
| 9,101,690 B2 | 8/2015 | Deisseroth et al. |
| 9,101,759 B2 | 8/2015 | Deisseroth et al. |
| 9,175,095 B2 | 11/2015 | Deisseroth et al. |
| 9,187,745 B2 | 11/2015 | Deisseroth et al. |
| 9,238,150 B2 | 1/2016 | Deisseroth et al. |
| 9,249,200 B2 | 2/2016 | Deisseroth et al. |
| 9,249,234 B2 | 2/2016 | Deisseroth et al. |
| 9,271,674 B2 | 3/2016 | Deisseroth et al. |
| 9,274,099 B2 | 3/2016 | Deisseroth et al. |
| 9,278,159 B2 | 3/2016 | Deisseroth et al. |
| 9,284,353 B2 | 3/2016 | Deisseroth et al. |
| 9,308,392 B2 | 4/2016 | Deisseroth et al. |
| 9,309,296 B2 | 4/2016 | Deisseroth et al. |
| 9,359,449 B2 | 6/2016 | Deisseroth et al. |
| 9,458,208 B2 | 10/2016 | Deisseroth et al. |
| 9,522,288 B2 | 12/2016 | Deisseroth et al. |
| 9,604,073 B2 | 3/2017 | Deisseroth et al. |
| 2001/0023346 A1 | 9/2001 | Loeb |
| 2002/0094516 A1 | 7/2002 | Calos et al. |
| 2002/0155173 A1 | 10/2002 | Chopp et al. |
| 2002/0164577 A1 | 11/2002 | Tsien et al. |
| 2002/0190922 A1 | 12/2002 | Tsao |
| 2002/0193327 A1 | 12/2002 | Nemerow et al. |
| 2003/0009103 A1 | 1/2003 | Yuste et al. |
| 2003/0026784 A1 | 2/2003 | Koch et al. |
| 2003/0040080 A1 | 2/2003 | Miesenbock et al. |
| 2003/0050258 A1 | 3/2003 | Calos |
| 2003/0082809 A1 | 5/2003 | Quail et al. |
| 2003/0088060 A1 | 5/2003 | Benjamin et al. |
| 2003/0097122 A1 | 5/2003 | Ganz et al. |
| 2003/0104512 A1 | 6/2003 | Freeman et al. |
| 2003/0125719 A1 | 7/2003 | Furnish |
| 2003/0144650 A1 | 7/2003 | Smith |
| 2003/0204135 A1 | 10/2003 | Bystritsky |
| 2003/0232339 A1 | 12/2003 | Shu et al. |
| 2004/0013645 A1 | 1/2004 | Monahan et al. |
| 2004/0015211 A1 | 1/2004 | Nurmikko et al. |
| 2004/0023203 A1 | 2/2004 | Miesenbock et al. |
| 2004/0034882 A1 | 2/2004 | Vale et al. |
| 2004/0039312 A1 | 2/2004 | Hillstead et al. |
| 2004/0049134 A1 | 3/2004 | Tosaya et al. |
| 2004/0068202 A1 | 4/2004 | Hansson et al. |
| 2004/0073278 A1 | 4/2004 | Pachys |
| 2004/0076613 A1 | 4/2004 | Mazarkis et al. |
| 2004/0122475 A1 | 6/2004 | Myrick et al. |
| 2004/0203152 A1 | 10/2004 | Calos |
| 2004/0216177 A1 | 10/2004 | Jordan et al. |
| 2004/0267118 A1 | 12/2004 | Dawson |
| 2005/0058987 A1 | 3/2005 | Shi et al. |
| 2005/0088177 A1 | 4/2005 | Schreck et al. |
| 2005/0107753 A1 | 5/2005 | Rezai et al. |
| 2005/0112759 A1 | 5/2005 | Radisic et al. |
| 2005/0119315 A1 | 6/2005 | Fedida et al. |
| 2005/0124897 A1 | 6/2005 | Chopra |
| 2005/0143295 A1 | 6/2005 | Walker et al. |
| 2005/0143790 A1 | 6/2005 | Kipke et al. |
| 2005/0153885 A1 | 7/2005 | Yun et al. |
| 2005/0197679 A1 | 9/2005 | Dawson |

(56) References Cited

U.S. PATENT DOCUMENTS

| | | |
|---|---|---|
| 2005/0202398 A1 | 9/2005 | Hegemann et al. |
| 2005/0215764 A1 | 9/2005 | Tuszynski et al. |
| 2005/0240127 A1 | 10/2005 | Seip et al. |
| 2005/0267011 A1 | 12/2005 | Deisseroth et al. |
| 2005/0267454 A1 | 12/2005 | Hissong et al. |
| 2005/0279354 A1 | 12/2005 | Deutsch et al. |
| 2006/0025756 A1 | 2/2006 | Francischelli et al. |
| 2006/0034943 A1 | 2/2006 | Tuszynski |
| 2006/0057192 A1 | 3/2006 | Kane |
| 2006/0057614 A1 | 3/2006 | Heintz |
| 2006/0058671 A1 | 3/2006 | Vitek et al. |
| 2006/0058678 A1 | 3/2006 | Vitek et al. |
| 2006/0100679 A1 | 5/2006 | DiMauro et al. |
| 2006/0106543 A1 | 5/2006 | Deco et al. |
| 2006/0155348 A1 | 7/2006 | de Charms |
| 2006/0161227 A1 | 7/2006 | Walsh et al. |
| 2006/0167500 A1 | 7/2006 | Towe et al. |
| 2006/0179501 A1 | 8/2006 | Chan et al. |
| 2006/0184069 A1 | 8/2006 | Vaitekunas |
| 2006/0190044 A1 | 8/2006 | Libbus et al. |
| 2006/0206172 A1 | 9/2006 | DiMauro et al. |
| 2006/0216689 A1 | 9/2006 | Maher et al. |
| 2006/0236525 A1 | 10/2006 | Sliwa et al. |
| 2006/0241697 A1 | 10/2006 | Libbus et al. |
| 2006/0253177 A1 | 11/2006 | Taboada et al. |
| 2006/0271024 A1 | 11/2006 | Gertner et al. |
| 2007/0027443 A1 | 2/2007 | Rose et al. |
| 2007/0031924 A1 | 2/2007 | Li et al. |
| 2007/0053996 A1 | 3/2007 | Boyden et al. |
| 2007/0054319 A1 | 3/2007 | Boyden et al. |
| 2007/0060915 A1 | 3/2007 | Kucklick |
| 2007/0060984 A1 | 3/2007 | Webb et al. |
| 2007/0135875 A1 | 6/2007 | Demarais et al. |
| 2007/0156180 A1 | 7/2007 | Jaax et al. |
| 2007/0191906 A1 | 8/2007 | Lyer et al. |
| 2007/0196838 A1 | 8/2007 | Chesnut et al. |
| 2007/0197918 A1 | 8/2007 | Vitek et al. |
| 2007/0219600 A1 | 9/2007 | Gertner et al. |
| 2007/0220628 A1 | 9/2007 | Glassman et al. |
| 2007/0239080 A1 | 10/2007 | Schaden et al. |
| 2007/0239210 A1 | 10/2007 | Libbus et al. |
| 2007/0253995 A1 | 11/2007 | Hildebrand |
| 2007/0260295 A1 | 11/2007 | Chen et al. |
| 2007/0261127 A1 | 11/2007 | Boyden et al. |
| 2007/0282404 A1 | 12/2007 | Cottrell et al. |
| 2007/0295978 A1 | 12/2007 | Coushaine et al. |
| 2008/0020465 A1 | 1/2008 | Padidam |
| 2008/0027505 A1 | 1/2008 | Levin et al. |
| 2008/0046053 A1 | 1/2008 | Wagner et al. |
| 2008/0033569 A1 | 2/2008 | Ferren et al. |
| 2008/0050770 A1 | 2/2008 | Zhang et al. |
| 2008/0051673 A1 | 2/2008 | Kong et al. |
| 2008/0060088 A1 | 3/2008 | Shin et al. |
| 2008/0065158 A1 | 3/2008 | Ben-Ezra et al. |
| 2008/0065183 A1 | 3/2008 | Whitehurst et al. |
| 2008/0077200 A1 | 3/2008 | Bendett et al. |
| 2008/0085265 A1 | 4/2008 | Schneider et al. |
| 2008/0088258 A1 | 4/2008 | Ng |
| 2008/0103551 A1 | 5/2008 | Masoud et al. |
| 2008/0119421 A1 | 5/2008 | Tuszynski et al. |
| 2008/0125836 A1 | 5/2008 | Streeter et al. |
| 2008/0167261 A1 | 7/2008 | Sclimenti |
| 2008/0175819 A1 | 7/2008 | Kingsman et al. |
| 2008/0176076 A1 | 7/2008 | Van Veggel et al. |
| 2008/0200749 A1 | 8/2008 | Zheng et al. |
| 2008/0221452 A1 | 9/2008 | Njemanze |
| 2008/0227139 A1 | 9/2008 | Deisseroth et al. |
| 2008/0228244 A1 | 9/2008 | Pakhomov et al. |
| 2008/0262411 A1 | 10/2008 | Dobak |
| 2008/0287821 A1 | 11/2008 | Jung et al. |
| 2008/0290318 A1 | 11/2008 | Van Veggel et al. |
| 2009/0030930 A1 | 1/2009 | Pradeep et al. |
| 2009/0054954 A1 | 2/2009 | Foley et al. |
| 2009/0069261 A1 | 3/2009 | Dodge et al. |
| 2009/0088680 A1 | 4/2009 | Deisseroth et al. |
| 2009/0093403 A1 | 4/2009 | Zhang et al. |
| 2009/0099038 A1 | 4/2009 | Deisseroth et al. |
| 2009/0112133 A1 | 4/2009 | Deisseroth et al. |
| 2009/0118800 A1 | 5/2009 | Deisseroth et al. |
| 2009/0131837 A1 | 5/2009 | Granville |
| 2009/0148861 A1 | 6/2009 | Pegan et al. |
| 2009/0157145 A1 | 6/2009 | Cauller |
| 2009/0254134 A1 | 10/2009 | Nikolov et al. |
| 2009/0268511 A1 | 10/2009 | Birge et al. |
| 2009/0306474 A1 | 12/2009 | Wilson |
| 2009/0319008 A1 | 12/2009 | Mayer |
| 2009/0326603 A1 | 12/2009 | Boggs et al. |
| 2010/0009444 A1 | 1/2010 | Herlitze et al. |
| 2010/0016783 A1 | 1/2010 | Bourke et al. |
| 2010/0021982 A1 | 1/2010 | Herlitze |
| 2010/0145418 A1 | 6/2010 | Zhang et al. |
| 2010/0146645 A1 | 6/2010 | Vasar et al. |
| 2010/0190229 A1 | 7/2010 | Zhang et al. |
| 2010/0234273 A1 | 9/2010 | Deisseroth et al. |
| 2011/0221970 A1 | 1/2011 | Vo-Dihn et al. |
| 2011/0092800 A1 | 4/2011 | Yoo et al. |
| 2011/0105998 A1 | 5/2011 | Deisseroth et al. |
| 2011/0112463 A1 | 5/2011 | Silver et al. |
| 2011/0125077 A1 | 5/2011 | Denison et al. |
| 2011/0125078 A1 | 5/2011 | Denison et al. |
| 2011/0159562 A1 | 6/2011 | Deisseroth et al. |
| 2011/0165681 A1 | 7/2011 | Boyden et al. |
| 2011/0166632 A1 | 7/2011 | Delp et al. |
| 2011/0233046 A1 | 9/2011 | Nikolenko et al. |
| 2011/0301529 A1 | 12/2011 | Zhang et al. |
| 2011/0311489 A1 | 12/2011 | Deisseroth et al. |
| 2012/0093772 A1 | 4/2012 | Horsager et al. |
| 2012/0121542 A1 | 5/2012 | Chuong et al. |
| 2012/0253261 A1 | 10/2012 | Poletto et al. |
| 2013/0030275 A1 | 1/2013 | Seymour et al. |
| 2013/0089503 A1 | 4/2013 | Deisseroth et al. |
| 2013/0144359 A1 | 6/2013 | Kishawi et al. |
| 2013/0284920 A1 | 10/2013 | Deisseroth et al. |
| 2013/0286181 A1 | 10/2013 | Betzig et al. |
| 2013/0288365 A1 | 10/2013 | Deisseroth et al. |
| 2013/0289669 A1 | 10/2013 | Deisseroth et al. |
| 2013/0317569 A1 | 11/2013 | Deisseroth et al. |
| 2013/0317575 A1 | 11/2013 | Deisseroth et al. |
| 2013/0330816 A1 | 12/2013 | Deisseroth et al. |
| 2013/0343998 A1 | 12/2013 | Deisseroth et al. |
| 2013/0347137 A1 | 12/2013 | Deisseroth et al. |
| 2014/0082758 A1 | 3/2014 | Deisseroth et al. |
| 2014/0148880 A1 | 5/2014 | Deisseroth et al. |
| 2014/0235826 A1 | 8/2014 | Deisseroth et al. |
| 2014/0271479 A1 | 9/2014 | Lammel et al. |
| 2014/0324133 A1 | 10/2014 | Deisseroth et al. |
| 2015/0040249 A1 | 2/2015 | Deisseroth et al. |
| 2015/0072394 A1 | 3/2015 | Deisseroth et al. |
| 2015/0112411 A1 | 4/2015 | Beckman et al. |
| 2015/0165227 A1 | 6/2015 | Deisseroth et al. |
| 2015/0174244 A1 | 6/2015 | Deisseroth et al. |
| 2015/0217128 A1 | 8/2015 | Deisseroth et al. |
| 2015/0218547 A1 | 8/2015 | Deisseroth et al. |
| 2015/0297719 A1 | 10/2015 | Deisseroth et al. |
| 2016/0002302 A1 | 1/2016 | Deisseroth et al. |
| 2016/0015996 A1 | 1/2016 | Deisseroth et al. |
| 2016/0038761 A1 | 2/2016 | Deisseroth et al. |
| 2016/0038764 A1 | 2/2016 | Deisseroth et al. |
| 2016/0045599 A1 | 2/2016 | Deisseroth et al. |
| 2016/0096036 A1 | 4/2016 | Deisseroth et al. |
| 2016/0175607 A1 | 6/2016 | Deisseroth et al. |

FOREIGN PATENT DOCUMENTS

| | | |
|---|---|---|
| CN | 103313752 A | 9/2013 |
| CN | 103476456 A | 12/2013 |
| EP | 1197144 | 4/2002 |
| EP | 1334748 | 8/2003 |
| EP | 1444889 | 8/2004 |
| EP | 1873566 | 1/2008 |
| JP | 6295350 | 10/1994 |
| JP | H 09505771 A | 6/1997 |
| JP | 2004534508 | 11/2004 |
| JP | 2005034073 A | 2/2005 |

(56) References Cited

FOREIGN PATENT DOCUMENTS

| | | |
|---|---|---|
| JP | 2007530027 A | 11/2007 |
| JP | 2008010422 A | 1/2008 |
| JP | 2010227537 A | 10/2010 |
| JP | 2012508581 | 4/2012 |
| WO | WO 1995/005214 | 2/1995 |
| WO | WO 1996/032076 | 10/1996 |
| WO | WO 2000/027293 | 5/2000 |
| WO | WO 2001/025466 | 4/2001 |
| WO | WO 2003/016486 | 2/2003 |
| WO | WO 2003/040323 | 5/2003 |
| WO | W0 2003/046141 | 6/2003 |
| WO | WO 2003/084994 | 10/2003 |
| WO | WO 2003/102156 | 12/2003 |
| WO | WO 2004/033647 | 4/2004 |
| WO | WO 2005/093429 | 10/2005 |
| WO | WO 2006/103678 | 10/2006 |
| WO | WO 2007/024391 | 3/2007 |
| WO | WO 2007/131180 | 11/2007 |
| WO | WO 2008/086470 | 7/2008 |
| WO | WO 2008/106694 | 9/2008 |
| WO | WO 2009/025819 | 2/2009 |
| WO | WO 2009/072123 | 6/2009 |
| WO | WO 2009/119782 | 10/2009 |
| WO | WO 2009/131837 | 10/2009 |
| WO | WO 2009/148946 | 12/2009 |
| WO | WO 2010/006049 | 1/2010 |
| WO | WO 2010/011404 | 1/2010 |
| WO | WO 2010/056970 | 5/2010 |
| WO | WO 2010/123993 | 10/2010 |
| WO | WO 2011/005978 | 1/2011 |
| WO | WO 2011/066320 | 6/2011 |
| WO | WO 2011/106783 | 9/2011 |
| WO | WO 2011/116238 | 9/2011 |
| WO | WO 2011/127088 | 10/2011 |
| WO | WO 2012/032103 | 3/2012 |
| WO | WO 2012/061676 | 5/2012 |
| WO | WO 2012/061681 | 5/2012 |
| WO | WO 2012/061684 | 5/2012 |
| WO | WO 2012/061688 | 5/2012 |
| WO | WO 2012/061690 | 5/2012 |
| WO | WO 2012/061741 | 5/2012 |
| WO | WO 2012/061744 | 5/2012 |
| WO | WO 2012/106407 | 8/2012 |
| WO | WO 2012/134704 | 10/2012 |
| WO | WO 2013/003557 | 1/2013 |
| WO | WO 2013/016486 | 1/2013 |
| WO | WO 2013/090356 | 6/2013 |
| WO | WO 2013/126521 | 8/2013 |
| WO | WO 2013/126762 | 8/2013 |
| WO | WO 2013/142196 | 9/2013 |
| WO | WO 2014/081449 | 5/2014 |
| WO | WO 2014/117079 | 7/2014 |
| WO | WO 2016/019075 | 2/2016 |

OTHER PUBLICATIONS

Aebischer, et al. "Long-Term Cross-Species Brain Transplantation of a Polymer-Encapsulated Dopamine-Secreting Cell Line", Experimental Neurology, 1991, vol. 111, pp. 269-275.

Ageta-Ishihara et al., "Chronic overload of SEPT4, a parkin substrate that aggregates in Parkinson's disease, cause behavioral alterations but not neurodegeneration in mice", Molecular Brain, 2013, vol. 6, 14 pages.

Ahmad, et al. "The *Drosophila rhodopsin* cytoplasmic tail domain is required for maintenance of rhabdomere structure." The FASEB Journal, 2007, vol. 21, p. 449-455.

Airan, et al.; "Integration of light-controlled neuronal firing and fast circuit imaging"; Current Opinion in Neurobiology; vol. 17, pp. 587-592 (2007).

Airan, et al., "Temporally Precise in vivo Control of Intracellular Signaling", 2009, Nature, vol. 458, No. 7241, pp. 1025-1029.

Akirav, et al. "The role of the medial prefrontal cortex-amygdala circuit in stress effects on the extinction of fear", Neural Plasticity, 2007: vol. 2007 Article ID:30873, pp. 1-11.

Ali; "Gene and stem cell therapy for retinal disorders"; vision-research.en—The Gateway to European Vision Research; accessed from http://www.vision-research.eu/index.php?id=696, 10 pages (accessed Jul. 24, 2015).

Ang, et at. "Hippocampal CA1 Circuitry Dynamically Gates Direct Cortical Inputs Preferentially at Theta Frequencies." The Journal of Neurosurgery, 2005, vol. 25, No. 42, pp. 9567-9580.

Araki, et al. "Site-Directed Integration of the cre Gene Mediated by Cre Recombinase Using a Combination of Mutant lox Sites", Nucleic Acids Research, 2002, vol. 30, No. 19, pp. 1-8.

Aravanis, et al. "An optical neural interface: in vivo control of rodent motor cortex with integrated fiberoptic and optogenetic technology," J. Neural. Eng., 2007, vol. 4(3):S143-S156.

Arenkiel, et al. "In vivo light-induced activation of neural circuitry in transgenic mice expressing Channelrhodopsin-2", Neuron, 2007, 54:205-218.

Argos, et al. "The integrase family of site-specific recombinases: regional similarities and global diversity", The EMBO Journal, 1986, vol. 5, No. 2, pp. 433-440.

Asano, et al.; "Optically Controlled Contraction of Photosensitive Skeletal Muscle Cells"; Biotechnology & Bioengineering; vol. 109, No. 1, pp. 199-204 (Jan. 2012).

Axoclamp-28 Microelectrode claim theory and operation. Accessed from https://physics.ucsd.edu/neurophysics/Manuals/Axon%20Instruments/Axoclamp-2B_Manual.pdf on Dec. 12, 2014.

Babin et al., "Zebrafish Models of Human Motor Neuron Diseases: Advantages and Limitations", Progress in Neurobiology (2014), 118:36-58.

Balint et al., "The Nitrate Transporting Photochemical Reaction Cycle of the Pharanois Halorhodopsin", Biophysical Journal, 2004, 86:1655-1663.

Bamberg et al. "Light-driven proton or chloride pumping by halorhodopsin." Proc. Natl. Academy Science USA, 1993, vol. 90, No. 2, p. 639-643.

Banghart, et al. "Light-activated ion channels for remote control of neuronal firing". Nature Neuroscience, 2004, vol. 7, No. 12 pp. 1381-1386.

Barchet, et al.; "Challenges and opportunities in CNS delivery of therapeutics for neurodegenerative diseases"; Expert Opinion on Drug Delivery; vol. 6, No. 3, pp. 211-225 (Mar. 16, 2009).

Basil et al.; "Is There Evidence for Effectiveness of Transcranial Magnetic Stimulation in the Treatment of Psychiatric Disorders?"; Psychiatry; vol. 1, No. 11, pp. 64-69 (Nov. 2005).

Bebbington et al., "The use of vectors based on gene amplification for the expression of cloned genes in mammalian cells in DNA cloning" vol. 3, Academic Press, New York, 1987.

Benabid "Future strategies to restore brain functions," Conference proceedings from Medicine Meets Millennium: World Congress of Medicine and Health, 2000, 6 pages.

Benoist et al. "In vivo sequence requirements of the SV40 early promotor region" Nature (London), 1981, vol. 290(5804): pp. 304-310.

Berges et al., "Transduction of Brain by Herpes Simplex Virus Vectors", Molecular Therapy, 2007, vol. 15, No. 1: pp. 20-29.

Berke, et al. "Addiction, Dopamine, and the Molecular Mechanisms of Memory", Molecular Plasticity, 2000, vol. 25: pp. 515-532.

Berlanga, et a.; "Cholinergic Interneurons of the Nucleus Accumbens and Dorsal Striatum are Activated by the Self-Administration of Cocaine"; Neuroscience; vol. 120, pp. 1149-1156 (2003).

Berndt et al. "Bi-stable neural state switches", Nature Neuroscience, 2008, vol. 12, No. 2: pp. 229-234.

Berndt et al., "Structure-guided transformation of channelrhodopsin into a light-activated chloride channel", Science, 2014, 344:420-424.

Berridge et al., "The Versatility and Universality of Calcium Signaling", Nature Reviews: Molecular Cell Biology, 2000, vol. 1: pp. 11-21.

Bi, et al. "Ectopic Expression of a Microbial-Type Rhodopsin Restores Visual Responses in Mice with Photoreceptor Degeneration", Neuron, 2006, vol. 50, No. 1: pp. 23 -33.

(56) References Cited

OTHER PUBLICATIONS

Bi, et al. "Synaptic Modifications in Cultured Hippocampal Neurons: Dependence on Spike Timing, Synaptic Strength, and Postsynaptic Cell Type", Journal of Neuroscience, 1998, vol. 18, No. 24: pp. 10464-10472.
Blomer et al., "Highly Efficient and Sustained Gene Transfer in Adult Neurons with Lentivirus Vector", Journal of Virology,1997, vol. 71, No. 9: pp. 6641-6649.
Bocquet et al. "A prokaryotic proton-gated ion channel from the nicotinic acetylcholine receptor family." Nature Letters, 2007, vol. 445, p. 116-119.
Bowers, et al.; "Genetic therapy for the nervous system"; Human Molecular Genetics; vol. 20, No. 1, pp. R28-R41 (2011).
Boyden, et al. "Millisecond-timescale, genetically targeted optical control of neural activity" Nature Neuroscience, 2005, vol. 8, No. 9: pp. 1263-1268.
Braun, "Two Light-activated Conductances in the Eye of the Green Alga *Volvox carteri*", 1999, Biophys J., vol. 76, No. 3, pp. 1668-1678.
Brewin; "The Nature and Significance of Memory Disturbance in Posttraumatic Stress Disorder"; Ann. Rev. Clin. Psychol.; vol. 7, pp. 203-227 (2011).
Brinton, et al. "Preclinical analyses of the therapeutic potential of allopregnanolone to promote neurogenesis in vitro and in vivo in transgenic mouse model of Alzheimer's disease." Current Alzheimer Research, 2006, vol. 3, No. 1: pp. 11-17.
Brosenitsch et al, "Physiological Patterns of Electrical Stimulation Can Induce Neuronal Gene Expression by Activating N-Type Calcium Channels," Journal of Neuroscience, 2001, vol. 21, No. 8, pp. 2571-2579.
Brown, et al. "Long-term potentiation induced by θ frequency stimulation is regulated by a protein phosphate-operated gate." The Journal of Neuroscience, 2000, vol. 20, No. 21, pp. 7880-7887.
Bruegmann, et al.; "Optogenetic control of heart muscle in vitro and in vivo"; Nature Methods; vol. 7, No. 11, pp. 897-900(Nov. 2010).
Bruegmann, et al.; "Optogenetics in cardiovascular research: a new tool for light-induced depolarization of cardiomyocytes and vascular smooth muscle cells in vitro and in vivo"; European Heart Journal; vol . 32, No. Suppl . 1, p. 997 (Aug. 2011).
Callaway, et al. "Photostimulation using caged glutamate reveals functional circuitry in living brain slices", Proc. Natl. Acad. Sci. USA., 1993, vol. 90: pp. 7661-7665.
Campagnola et al. "Fiber-coupled light-emitting diode for localized photostimulation of neurons expressing channelrhodopsin-2." Journal of Neuroscience Methods , 2008, vol. 169, Issue 1. Abstract only.
Cannon, et al.; "Endophenotypes in the Genetic Analyses of Mental Disorders"; Annu. Rev. Clin. Psychol.; vol. 2, pp. 267-290 (2006).
Cardin, et al. "Driving Fast spiking Cells Induces Gamma Rhythm and Controls Sensory Responses", 2009, Nature, vol. 459, vol. 7247, pp. 663-667.
Castagne, et al.; "Rodent Models of Depression: Forced Swim and Tail Suspension Behavioral Despair Tests in Rats and Mice"; Current Protocols in Pharmacology; Supp. 49, Unit 5.8.1-5.8.14 (Jun. 2010).
Cazillis, et al., "VIP and PACAP induce selective neuronal differentiation of mouse embryonic stem cells", Eur J Neurosci, 2004, 19(4):798-808.
Cenatiempo "Prokaryotic gene expression in vitro: transcription-translation coupled systems", Biochimie, 1986, vol. 68(4): pp. 505-515.
Chamanzar, et al.; "Deep Tissue Targeted Near-infrared Optogenetic Stimulation using Fully Implantable Upconverting Light Bulbs"; 2015 37th Annual International Conference of the IEEE Engineering in Medicine and Biology Society (EMBC), IEEE; doi: 10.1109/EMBC.2015.7318488, pp. 821-824 (Aug. 25, 2015).
Chinta, et al.; "Dopaminergic neurons"; The International Journal of Biochemistry & Cell Biology; vol. 37, pp. 942-946 (2005).
Chow et al., "Optogenetics and translation medicine", Sci Transl Med., 2013, 5(177):177.

Clark, et al.; "A future for transgenic livestock"; Nature Reviews Genetics; vol. 4, No. 10, pp. 825-833 (Oct. 2003).
Claudio et al. "Nucleotide and deduced amino acid sequences of Torpedo californica acetylcholine receptor gamma subunit." PNAS USA,1983, vol. 80, p. 1111-1115.
Collingridge et al. "Inhibitory post-synaptic currents in rat hippocampal CA1 neurones." J. Physiol., 1984, vol. 356, pp. 551-564.
Covington, et al. "Antidepressant Effect of Optogenetic Stimulation of the Medial Prefrontal Cortex." Journal of Neuroscience, 2010, vol. 30(48), pp. 16082-16090.
Cowan et al., "Targeting gene expression to endothelium in transgenic animals: a comparison of the human ICAM-2, PECAM-1, and endoglin promoters", Xenotransplantation, 2003, vol. 10, pp. 223-231.
Crouse, et al. "Expression and amplification of engineered mouse dihydrofolate reductase minigenes" Mol. Cell. Biol. , 1983, vol. 3(2): pp. 257-266.
Cucchiaro et al., "Electron-Microscopic Analysis of Synaptic Input from the Perigeniculate Nucleus to A-Laminae of the Lateral Geniculate Nucleus in Cats", The Journal of Comparitive Neurology, 1991, vol. 310, pp. 316-336.
Cucchiaro et al., "Phaseolus vulgaris leucoagglutinin (PHA-L): a neuroanatomical tracer for electron microscopic analysis of synaptic circuitry in the cat's dorsal lateral geniculate nucleus" J. Electron. Microsc. Tech., 1990, 15 (4):352-368.
Cui, et al., "Electrochemical deposition and characterization of conducting polymer polypyrrole/PSS on multichannel neural probes," Sensors and Actuators, 2001, vol. 93(1): pp. 8-18.
Dalva, et al. "Rearrangements of Synaptic Connections in Visual Cortex Revealed by Laser Photostimulation", Science, 1994,vol. 265, pp. 255-258.
Date, et al. "Grafting of Encapsulated Dopamine-Secreting Cells in Parkinson's Disease: Long-Term Primate Study", Cell Transplant, 2000, vol. 9, pp. 705-709.
Davis; "The many faces of epidermal growth factor repeats," The New Biologist; vol. 2, No. 5, pp. 410-419 (1990).
Day, et al.; "The Nucleus Accumbens and Pavlovian Reward Learning"; Neuroscientist; vol. 13, No. 2, pp. 148-159 (Apr. 2007).
De Foubert et al. "Fluoxetine-Induced Change in Rat Brain Expression of Brain-Derived Neurotrophic Factor Varies Depending on Length of Treatment," Neuroscience, 2004, vol. 128, pp. 597-604.
De Palma, et al.; "In Vivo Targeting of Tumor Endothelial Cells by Systemic Delivery of Lentiviral Vectors"; Human Gene Therapy; vol. 14, pp. 1193-1206 (Aug. 10, 2003).
Dederen, et al. "Retrograde neuronal tracing with cholera toxin B subunit: comparison of three different visualization methods", Histochemical Journal, 1994, vol. 26, pp. 856-862.
Definition of Psychosis (2015).
Deisseroth "Next-generation optical technologies for illuminating genetically targeted brain circuits," The Journal of Neuroscience, 2006, vol. 26, No. 41, pp. 10380-10386.
Deisseroth et al., "Excitation-neurogenesis Coupling in Adult Neural Stem/Progenitor Cells", 2004, Neuron, vol. 42, pp. 535-552.
Deisseroth et al., "Signaling from Synapse to Nucleus: Postsynaptic CREB Phosphorylation During Multiple Forms of Hippocampal Synaptic Plasticity", Neuron, 1996, vol. 16, pp. 89-101.
Deisseroth et al., "Signaling from Synapse to Nucleus: the logic Behind the Mechanisms", Currrent Opinion in Neurobiology, 2003, vol. 13, pp. 354-365.
Deisseroth et al., "Translocation of Calmodulin to the Nucleus Supports CREB Phosphorylation in Hippocampal Neurons", Nature, 1998, vol. 392, pp. 198-202.
Deisseroth, et al., "Controlling the Brain with Light", Scientific American, 2010, vol. 303, pp. 48-55.
Delaney et al., "Evidence for a long-lived 13-cis-containing intermediate in the photocycle of the leu 93 → ala bacteriorhodopsin mutant", J. Physical Chemistry B, 1997, vol. 101, No. 29, pp. 5619-5621.
Denk, W., et al. "Anatomical and functional imaging of neurons using 2-photon laser scanning microscopy", Journal of Neuroscience Methods, 1994, vol. 54, pp. 151-162.
Deonarain; "Ligand-targeted receptor-mediated vectors for gene delivery"; Exp. Opin. Ther. Patents; vol. 8, No. 1, pp. 53-69 (1998).

(56) References Cited

OTHER PUBLICATIONS

Ditterich, et al. "Microstimulation of visual cortex affects the speed of perceptual decisions", 2003, Nature Neuroscience, vol. 6, No. 8, pp. 891-898.
Dittgen, et al. "Lentivirus-based genetic manipulations of cortical neurons and their optical and electrophysiological monitoring in vivo", PNAS, 2004, vol. 101, No. 52, pp. 18206-18211.
Do Carmo, et al.; "Modeling Alzheimer's disease in transgenic rats"; Molecular Neurodegeneration; vol. 8, No. 37, 11 pages (2013).
Douglass, et al., "Escape Behavior Elicited by Single, Channelrhodopsin-2-evoked Spikes in Zebrafish Somatosensory Neurons", Curr Biol., 2008, vol. 18, No. 15, pp. 1133-1137.
Ebert et al., "A Moloney MLV-rat somatotropin fusion gene produces biologically active somatotropin in a transgenic pig", Mol. Endocrinology, 1988, vol. 2, pp. 277-283.
EBI accession No. EMBL: J05199; "N. pharaonis halorhodopsin (hop) gene, complete cds"; (Nov. 22, 1990).
EBI accession No. UNIPROT: A7U0Y6; "SubName: Full=Bacteriorhodopsin"; (Aug. 10, 2010).
EBI accession No. UNIPROT: B0R5N9; "Subname: Full=Bacteriorhodopsin"; (Apr. 8, 2008).
EBI accession No. UNIPROT: B4Y103; "SubName: Full=Channelrhodopsin-1"; (Sep. 23, 2008).
EBI accession No. UNIPROT: P15647; "RecName: Full=Halorhodopsin; Short=HR; Alt Name: Full=NpHR"; (Apr. 1, 1990).
Edelstein, et al.; "Gene therapy clinical trials worldwide 1989-2004—an overview"; The Journal of Gene Medicine; vol. 6, pp. 597-602 (2004).
Ehrlich I. et al. "Amygdala inhibitory circuits and the control of fear memory", Neuron, 2009, vol. 62: pp. 757-771.
Eijkelkamp, et al. "Neurological perspectives on voltage-gated sodium channels", Brain, 2012, 135:2585-2612.
Eisen, "Treatment of amyotrophic lateral sclerosis", Drugs Aging, 1999; vol. 14, No. 3, pp. 173-96.
Emerich, et al. "A Novel Approach to Neural Transplantation in Parkinson's Disease: Use of Polymer-Encapsulated Cell Therapy", Neuroscience and Biobehavioral Reviews, 1992, vol. 16, pp. 437-447.
Ensell, et al. "Silicon-based microelectrodes for neurophysiology, micromachined from silicon-on-insulator wafers," Med. Biol. Eng. Comput., 2000, vol. 38, pp. 175-179.
Ernst, et al. "Photoactivation of Channelrhodopsin", J. Biol. Chem., 2008, vol. 283, No. 3, pp. 1637-1643.
Esposito et al. "The integrase family of tyrosine recombinases: evolution of a conserved active site domain", Nucleic Acids Research, 1997, vol. 25, No. 18, pp. 3605-3614.
Evanko "Optical excitation yin and yang" Nature Methods, 2007, 4:384.
Fabian et al. "Transneuronal transport of lectins" Brain Research, 1985, vol. 344, pp. 41-48.
Falconer et al. "High-throughput screening for ion channel modulators," Journal of Biomolecular Screening, 2002, vol. 7, No. 5, pp. 460-465.
Farber, et al. "Identification of Presynaptic Neurons by Laser Photostimulation", Science, 1983, vol. 222, pp. 1025-1027.
Feng, et al. "Imaging Neuronal Subsets in Transgenic Mice Expressing Multiple Spectral Variants of GFP", Neuron, 2000, vol. 28, pp. 41-51.
Fenno et al., "The development and application of optogenetics", Annual Review of Neuroscience, 2011, vol. 34, No. 1, pp. 389-412.
Fiala et al., "Optogenetic approaches in neuroscience", Current Biology, Oct. 2010, 20(20):R897-R903.
Fisher, J. et al. "Spatiotemporal Activity Patterns During Respiratory Rhythmogenesis in the Rat Ventrolateral Medulla," The Journal of Neurophysiol, 2006, vol. 95, pp. 1982-1991.
Fitzsimons et al., "Promotors and Regulatory Elements that Improve Adeno-Associated Virus Transgene Expression in the Brain", 2002, Methods, vol. 28, pp. 227-236.

Foster, "Bright blue times", Nature, 2005, vol. 433, pp. 698-699.
Fox et al., "A gene neuron expression fingerprint of C. elegans embryonic motor neurons", BMC Genomics, 2005, 6(42):1-23.
Friedman, et al.; "Programmed Acute Electrical Stimulation of Ventral Tegmental Area Alleviates Depressive-Like Behavior"; Neuropsychopharmacology; vol. 34, pp. 1057-1066 (2009).
Garrido et al., "A targeting motif involved in sodium channel clustering at the axonal initial segment", Science, 2003, vol. 300, No. 5628, pp. 2091-2094.
Gelvich et al. "Contact flexible microstrip applicators (CFMA) in a range from microwaves up to short waves," IEEE Transactions on Biomedical Engineering, 2002, vol. 49, Issue 9: 1015-1023.
Genbank Accession No. AAG01180.1; Idnurm, et al.; pp. 1 (Mar. 21, 2001).
Genbank Accession No. ABT17417.1; Sharma, et al.; pp. 1 (Aug. 15, 2007).
GenBank Accession No. AC096118.6; Rattus norvegicus clone CH230-11 B15, 1-4, 24-25, Working Draft Sequence, 3 unordered pieces. May 10, 2003.
Genbank Accession No. BAA09452.1; Mukohata et al.; pp. 1 (Feb. 10, 1999).
Genbank Accession No. DQ094781 (Jan. 15, 2008).
GenBank Accession No. U79717.1; Rattus norvegicus dopamine 02 receptor 1-4, 24-25 gene, promoter region and exon 1. Jan. 31, 1997.
Gigg, et al. "Glutamatergic hippocampal formation projections to prefrontal cortex in the rat are regulated by GABAergic inhibition and show convergence with glutamatergic projections from the limbic thalamus," Hippocampus, 1994, vol. 4, No. 2, pp. 189-198.
Gilman, et al. "Isolation of sigma-28-specific promoters from *Bacillus subtilis* DNA" Gene, 1984, vol. 32(1-2): pp. 11-20.
Glick et al."Factors affecting the expression of foreign proteins in *Escherichia coli*", Journal of Industrial Microbiology, 1987, vol. 1(5): pp. 277-282.
Goekoop, R. et al. "Cholinergic challenge in Alzheimer patients and mild cognitive impairment differentially affects hippocampal activation—a pharmacological fMRI study." Brain, 2006, vol. 129, pp. 141-157.
Gold, et al. "Representation of a perceptual decision in developing oculomotor commands", Nature, 2000, vol. 404, pp. 390-394.
Gonzalez, et al., "Cell-Based Assays and Instrumentation for Screening Ion-Channel Targets", DDT, 1999, vol. 4, No. 9, pp. 431439.
Gordon, et al. "Regulation of Thy-1 Gene Expression in Transgenic Mice", Cell, 1987, vol. 50, pp. 445-452.
Gorelova et al., "The course of neural projection from the prefrontal cortex to the nucleus accumbens in the rat", Neuroscience, 1997, vol. 76, No. 3, pp. 689-706.
Goshen et al. "Dynamics of Retrieval Strategies for Remote Memories", Cell, 2011, col. 147: pp. 678-589.
Gottesman et al."Bacterial regulation: global regulatory networks," Ann. Rev. Genet. , 1984, vol. 18, pp. 415-441.
Gradinaru et al., "Optical Deconstruction of Parkinsonian neural circuitry," Science, Apr. 2009, 324(5925):354-359.
Gradinaru et al., "Targeting and readout strategies for fast optical neural control in vitro and in vivo", J Neuroscience, 2007, 27(52):14231-14238.
Gradinaru, et al. "ENpHR: a Natronomonas Halorhodopsin Enhanced for Optogenetic Applications", 2008, Brain Cell Biol., vol. 36 (1-4), pp. 129-139.
Gradinaru, et al., "Molecular and Cellular Approaches for Diversifying and Extending Optogenetics", Cell, 2010, vol. 141, No. 1, pp. 154-165.
Grady, et al.; "Age-Related Reductions in Human Recognition Memory Due to Impaired Encoding"; Science; vol. 269, No. 5221, pp. 218-221 (Jul. 14, 1995).
Greenberg, et al. "Three-year outcomes in deep brain stimulation for highly resistant obsessive-compulsive disorder," Neuropsychopharmacology, 2006, vol. 31, pp. 2384-2393.
Gregory, et al. "Integration site for *Streptomyces* phage φBT1 and development of site-specific integrating vectors", Journal of Bacteriology, 2003, vol. 185, No. 17, pp. 5320-5323.
Groth et al. "Phage integrases: biology and applications," Journal of Molecular Biology, 2004, vol. 335, pp. 667-678.

(56) References Cited

OTHER PUBLICATIONS

Groth, et al. "A phage integrase directs efficient site-specific integration in human cells", PNAS, 2000, vol. 97, No. 11, pp. 5995-6000.
Guatteo, et al. "Temperature sensitivity of dopaminergic neurons of the substantia nigra pars compacta: Involvement of transient receptor potential channels," Journal of Neurophysiol. , 2005, vol. 94, pp. 3069-3080.
Gulick, et al. "Transfection using DEAE-Dextran" Supplement 40, Current Protocols in Molecular Biology, 1997, Supplement 40, 9.2.1-9.2.10.
Gunaydin et al., "Ultrafast optogenetic control", Nature Neuroscience, 2010, vol. 13, No. 3, pp. 387-392.
Gur et al., "A Dissociation Between Brain Activity and Perception: Chromatically Opponent Cortical Neurons Signal Chromatic Flicker that is not Perceived", Vision Research, 1997, vol. 37, No. 4, pp. 377-382.
Haim, et al.; "Gene Therapy to the Nervous System"; Stem Cell and Gene-Based Therapy; Section 2, pp. 133-154 (2006).
Hallet et al. "Transposition and site-specific recombination: adapting DNA cut-and-paste mechanisms to a variety of genetic rearrangements," FEMS Microbiology Reviews, 1997, vol. 21, No. 2, pp. 157-178.
Hamer, et al. "Regulation In Vivo of a cloned mammalian gene: cadmium induces the transcription of a mouse metallothionein gene in SV40 vectors," Journal of Molecular Applied Genetics, 1982, vol. 1, No. 4, pp. 273-288.
Hammer et al., "Spontaneous inflammatory disease in transgenic rats expressing HLA-B27 and Human $\beta_2$m : an animal model of HLA-B27-associated human disorders", Cell, 1990, vol. 63, pp. 1099-1112.
Han, et a.; "Virogenetic and optogenetic mechanisms to define potential therapeutic targets in psychiatric disorders"; Neuropharmacology; vol. 62, pp. 89-100 (2012).
Han, et al., "Millisecond-Timescale Optical Control of Neural Dynamics in the Nonhuman Primate Brain"; Neuron; vol. 62, pp. 191-198 (Apr. 30, 2009).
Han, et al., "Multiple-Color Optical Activation, Silencing, and Desynchronization of Neural Activity with Single-Spike Temporal Resolution", PLoS One, 2007, vol. 2, No. 3, pp. 1-12.
Han; et al., "Two-color, bi-directional optical voltage control of genetically-targeted neurons", CoSyne Abstract Presentation, Presented Feb. 24, 2007.
Hausser, et al. "Tonic Synaptic Inhibition Modulates Neuronal Output Pattern and Spatiotemporal Synaptic Integration", Neuron, 1997, vol. 19, pp. 665-678.
Hegemann et al., "All-trans Retinal Constitutes the Functional Chromophore in *Chlamydomonas* rhodopsin", Biophys. J. , 1991, vol. 60, pp. 1477-1489.
Herlitze, et al., "New Optical Tools for Controlling Neuronal Activity", 2007, Curr Opin Neurobiol, vol. 17, No. 1, pp. 87-94.
Herry, et al. "Switching on and off fear by distinct neuronal circuits," Nature, 2008, vol. 454, pp. 600-606.
Heymann, et al.; "Expression of Bacteriorhodopsin in Sf9 and COS-1 Cells"; Journal of Bioenergetics and Biomembranes; vol. 29, No. 1, pp. 55-59 (1997).
Hikida et al., "Acetylcholine enhancement in the nucleus accumbens prevents addictive behaviors of cocaine and morphine", PNAS, May 2003, 100(10):6169-6173.
Hikida et al., "Increased sensitivity to cocaine by cholingergic cell ablation in nucleus accumbens," PNAS, Nov. 2001, 98(23):13351-13354.
Hildebrandt et al, "Bacteriorhodopsin expressed in *Schizosaccharomyces pombe* pumps protons through the plasma membrane," PNAS, 1993, vol. 90, pp. 3578-3582.
Hira et al., "Transcranial optogenetic stimulation for functional mapping of the motor cortex", J Neurosci Methods, 2009, vol. 179, pp. 258-263.
Hirase, et al. "Multiphoton stimulation of neurons", J Neurobiol, 2002, vol. 51, No. 3: pp. 237-247.

Hodaie, et al., "Chronic Anterior Thalamus Stimulation for Intractable Epilepsy," Epilepsia, 2002, vol. 43, pp. 603-608.
Hoffman et al., "K+ Channel Regulation of Signal Propagation in Dendrites of Hippocampal Pyramidal Neurons", 1997, Nature, vol. 387: pp. 869-874.
Hofherr et al. "Selective Golgi export of Kir2.1 controls the stoichiometry of functional Kir2.x channel heteromers"Journal of Cell Science, 2005, vol. 118, p. 1935-1943.
Hosokawa, T. et al. "Imaging spatio-temporal patterns of long-term potentiation in mouse hippocampus." Philos. Trans. R. Soc. Lond. B., 2003, vol. 358, pp. 689-693.
Hososhima, et al.; "Near-infrared (NIR) up-conversion optogenetics"; Optical Techniques in Neurosurgery, Neurophotonics, and Optogenetics II; vol. 9305, doi: 10.1117/12.2078875, 4 pages (2015).
Hustler; et al., "Acetylcholinesterase staining in human auditory and language cortices: regional variation of structural features", Cereb Cortex (Mar.-Apr. 1996), 6(2):260-70.
Hynynen, et al. "Clinical applications of focused ultrasound—The brain." Int. J. Hyperthermia, 2007, vol. 23, No. 2: pp. 193-202.
Ibbini, et al.; "A Field Conjugation Method for Direct Synthesis of Hyperthermia Phased-Array Heating Patterns"; IEEE Transactions on Ultrasonics, Ferroelectrics, and Frequency Control; vol. 36, No. 1, pp. 3-9 (Jan. 1989).
Ihara, et al.; "Evolution of the Archaeal Rhodopsins: Evolution Rate Changes by Gene Duplication and Functional Differentiation"; J. Mol. Biol.; vol. 285, pp. 163-174 (1999).
International Search Report for International Application No. PCT/US2009/053474, dated Oct. 8, 2009.
Isenberg et al.; "Cloning of a Putative Neuronal Nicotinic Aceylcholine Receptor Subunit"; Journal of Neurochemistry; vol. 52, No. 3, pp. 988-991 (1989).
Iyer et al., "Virally mediated optogenetic excitation and inhibition of pain in freely moving nontransgenic mice", Nat Biotechnol., 2014, 32(3):274-8.
Jekely, "Evolution of Phototaxis", 2009, Phil. Trans. R. Soc. B, vol. 364, pp. 2795-2808.
Jennings et al., "Distinct extended amygdala circuits for divergent motivational states," Nature, 2013, 496:224-228.
Ji et al., "Light-evoked Somatosensory Perception of Transgenic Rats that Express Channelrhodopsin-2 in Dorsal Root Ganglion Cells", PLoS One, 2012 7(3):e32699.
Jimenez S.A & Maren S. et al/ "Nuclear disconnection within the amygdala reveals a direct pathway to fear", Learning Memory, 2009, vol. 16: pp. 766-768.
Johansen, et al., "Optical Activation of Lateral Amygdala Pyramidal Cells Instructs Associative Fear Learning", 2010, PNAS, vol. 107, No. 28, pp. 12692-12697.
Johnson-Saliba, et al.; "Gene Therapy: Optimising DNA Delivery to the Nucleus"; Current Drug Targets; vol. 2, pp. 371-399(2001).
Johnston et al. "Isolation of the yeast regulatory gene GAL4 and analysis of its dosage effects on the galactose/melibiose regulon," PNAS, 1982, vol. 79, pp. 6971-6975.
Kaiser; "Clinical research. Death prompts a review of gene therapy vector"; Science; 317(5838):580, 1 page (Aug. 3, 2007).
Kandel, E.R.,et al. "Electrophysiology of Hippocampal Neurons: I. Sequential Invasion and Synaptic Organization," J Neurophysiol, 1961, vol. 24, pp. 225-242.
Kandel, E.R.,et al. "Electrophysiology of Hippocampal Neurons: II. After-Potentials and Repetitive Firing", J Neurophysiol., 1961, vol. 24, pp. 243-259.
Karra, et al. "Transfection Techniques for Neuronal Cells", The Journal of Neuroscience, 2010, vol. 30, No. 18, pp. 6171-6177.
Karreman et al. "On the use of double FLP recognition targets (FRTs) in the LTR of retroviruses for the construction of high producer cell lines" , Nucleic Acids Research, 1996, vol. 24, No. 9: pp. 1616-1624.
Kato et al. "Present and future status of noninvasive selective deep heating using RF in hyperthermia." Med & Biol. Eng. & Comput 31 Supp: S2-11, 1993. Abstract p. S2 only.
Katz, et al. "Scanning laser photostimulation: a new approach for analyzing brain circuits," Journal of Neuroscience Methods, 1994, vol. 54, pp. 205-218.

(56) References Cited

OTHER PUBLICATIONS

Kay; "State of the art gene-based therapies: the road ahead"; Nature Reviews Genetics; vol. 12, pp. 316-328 (May 2011).
Kelder et al., "Glycoconjugates in human and transgenic animal milk", Advances in Exp. Med. and Biol., 2001, vol. 501, pp. 269-278.
Kessler, et al.; "Gene delivery to skeletal muscle results in sustained expression and systemic delivery of a therapeutic protein"; Proc. Natl. Acad. Sci. USA; vol. 93, pp. 14082-14087 (Nov. 1996).
Khodakaramian, et al. "Expression of Cre Recombinase during Transient Phage Infection Permits Efficient Marker Removal in *Streptomyces*," Nucleic Acids Research, 2006, vol. 34, No. 3:e20, pp. 1-5.
Khosravani et al., "Voltage-Gated Calcium Channels and Idiopathic Generalized Epilepsies", Physiol. Rev., 2006, vol. 86: pp. 941-966.
Kianianmomeni, et al. "Channelrhodopsins of Volvox carteri are Photochromic Proteins that are Specifically Expressed in Somatic Cells under Control of Light, Temperature, and the Sex Inducer", 2009, Plant Physiology, vol. 151, No. 1, pp. 347-366.
Kim et al., "Diverging neural pathways assemble a behavioural state from separable features in anxiety" Nature, 2013, 496(7444):219-23.
Kim et al., "Light-Driven Activation of β2-Adrenergic Receptor Signaling by a Chimeric Rhodopsin Containing the β2-Adrenergic Receptor Cytoplasmic Loops," Biochemistry, 2005, vol. 44, No. 7, pp. 2284-2292.
Kim et al., "PDZ domain proteins of synapses", Nature Reviews Neuroscience, 2004, vol. 5, No. 10, pp. 771-781.
Kingston et al. "Transfection and Expression of Cloned DNA," Supplement 31, Current Protocols in Immunology, 1999, 10.13.1-1 0.13.9.
Kingston et al. "Transfection of DNA into Eukaryotic Cells," Supplement 63, Current Protocols in Molecular Biology, 1996, 9.1.1-9.1.11, 11 pages.
Kinoshita, et al., "Optogenetically Induced Supression of Neural Activity in the Macaque Motor Cortex", Poster Sessions Somatomotor System, Others, Society for Neuroscience Meeting, 2010, pp. 141-154.
Kita, H. et al. "Effects of dopamine agonists and antagonists on optical responses evoked in rat frontal cortex slices after stimulation of the subcortical white matter," Exp. Brain Research, 1999, vol. 125, pp. 383-388.
Kitabatake et al., "Impairment of reward-related learning by cholinergic cell ablationn in the striatum", PNAS, Jun. 2003, 100(13):7965-7970.
Kitayama, et al. "Regulation of neuronal differentiation by N-methyl-D-aspartate receptors expressed in neural progenitor cells isolated from adult mouse hippocampus," Journal of Neurosci Research, 2004, vol. 76, No. 5: pp. 599-612.
Klausberger, et al. "Brain-state- and cell-type-specific firing of hippocampal interneurons in vivo", Nature, 2003, vol. 421: pp. 844-848.
Knopfel, et al. "Optical Probing of Neuronal Circuit Dynamics: Gentically Encoded Versus Classical Fluorescent Sensors", 2006, Trends Neurosci, vol. 29, No. 3, pp. 160-166.
Knopfel, et al.; "A comprehensive concept of optogenetics"; Progress in Brain Research; vol. 196, pp. 1-28 (2012).
Kocsis et al., "Regenerating Mammalian Nerve Fibres: Changes in Action Potential Wavefrom and Firing Characteristics Following Blockage of Potassium Conductance", 1982, Proc. R. Soc. Lond., vol. B 217: pp. 77-87.
Kokel et al., "Photochemical activation of TRPA1 channels in neurons and animals", Nat Chem Biol, 2013, 9(4):257-263.
Kuhlman et al. (2008) "High-Resolution Labeling and Functional Manipulation of Specific Neuron Types in Mouse Brain by Cre-Activated Viral Gene Expression" PLoS ONE, e2005, vol. 3, No. 4, pp. 1-11.
Kunkler, P. et at. "Optical Current Source Density Analysis in Hippocampal Organotypic Culture Shows that Spreading Depression Occurs with Uniquely Reversing Current," The Journal of Neuroscience, 2005, vol. 25, No. 15, pp. 3952-3961.
Lalumiere, R., "A new technique for controlling the brain: optogenetics and its potential for use in research and the clinic", Brain Stimulation, 2011, vol. 4, pp. 1-6.
Lammel et al., "Input-specific control of reward and aversion in the ventral tegmental area", Nature, 2012, 491(7423): 212-217.
Landy, A. "Mechanistic and structural complexity in the site-specific recombination pathways of Int and FLP", Current Opinion in Genetics and Development, 1993, vol. 3, pp. 699-707.
Lanyi et al. "The primary structure of a Halorhodopsin from Natronobacterium Pharaonis" Journal of Biological Chemistry, 1990, vol. 265, No. 3, p. 1253-1260.
Lee et al. "Sterotactic Injection of Adenoviral Vectors that Target Gene Expression to Specific Pituitary Cell Types: Implications for Gene Therapy", Neurosurgery, 2000, vol. 46, No. 6: pp. 1461-1469.
Lee et al., "Potassium Channel Gene Therapy Can Prevent Neuron Death Resulting from Necrotic and Apoptotic Insults", Journal of Neurochemistry, 2003, vol. 85: pp. 1079-1088.
Levitan et al. "Surface Expression of Kv1 Voltage-Gated K+ Channels Is Governed by a C-terminal Motif," Trends Cardiovasc. Med., 2000, vol. 10, No. 7, pp. 317-320.
Li et al. "Fast noninvasive activation and inhibition of neural and network activity by vertebrate rhodopsin and green algae channelrhodopsin." PNAS, 2005, vol. 102, No. 49, p. 17816-17821.
Li et al., "Surface Expression of Kv1 Channels is Governed by a C-Terminal Motif", J. Biol. Chem. (2000), 275(16):11597-11602.
Lim et al., "A Novel Targeting Signal for Proximal Clustering of the Kv2.1K+ Channel in Hippocampal Neurons", Neuron, 2000, vol. 25: pp. 385-397.
Lima, et al. "Remote Control of Behavior through Genetically Targeted Photostimulation of Neurons", Cell, 2005, vol. 121: pp. 141-152.
Liman, et al. "Subunit Stoichiometry of a Mammalian K+ Channel Determined by Construction of Multimeric cDNAs," Neuron, 1992,vol. 9, pp. 861-871.
Lin, "A user's guide to channelrhodopsin variants: features, limitations and future developments", Exp Physiol, 2010, vol. 96, No. 1, pp. 19-25.
Liske et al., "Optical inhibition of motor nerve and muscle activity in vivo", Muscle Nerve, 2013, 47(6):916-21.
Liu et al., "Optogenetics 3.0", Cell, Apr. 2010, 141(1):22-24.
Llewellyn et al., "Orderly recruitment of motor units under optical control in vivo", Nat Med., 2010, 16(10):1161-5.
Loetterle, et al., "Cerebellar Stimulation: Pacing the Brain", American Journal of Nursing, 1975, vol. 75, No. 6, pp. 958-960.
Lonnerberg et al. "Regulatory Region in Choline Acetyltransferase Gene Directs Developmental and Tissue-Specific Expression in Transgenic mice", Proc. Natl. Acad. Sci. USA (1995), 92(9):4046-4050.
Louis et al. "Cloning and sequencing of the cellular-viral junctions from the human adenovirus type 5 transformed 293 cell line," Virology, 1997, vol. 233, pp. 423-429.
Luecke, et al. "Structural Changes in Bacteriorhodopsin During Ion Transport at 2 Angstrom Resolution," Science, 1999, vol. 286, pp. 255-260.
Lyznik, et al. "FLP-mediated recombination of FRT sites in the maize genome," Nucleic Acids Research , 1996, vol. 24, No. 19: pp. 3784-3789.
Ma et al. "Role of ER Export Signals in Controlling Surface Potassium Channel Numbers," Science, 2001, vol. 291, pp. 316-319.
Malin et al., "Involvement of the rostral anterior cingulate cortex in consolidation of inhibitory avoidance memory: Interaction with the basolateral amygdala", Neurobiol Learn Mem., Feb. 2007, 87(2):295-302.
Mancuso et al., "Optogenetic probing of functional brain circuitry", Experimental Physiology, 2010, vol. 96.1, pp. 26-33.
Mann et at. "Perisomatic Feedback Inhibition Underlies Cholinergically Induced Fast Network Oscillations in the Rat Hippocampus in Vitro," Neuron, 2005, vol. 45, 2005, pp. 105-117.
Mann; "Synapses"; The Nervous System in Action; Chapter 13, http://michaeldmann.net/mann13.html (downloaded Apr. 2014).

(56) References Cited

OTHER PUBLICATIONS

Marin, et al., The Amino Terminus of the Fourth Cytoplasmic Loop of Rhodopsin Modulates Rhodopsin-Transduction Interaction, The Journal of Biological Chemistry, 2000, vol. 275, pp. 1930-1936.
Mattis et al., "Principles for applying optogenetic tools derived from direct comparative analysis of microbial opsins", Nat Methods, 2011, 9(2):159-72.
Mattson, "Apoptosis in Neurodegenerative Disorders", Nature Reviews, 2000, vol. 1: pp. 120-129.
Mayberg et al. "Deep Brain Stimulation for Treatment-Resistant Depression," Focus, 2008, vol. VI, No. 1, pp. 143-154.
Mayford et al., "Control of memory formation through regulated expression of CaMKII transgene", Science, Dec. 1996, 274(5293):1678-1683.
McAllister, "Cellular and Molecular Mechanisms of Dendrite Growth", 2000, Cereb Cortex, vol. 10, No. 10, pp. 963-973.
McKnight "Functional relationships between transcriptional control signals of the thymidine kinase gene of herpes simplex virus", Cell, 1982, vol. 31 pp. 355-365.
Melyan, Z., et al. "Addition of human melanopsin renders mammalian cells photoresponsive", Nature, 2005, vol. 433: pp. 741-745.
Mermelstein, et al. "Critical Dependence of cAMP Response Element-Binding Protein Phosphorylation on L-Type Calcium Channels Supports a Selective Response to EPSPs in Preference to Action Potentials", The Journal of Neuroscience, 2000, vol. 20, No. 1, pp. 266-273.
Meyer, et al. "High density interconnects and flexible hybrid assemblies for active biomedical implants," IEEE Transactions on Advanced Packaging , 2001, vol. 24, No. 3, pp. 366-372.
Milella et al. "Opposite roles of dopamine and orexin in quinpirole-induced excessive drinking: a rat model of psychotic polydipsia" Psychopharmacology, 2010, 211:355-366.
Monje et al., "Irradiation Induces Neural Precursor-Cell Dysfunction", Natural Medicine, 2002, vol. 8, No. 9, pp. 955-962.
Morelli et al., "Neuronal and glial cell type-specific promoters within adenovirus recombinants restrict the expression of the apoptosis-inducing molecule Fas ligand to predetermined brain cell types, and abolish peripheral liver toxicity", Journal of General Virology, 1999, 80:571-583.
Mortensen et al. "Selection of Transfected Mammalian Cells," Supplement 86, Current Protocols in Molecular Biology, 1997, 9.5.1-09.5.19.
Mourot et al., "Rapid Optical Control of Nociception with an Ion Channel Photoswitch", Nat Methods, 2012, 9(4):396-402.
Mueller, et al.; "Clinical Gene Therapy Using Recombinant Adeno-Associated Virus Vectors"; Gene Therapy; vol. 15, pp. 858-863 (2008).
Mullins et al., "Expression of the DBA/2J Ren-2 gene in the adrenal gland of transgenic mice", EMBO, 1989, vol. 8, pp. 4065-4072.
Mullins et al., "Fulminant hypertension in transgenic rats harbouring the mouse Ren-2 gene", Nature, 1990, vol. 344, pp. 541-544.
Nacher, et al. "NMDA receptor antagonist treatment increases the production of new neurons in the aged rat hippocampus", Neurobiology of Aging, 2003,vol. 24, No. 2: pp. 273-284.
Nagel et al."Functional Expression of Bacteriorhodopsin in Oocytes Allows Direct Measurement of Voltage Dependence of Light Induced H+ Pumping," FEBS Letters, 1995, vol. 377, pp. 263-266.
Nagel, et al. "Channelrhodopsin-l: a light-gated proton channel in green algae", Science, 2002, vol. 296: pp. 2395-2398.
Nagel, et al. "Channelrhodopsin-2, a directly light-gated cation-selective membrane channel", PNAS, 2003, vol. 100, No. 24: pp. 13940-13945.
Nakagami, et al. "Optical Recording of Trisynaptic Pathway in Rat Hippocampal Slices with a Voltage-Sensitive Dye" Neuroscience, 1997, vol. 81, No. 1, pp. 1-8.
Naqvi, et al. "Damage to the insula disrupts addiction to cigarette smoking," Science; 2007, vol. 315 pp. 531-534.
Natochin, et al. "Probing rhodopsin-transducin interaction using *Drosophila* Rh1-bovine rhodopsin chimeras", Vision Res., 2006, vol. 46, No. 27: pp. 4575-4581.

Nieh et al., "Optogenetic dissection of neural circuits underlying emotional valence and motivated behaviors", Brain Research, E-pub 2012, 1511:73-92.
Nirenberg, et al. "The Light Response of Retinal Ganglion Cells is Truncated by a Displaced Amacrine Circuit", Neuron, 1997, vol. 18: pp. 637-650.
No Authors Listed; "Two bright new faces in gene therapy," Nature Biotechnology, 1996, vol. 14: p. 556.
Nonet, "Visualization of synaptic specializations in live C. elegans with synaptic vesicle protein-GFP fusions", J. Neurosci. Methods, 1999, 89:33-40.
Nunes-Duby, et al. "Similarities and differences among 105 members of the Int family of site-specific recombinases" , Nucleic Acids Research, 1998, vol. 26, No. 2: pp. 391-406.
O'Gorman et al. "Recombinase-mediated gene activation and site-specific integration in mammalian cells", Science, 1991, 251(4999): pp. 1351-1355.
Olivares (2001) "Phage R4 integrase mediates site-specific integration in human cells", Gene, 2001, vol. 278, pp. 167-176.
Ory, et al. "A stable human-derived packaging cell line for production of high titer retrovirus/vesicular stomatitis virus G pseudotypes," PNAS, 1996, vol. 93: pp. 11400-11406.
Packer, et al.; "Targeting Neurons and Photons for Optogenetics"; Nature Neuroscience; vol. 16, No. 7, pp. 805-815 (Jul. 2013).
Palmer et al., "Fibroblast Growth Factor-2 Activates a Latent Neurogenic Program in Neural Stem Cells from Diverse Regions of the Adult CNS", The Journal of Neuroscience, 1999, vol. 19, pp. 8487-8497.
Palmer et al., "The Adult Rat Hippocampus Contains Primordial Neural Stem Cells", Molecular and Cellular Neuroscience, 1997, vol. 8, pp. 389-404.
Palu, et al.; "In pursuit of new developments for gene therapy of human diseases"; Journal of Biotechnology; vol. 68, pp. 1-13 (1999).
Pan et al. "Functional Expression of a Directly Light-Gated Membrane Channel in Mammalian Retinal Neurons: A Potential Strategy for Restoring Light Sensitivity to the Retina After Photoreceptor Degeneration"; Investigative Opthalmology & Visual Science, 2005, 46 E-Abstract 4631. Abstract only.
Panda, et al. "Illumination of the Melanopsin Signaling Pathway", Science, 2005, vol. 307: pp. 600-604.
Pandya, et al.; "Where in the Brain Is Depression?"; Curr. Psychiatry Rep.; vol. 14, pp. 634-642 (2012).
Pape, et al., "Plastic Synaptic Networks of the Amygdala for the Acquisition, Expression, and Extinction of Conditioned Fear", 2010, Physiol Rev, vol. 90, pp. 419-463.
Paulhe et al. "Specific Endoplasmic Reticulum Export Signal Drives Transport of Stem Cell Factor (Kitl) to the Cell Surface," The Journal of Biological Chemistry, 2004, vol. 279, No. 53, p. 55545-55555.
Pear "Transient Transfection Methods for Preparation of High-Titer Retroviral Supernatants" Supplement 68, Current Protocols in Molecular Biology, 1996, 9.1 1 .1-9.1 1 .1 8.
Peralvarez-Marin et al., "Inter-helical hydrogen bonds are essential elements for intra-protein signal transduction: The role of Asp115 in bacteriorhodopsin transport function", J. Mol. Biol., 2007, vol. 368, pp. 666-676.
Peterlin, et al. "Optical probing of neuronal circuits with calcium indicators," PNAS, 2000, vol. 97, No. 7: pp. 3619-3624.
Petersen, et al.; "Functionally Independent Columns of Rat Somatosensory Barrel Cortex Revealed with Voltage-Sensitive Dye Imaging"; J. of Neuroscience; vol. 21, No. 21, pp. 8435-8446 (Nov. 1, 2011).
Petersen et al. "Spatiotemporal Dynamics of Sensory Responses in Layer 2/3 of Rat Barrel Cortex Measured In Vivo by Voltage-Sensitive Dye Imaging Combined with Whole-Cell Voltage Recordings and Neuron Reconstructions," The Journal of Neuroscience, 2003, vol. 23, No. 3, pp. 1298-1309.
Petrecca, et al. "Localization and Enhanced Current Density of the Kv4.2 Potassium Channel by Interaction with the Actin-Binding Protein Filamin," The Journal of Neuroscience, 2000, vol. 20, No. 23, pp. 8736-8744.

(56) References Cited

OTHER PUBLICATIONS

Pettit, et al. "Local Excitatory Circuits in the Intermediate Gray Layer of the Superior Colliculus", J Neurophysiol., 1999, vol. 81, No. 3: pp. 1424-1427.
Pfeifer, et al. "Gene Therapy: Promises and Problems"; Annu. Rev. Genomics Hum. Genet.; vol. 2, pp. 177-211 (2001).
Pinkham et al., "Neural bases for impaired social cognition in schizophrenia and autism spectrum disorders", Schizophrenia Research, 2008, vol. 99, pp. 164-175.
Potter, "Transfection by Electroporation." Supplement 62, Current Protocols in Molecular Biology, 1996, 9.3.1-9.3.6.
Pouille, et al. "Routing of spike series by dynamic circuits in the hippocampus", Nature, 2004, vol. 429: pp. 717-723.
Powell, et al.; "Schizophrenia-Relevant Behavioral Testing in Rodent Models: A Uniquely Human Disorder?"; Biol. Psychiatry; vol. 59, pp. 1198-1207 (2006).
Qiu et al. "Induction of photosensitivity by heterologous expression of melanopsin", Nature, 2005, vol. 433: pp. 745-749.
Ramalho, et al.; "Mouse genetic corneal disease resulting from transgenic insertional mutagenesis"; Br. J. Ophthalmol.; vol. 88, No. 3, pp. 428-432 (Mar. 2004).
Rammes, et al., "Synaptic Plasticity in the Basolateral Amygdala in Transgenic Mice Expressing Dominant-Negative cAMP Response Element-binding Protein (CREB) in Forebrain", Eur J. Neurosci, 2000, vol. 12, No. 7, pp. 2534-2546.
Randic, et al. "Long-term Potentiation and Long-term Depression of Primary Afferent Neurotransmission in the Rat Spinal Cord", 1993, Journal of Neuroscience, vol. 13, No. 12, pp. 5228-5241.
Raper, et al.; "Fatal systemic inflammatory response syndrome in a ornithine transcarbamylase deficient patient following adenoviral gene transfer." Mol. Genet. Metab.; vol. 80, No. 1-2, pp. 148-158 (Sep.-Oct. 2003).
Rathnasingham et al., "Characterization of implantable microfabricated fluid delivery devices," IEEE Transactions on Biomedical Engineering, 2004, vol. 51, No. 1: pp. 138-145.
Rein, et al., "The Optogenetic (r)evolution", Mol. Genet. Genomics, 2012, vol. 287, No. 2, pp. 95-109.
Remy, et al., "Depression in Parkinson's Disease: Loss of Dopamine and Noradrenaline Innervation in the Limbic System", Brain, 2005, vol. 128 (Pt 6), pp. 1314-1322.
Ristevski; "Making Better Transgenic Models: Conditional, Temporal, and Spatial Approaches"; Molecular Biotechnology; vol. 29, No. 2, pp. 153-163 (Feb. 2005).
Ritter, et al., "Monitoring Light-induced Structural Changes of Channelrhodopsin-2 by UV-Visible and Fourier Transform Infared Spectroscopy", 2008, The Journal of Biological Chemistry, vol. 283, No. 50, pp. 35033-35041.
Rivera et al., "BDNF-Induced TrkB Activation Down-Regulates the K+-Cl-cotransporter KCC2 and Impairs Neuronal Cl-Extrusion", The Journal of Cell Biology, 2002, vol. 159: pp. 747-752.
Rosenkranz, et al. "The prefrontal cortex regulates lateral amygdala neuronal plasticity and responses to previously conditioned stimuli", J. Neurosci., 2003, vol. 23, No. 35: pp. 11054-11064.
Rousche, et al., "Flexible polyimide-based intracortical electrode arrays with bioactive capability," IEEE Transactions on Biomedical Engineering, 2001, vol. 48, No. 3, pp. 361-371.
Rubinson et at. "A lentivirus-based system to functionally silence genes in primary mammalian cells, stem cells and transgenic mice by RNA interference," Nature Genetics, 2003, vol. 33, p. 401-406.
Rudiger et at. "Specific arginine and threonine residues control anion binding and transport in the light-driven chloride pump halorhodopsin," The EMBO Journal, 1997, vol. 16, No. 13, pp. 3813-3821.
Sajdyk, et al., "Excitatory Amino Acid Receptors in the Basolateral Amygdala Regulate Anxiety Responses in the Social Interaction Test", Brain Research, 1997, vol. 764, pp. 262-264.
Salzman, et al. "Cortical microstimulation influences perceptual judgements of motion direction", Nature, 1990, vol. 346, pp. 174-177.
Samuelson; "Post-traumatic stress disorder and declarative memory functioning: a review"; Dialogues in Clinical Neuroscience; vol. 13, No. 3, pp. 346-351 (2011).
Santana et al., "Can Zebrafish Be Used as Animal Model to Study Alzheimer's Disease?" Am. J. Neurodegener. Dis. (2012), 1(1)32-48.
Sato et al. "Role of Anion-binding Sites in cytoplasmic and extracellular channels of *Natronomonas pharaonis* halorhodopsin," Biochemistry, 2005. vol. 44, pp. 4775-4784.
Sauer "Site-specific recombination: developments and applications," Current Opinion in Biotechnology, 1994, vol. 5, No. 5: pp. 521-527.
Schiff, et al. "Behavioral improvements with thalamic stimulation after severe traumatic brain injury," Nature, 2007, vol. 448, pp. 600-604.
Schlaepfer et al. "Deep Brain stimulation to Reward Circuitry Alleviates Anhedonia in Refractory Major Depresion," Neuropsychopharmacology, 2008,vol. 33, pp. 368-377.
Schroll et al., "Light-induced activation of distinct modulatory neurons triggers appetitive or aversive learning in *Drosophila larvae*", Current Biology, Sep. 2006, 16(17):1741-1747.
Sclimenti, et al. "Directed evolution of a recombinase for improved genomic integration at a native human sequence," Nucleic Acids Research, 2001, vol. 29, No. 24: pp. 5044-5051.
Sheikh et al., "Neurodegenerative Diseases: Multifactorial Conformational Diseases and Their Therapeutic Interventions", Journal of Neurodegenerative Diseases (2013), Article ID 563481:1-8.
Shepherd, et al. "Circuit Analysis of Experience-Dependent Plasticity in the Developing Rat Barrel Cortex", Neuron, 2003, vol. 38: pp. 277-289.
Shibasaki et al., "Effects of body temperature on neural activity in the hippocampus: Regulation of resting membrane potentials by transient receptor potential vanilloid 4," The Journal of Neuroscience, 2007, 27(7):1566-1575.
Shoji, et al.; "Current Status of Delivery Systems to Improve Target Efficacy of Oligonucleotides"; Current Pharmaceutical Design; vol. 10, pp. 785-796 (2004).
Sigmund; "Viewpoint: Are Studies in Genetically Altered Mice Out of Control?"; Arterioscler Thromb Vasc Biol.; vol. 20, No. 6, pp. 1425-1429 (Jun. 2000).
Silver, et al. "Amino terminus of the yeast GAL4 gene product is sufficient for nuclear localization" PNAS, 1984, vol. 81, No. 19: pp. 5951-5955.
Simmons et al. "Localization and function of NK3 subtype Tachykinin receptors of layer pyramidal neurons of the guinea-pig medial prefrontal cortex", Neuroscience, 2008, vol. 156, No. 4: pp. 987-994.
Sineshchekov et al., "Two Rhodopsins Mediate Phototaxis to Low and High Intensity Light in Chlamydomas Reinhardtil", PNAS, 2002, vol. 99, No. 13, pp. 8689-8694.
Sineshchekov et al.; "Intramolecular Proton Transfer in Channelrhodopsins"; Biophysical Journal; vol. 104, No. 4, pp. 807-817 (Feb. 2013).
Singer et al. "Elevated Intrasynaptic Dopamine Release in Tourette's Syndrome Measured by PET," American Journal of Psychiatry, 2002, vol. 159: pp. 1329-1336.
Singer; "Light Switch for Bladder Control"; Technology Review; pp. 1-2 (Sep. 14, 2009).
Skolnick, et al.; "From genes to protein structure and function: novel applications of computational approaches in the genomic era"; Trends Biotechnol; vol. 18, No. 1, pp. 34-39 (Jan. 2000).
Slamovits et al., "A bacterial proteorhodopsin proton pump in marie eukaryotes", Nature Comm, 2011, 2:183.
Slimko et al., "Selective Electrical Silencing of Mammalian Neurons In Vitro by the use of Invertebrate Ligand-Gated Chloride Channels", The Journal of Neuroscience, 2002, vol. 22, No. 17: pp. 7373-7379.
Smith et al. "Diversity in the serine recombinases", Molecular Microbiology, 2002, vol. 44, No. 2: pp. 299-307.
Sohal et al., "Parvalbumin neurons and gamma rhythms enhance cortical circuit performance", Nature, 2009, vol. 459, No. 7247, pp. 698-702.

(56) References Cited

OTHER PUBLICATIONS

Song et al. "Differential Effect of Tea on Long-Term Synaptic Modification in Hippocampal CA1 and Dentate Gyrus in vitro." Neurobiology of Learning and Memory, 2001, vol. 76, No. 3, pp. 375-387.
Song, "Genes responsible for native depolarization-activated K+ currents in neurons," Neuroscience Research, 2002, vol. 42, pp. 7-14.
Soofiyani, et al.; "Gene Therapy, Early Promises, Subsequent Problems, and Recent Breakthroughs"; Advanced Pharmaceutical Bulletin; vol. 3, No. 2, pp. 249-255 (2013).
Stark, et al. "Catalysis by site-specific recombinases," Trends Genet., 1992, vol. 8, No. 12: pp. 432-439.
Stockklausner et al. "A sequence motif responsible for ER export and surface expression of Kir2.0 inward rectifier K+ channels," FEBS Letters, 2001, vol. 493, pp. 129-133.
Stoll, et al. "Phage TP901-I site-specific integrase functions in human cells," Journal of Bacteriology, 2002, vol. 184, No. 13: pp. 3657-3663.
Stonehouse, et al.; "Caffeine Regulates Neuronal Expression of the Dopamine 2 Receptor Gene"; Molecular Pharmacology; vol. 64, No. 6, pp. 1463-1473 (2003).
Suzuki et al., "Stable Transgene Expression from HSV Amplicon Vectors in the Brain: Potential Involvement of Immunoregulatory Signals", Molecular Therapy (2008), 16(10):1727-1736.
Swanson, "Lights, Opsins, Action! Optogenetics Brings Complex Neuronal Circuits into Sharper Focus", 2009, The Dana Foundation, [URL: http://www.dana.org/news/features/detail.aspx?id=24236], PDF File, pp. 1-3.
Swiss-Prot_Q2QCJ4, Opsin 1, Oct. 31, 2006, URL: http://www.ncbi.nlm.nig.gov/protein/Q2QCJ4.
Takahashi, et al."Diversion of the Sign of Phototaxis in a *Chlamydomonas reinhardtii* Mutant Incorporated with Retinal and Its Analogs," FEBS Letters, 1992, vol. 314, No. 3, pp. 275-279.
Takahashi, et al., "Induction of Pluripotent Stem Cells from Mouse Embryonic and Adult Fibroblast Cultures by Defined Factors", 2006, Cell, vol. 126, pp. 663-676.
Tam, B. et al., "Identification of an Outer Segment Targeting Signal in the COOH Terminus of Rhodopsin Using Transgenic *Xenopus laevis*", The Journal of Cell Biology, 2000, vol. 151, No. 7, pp. 1369-1380.
Tamai, "Progress in Pathogenesis and Therapeutic Research in Retinitis Pigmentosa and Age Related Macular Degeneration", Nippon Ganka Gakkai Zasshi, Dec. 2004, 108(12):750-769.
Tatarkiewicz, et al. "Reversal of Hyperglycemia in Mice After Subcutaneous Transplantation of Macroencapsulated Islets", Transplantation, 1999, vol. 67, No. 5: pp. 665-671.
Taurog et al., "HLA-B27 in inbred and non-inbred transgenic mice", J. Immunol., 1988, vol. 141, pp. 4020-4023.
Thomas et al., "Progress and Problems with the Use of Viral Vectors for Gene", Nat. Rev. Genet. (2003), 4(5):346-358.
Tønnesen, et al., "Optogenetic Control of Epileptiform Activity", PNAS, 2009, vol. 106, No. 29, pp. 12162-12167.
Tottene et al., "Familial Hemiplegic Migraine Mutations Increase $Ca^{2+}$ Influx Through Single Human $Ca_v2.1$ Current Density in Neurons", PNAS USA, 2002, vol. 99, No. 20: pp. 13284-13289.
Towne et al., "Efficient transduction of non-human primate motor neurons after intramuscular delivery of recombinant AAV serotype 6", Gene Ther., 2010, 17(1):141-6.
Towne et al., "Optogenetic control of targeted peripheral axons in freely moving animals", PLoS One, 2013, 8(8):e72691.
Towne et al., "Recombinant adeno-associated virus serotype 6 (rAAV2/6)-mediated gene transfer to nociceptive neurons through different routes of delivery", Mol Pain, 2009, 5:52.
Tsai, et al., "Phasic Firing in Dopaminergic Neurons in Sufficient for Behavioral Conditioning", Science, 2009, vol. 324, pp. 1080-1084.
Tsau et al. "Distributed Aspects of the Response to Siphon Touch in Aplysia: Spread of Stimulus Information and Cross-Correlation Analysis," The Journal of Neuroscience, 1994, vol. 14, No. 7, pp. 4167-4184.

Tye et. al., "Amygdala circuitry mediating reversible and bidirectional control of anxiety", Nature, 2011, vol. 471(7338): pp. 358-362.
Tye et. al., Supplementary Materials: "Amygdala circuitry mediating reversible and bidirectional control of anxiety,", Nature, 2011, vol. 471(7338): pp. 358-362.
Tye, et al. "Optogenetic investigation of neural circuits underlyding brain disease in animal models," Nature Reviews Neuroscience (Mar. 2012), 13(4):251-266.
Ulmanen, et al. "Transcription and translation of foreign genes in *Bacillus subtilis* by the aid of a secretion vector," Journal of Bacteriology, 1985, vol. 162, No. 1: pp. 176-182.
Van Der Linden, "Functional brain imaging and pharmacotherapy in social phobia: single photon emission computed tomography before and after Treatment with the selective serotonin reuptake inhibitor citalopram," Prog Neuro-psychopharmacol Biol Psychiatry, 2000, vol. 24, No. 3: pp. 419-438.
Vanin, et al. "Development of high-titer retroviral producer cell lines by using Cre-mediated recombination," Journal of Virology, 1997, vol. 71, No. 10: pp. 7820-7826.
Varo et al.,"Light-Driven Chloride Ion Transport by Halorhodopsin from Natronobacterium pharaonis. 2. Chloride Release and Uptake, Protein Conformation Change, and Thermodynamics", Biochemistry (1995), 34(44):14500-14507.
Verma, et al.; "Gene therapy—promises, problems and prospects"; Nature; vol. 389, pp. 239-242 (Sep. 1997).
Vetter, et al. "Development of a Microscale Implantable Neural Interface (MINI) Probe System," Proceedings of the 2005 IEEE, Engineering in Medicine and Biology 27th Annual Conference, Shanghai, China, Sep. 1-4, 2005.
Wagner, "Noninvasive Human Brain Stimulation", Annual Rev. Biomed. Eng. 2007. 9:I9,I-19.39.
Wall, "Transgenic livestock: Progress and prospects for the future", Theriogenology, 1996, vol. 45, pp. 57-68.
Wang, et al. "Direct-current Nanogenerator Driven by Ultrasonic Waves," Science, 2007, vol. 316, pp. 102-105.
Wang, et al., "High-speed mapping of synaptic connectivity using photostimulation in Channelrhodopsin-2 transgenic mice", PNAS, 2007, vol. 104, No. 19, pp. 8143-8148.
Wang, et al., "Molecular Determinants Differentiating Photocurrent Properties of Two Channelrhodopsins from Chlamydomonas", 2009, The Journal of Biological Chemistry, vol. 284, No. 9, pp. 5685-5696.
Wang, et al., "Mrgprd-Expressing Polymodal Nociceptive Neurons Innervate Most Known Classes of Substantia Gelatinosa Neurons", J Neurosci, 2009, 29(42):13202-13209.
Wang, et al.; "Laser-evoked synaptic transmission in cultured hippocampal neurons expressing channelrhodopsin-2 delivered by adeno-associated virus"; Journal of Neuroscience Methods; vol. 183, pp. 165-175 (2009).
Wang, et al.; "Simultaneous phase and size control of upconversion nanocrystals through lanthanide doping"; Nature; vol. 463, No. 7284, pp. 1061-1065 (Feb. 25, 2010).
Ward, et al. "Construction and characterisation of a series of multi-copy promoter-probe plasmid vectors for *Streptomyces* using the aminoglycoside phosphotransferase gene from Tn5 as indicator", 1986, Mol. Gen. Genet., vol. 203: pp. 468-478.
Watson, et al. "Targeted transduction patterns in the mouse brain by lentivirus vectors pseudotyped with VSV, Ebola, Mokola, LCMV, or MuLV envelope proteins," Molecular Therapy, 2002, vol. 5, No. 5, pp. 528-537.
Weick et al. "Interactions with PDZ Proteins Are Required for L-Type Calcium Channels to Activate cAMP Response Element-Binding Protein-Dependent Gene Expression," The Journal of Neuroscience, 2003, vol. 23, No. 8, pp. 3446-3456.
Wells et al. "Application of Infrared light for in vivo neural stimulation," Journal of Biomedical Optics, 2005, vol. 10(6), pp. 064003-1-064003-12.
Williams et al., "From optogenetic technologies to neuromodulation therapies", Sci Transl Med., 2013, 5(177):177.
Witten et. al., "Cholinergic Interneurons Control Local Circuit Activity and Cocaine Conditioning", Science, 2010, vol. 330, No. 6011: pp. 1677-1681.

(56) References Cited

OTHER PUBLICATIONS

Witten et. al., Supporting Online Material for: "Cholinergic Interneurons Control Local Circuit Activity and Cocaine Conditioning", Science, 2010, vol. 330: 17 pages.
Written opinion of PCT Application No. PCT/US2011/059383 (dated May 9, 2012).
Xiong et al., "Interregional connectivity to primary motor cortex revealed using MRI resting state images", Hum Brain Mapp, 1999, 8(2-3):151-156.
Yajima, et al., "Effects of bromazepam on responses of mucosal blood flow of the gastrointestinal tract and the gastric motility to stimulation of the amygdala and hypothalamus in conscious cats"; Folia Pharmacol. Japon; vol. 83, No. 3, pp. 237-248 (Mar. 1984). [English abstract translation].
Yamada, Shigeto; "Neurobiological Aspects of Anxiety Disorders"; The Japanese Journal of Psychiatry; vol. 8, No. 6, pp. 525-535 (Nov. 25, 2003). [English translation of introduction and summary].
Yamazoe, et al. "Efficient generation of dopaminergic neurons from mouse embryonic stem cells enclosed in hollow fibers", Biomaterials, 2006, vol. 27, pp. 4871-4880.
Yan et al., "Cloning and Characterization of a Human β,β-Carotene-15, 15'-Dioxygenase that is Highly Expressed in the Retinal Pigment Epithelium", Genomics, 2001, vol. 72: pp. 193-202.
Yizhar et al., "Optogenetics in neural systems", Neuron Primer, vol. 71, No. 1, pp. 9-34 (Jul. 14, 2011).
Yizhar et. al., "Neocortical excitation/inhibition balance in information processing and social dysfunction", Nature, 2011, vol. 477, pp. 171-178; and Supplemental Materials; 41 pages.
Yoon, et al., "A micromachined silicon depth probe for multichannel neural recording," IEEE Transactions Biomedical Engineering, 2000, vol. 47, No. 8, pp. 1082-1087.
Yoshimura, et al. "Excitatory cortical neurons form fine-scale functional networks", Nature, 2005, vol. 433: pp. 868-873.
Zacharias et al. "Recent advances in technology for measuring and manipulating cell signals," Current Opinion in Neurobiology, 2000, vol. 10: pp. 416-421.
Zemelman, et al. "Selective Photostimulation of Genetically ChARGed Neurons", Neuron, 2002, vol. 33: pp. 15-22.
Zemelman, et al. "Photochemical gating of heterologous ion channels: Remote control over genetically designated populations of neurons", PNAS, 2003, vol. 100, No. 3: pp. 1352-1357.
Zhang "Multimodal fast optical interrogation of neural circuitry," Nature, 2007, vol. 446, pp. 633-641.
Zhang, et al. "Channelrhodopsin-2 and optical control of excitable cells," Nature Methods,2006, vol. 3, No. 10, pp. 785-792.
Zhang, et al. "Red-Shifted Optogenetic Excitation: a Tool for Fast Neural Control Derived from *Volvox carteri*", Nature Neurosciences, 2008,vol. 11, No. 6, pp. 631-633.
Zhang, et al., "The Microbial Opsin Family of Optogenetic Tools", Cell, 2011, vol. 147, No. 7, pp. 1146-1457.
Zhang, et al.; "Optogenetic interrogation of neural circuits: Technology for probing mammalian brain structures"; Nature Protocols; vol. 5, No. 3, pp. 439-456 (Feb. 18, 2010).
Zhao, et al., "Improved Expression of Halorhodopsin for Light-Induced Silencing of Neuronal Activity", Brain Cell Biology, 2008, vol. 36 (1-4), pp. 141-154.
Zrenner, E., "Will Retinal Implants Restore Vision?" Science, 2002, vol. 295, No. 5557, pp. 1022-1025.
Zufferey, et al. "Self-Inactivating Lentivirus Vector for Safe and Efficient In Vivo Gene Delivery", Journal of Virology, 1998, vol. 72, No. 12, pp. 9873-9880.
Jones, et al.; "Animal Models of Schizophrenia"; British Journal of Pharmacology; vol. 164, pp. 1162-1194 (2011).
Gritton, et al.; "Optogenetically-evoked cortical cholinergic transients in mice expressing channelrhodopsin-2 (ChR2) in cholinergic neurons"; Society for Neuroscience Abstract Viewer and Itinery Planner & 40th Annual Meeting of the Society-for-Neuroscience; vol. 40, 2 pages (2010).
Sofuoglu, et al.; "Cholinergic Functioning in Stimulant Addiction: Implications for Medications Development"; CNS Drugs; vol. 23, No. 11, pp. 939-952 (Nov. 1, 2009).
Witten, et al.; "Cholinergic interneurons of the nucleus accumbens control local circuit activity and reward behavior"; Society for Neuroscience Abstract Viewer and Itinerary Planner & 40th Annual Meeting of the Society-for-Neuroscience; vol. 40, 2 pages (2010).
Definition of integral. Merriam-Webster Dictionary, retrieved on Mar. 20, 2017; Retrieved from the internet: <http://www.merriam-webster.com/dictionary/integral>.
Co-pending U.S. Appl. No. 14/886,763, filed Oct. 19, 2015.
Co-pending U.S. Appl. No. 14/911,405, filed Feb. 26, 2016.
Co-pending U.S. Appl. No. 15/008,214, filed Jan. 27, 2016.
Co-pending U.S. Appl. No. 15/059,159, filed Mar. 2, 2016.
Co-pending U.S. Appl. No. 15/095,519, filed Apr. 11, 2016.
Co-pending U.S. Appl. No. 15/097,925, filed Apr. 13, 2016.
Co-pending U.S. Appl. No. 15/147,772, filed May 5, 2016.
Co-pending U.S. Appl. No. 15/153,299, filed May 12, 2016.
Co-pending U.S. Appl. No. 15/153,305, filed May 12, 2016.
Co-pending U.S. Appl. No. 15/156,124, filed May 16, 2016.
Lin, et al.; "Study of the Circuitry of Nucleus Accumbens and its Effect on Addiction by Optogenetic Methods: 964"; Neurosurgery; vol. 67, No. 2, pp. 557 (Aug. 2010).
Tsuchida; "Nervous Control of Micturition"; The Japanese Journal of Urology; vol. 80, No. 9, pp. 1257-1277 (1989).
Definition of Implant; Merriam-Webster Dictionary; retrieved Nov. 7, 2016 (http://www.merriam-webster.com/dictionary/implant).
Ferenczi, et al.; "Optogenetic approaches addressing extracellular modulation of neural excitability"; Scientific Reports; vol. 6, 20 pages (Apr. 5, 2016).
Li, et al.; "A Method for Activiation of Endogenous Acid-sensing Ion Channel 1a (ASIC1a) in the Nervous System with High Spatial and Temporal Precision"; The Journal of Biological Chemistry; vol. 289, No. 22, pp. 15441-15448 (May 30, 2014).
Shimizu, et al.; "NMDA Receptor-Dependent Synaptic Reinforcement as a Crucial Process for Memory Consolidation"; Science; vol. 290, pp. 1170-1174 (Nov. 10, 2000).
Zeng, et al.; "Activation of acid-sensing ion channels by localized proton transient reveals their role in proton signaling"; Scientific Reports; vol. 5, 14 pages (Sep. 15, 2015).
Zeng, et al.; "Proton production, regulation and pathophysiological roles in the mammalian brain"; Neuroscience Bulletin; vol. 28, No. 1, pp. 1-13 (Feb. 1, 2012).
Davidson, et al.; "Viral Vectors for Gene Delivery to the Nervous System"; Nature Reviews Neuroscience; vol. 4, pp. 353-364 (May 2003).
Fanselow, et al.; "Why We Think Plasticity Underlying Pavlovian Fear Conditioning Occurs in the Basolateral Amygdala"; Neuron; vol. 23, pp. 229-232 (Jun. 1999).
Rogers, et al.; "Effects of ventral and dorsal CA1 subregional lesions on trace fear conditioning"; Neurobiology of Learning and Memory; vol. 86, pp. 72-81 (2006).
Chow, et al.; "High-performance genetically targetable optical neural silencing by light-driven proton pumps"; Nature; vol. 463, pp. 98-102 (Jan. 7, 2010).
Gong, et al.; "Enhanced Archaerhodopsin Fluorescent Protein Voltage Indicators"; PLOS One; vol. 8, Issue 6, 10 pages (Jun. 2013).
Han, et al.; "A high-light sensitivity optical neural silencer: development and application to optogenetic control of non-human primate cortex"; Frontiers in Systems Neuroscience; vol. 5, Article 18, pp. 1-8 (Apr. 2011).
Abbott, et al.; "Photostimulation of Retrotrapezoid Nucleus Phox2b-Expressing Neurons In Vivo Produces Long-Lasting Activation of Breathing in Rats"; The Journal of Neuroscience; vol. 29, No. 18, pp. 5806-5819 (May 6, 2009).
Alilain, et al.; "Light-Induced Rescue of Breathing after Spinal Cord Injury"; The Journal of Neuroscience; vol. 28, No. 46, pp. 11862-11870 (Nov. 12, 2008).
Cardin, et al.; "Targeted optogenetic stimulation and recording of neurons in vivo using cell-type-specific expression of Channelrhodopsin-2"; Nature Protocols; vol. 5, No. 2, pp. 247-254 (2010).

(56) References Cited

OTHER PUBLICATIONS

Caro, et al.; "Engineering of an Artificial Light-Modulated Potassium Channel"; PLoS One; vol. 7, Issue 8, e43766 (Aug. 2012).
Coleman, et al.; "Assessing Anxiety in Nonhuman Primates"; Ilar Journal; vol. 55, No. 2, pp. 333-346 (2014).
Hagglund, et al.; "Activation of groups of excitatory neurons in the mammalian spinal cord or hindbrain evokes locomotion"; Nature Neuroscience; vol. 13, No. 2, 8 pages (Feb. 2010).
Kleinlogel, et al.; "A gene-fusion strategy for stoichiometric and co-localized expression of light-gated membrane proteins"; Nature Methods; vol. 8, No. 12, pp. 1083-1091 (Dec. 2011).
Kravitz, et al.; "Regulation of parkinsonian motor behaviours by optogenetic control of basal ganglia circuitry"; Nature; vol. 466, No. 622, 8 pages (Jul. 29, 2010).
Luo, et al.; "Synthetic DNA delivery systems"; Nature Biotechnology; vol. 18, pp. 33-37 (Jan. 2000).
Maestripieri, et al.; "A modest proposal: displacement activities as an indicator of emotions in primates"; Anim. Behav.; vol. 44, pp. 967-979 (1992).
Nelson, et al.; "Non-Human Primates: Model Animals for Developmental Psychopathology"; Neuropsychopharmacology; vol. 34, No. 1, pp. 90-105 (Jan. 2009).
Tomita, et al.; "Visual Properties of Transgenic Rats Harboring the Channelrhodopsin-2 Gene Regulated by the Thy-1.2 Promoter"; PLoS One; vol. 4, No. 11, 13 pages (Nov. 2009).
Uniprot Accession No. P02945, integrated into the database on Jul. 21, 1986.
Azizgolshani, et al.; "Reconstituted plant viral capsids can release genes to mammalian cells"; Virology; vol. 441, No. 1, pp. 12-17 (2013).
Racaniello; "How many viruses on Earth?"; Virology Blog; 6 pages; http://www.virology.ws/2013/09/06/how-many-viruses-on-earth/ (Sep. 6, 2013).
Gerits, et al.; "Optogenetically Induced Behavioral and Functional Network Changes in Primates"; Current Biology; vol. 22, pp. 1722-1726 (Sep. 25, 2012).
Han, et al.; "Optogenetics in the nonhuman primate"; Prog. Brain Res.; vol. 196, pp. 215-233 (2012).

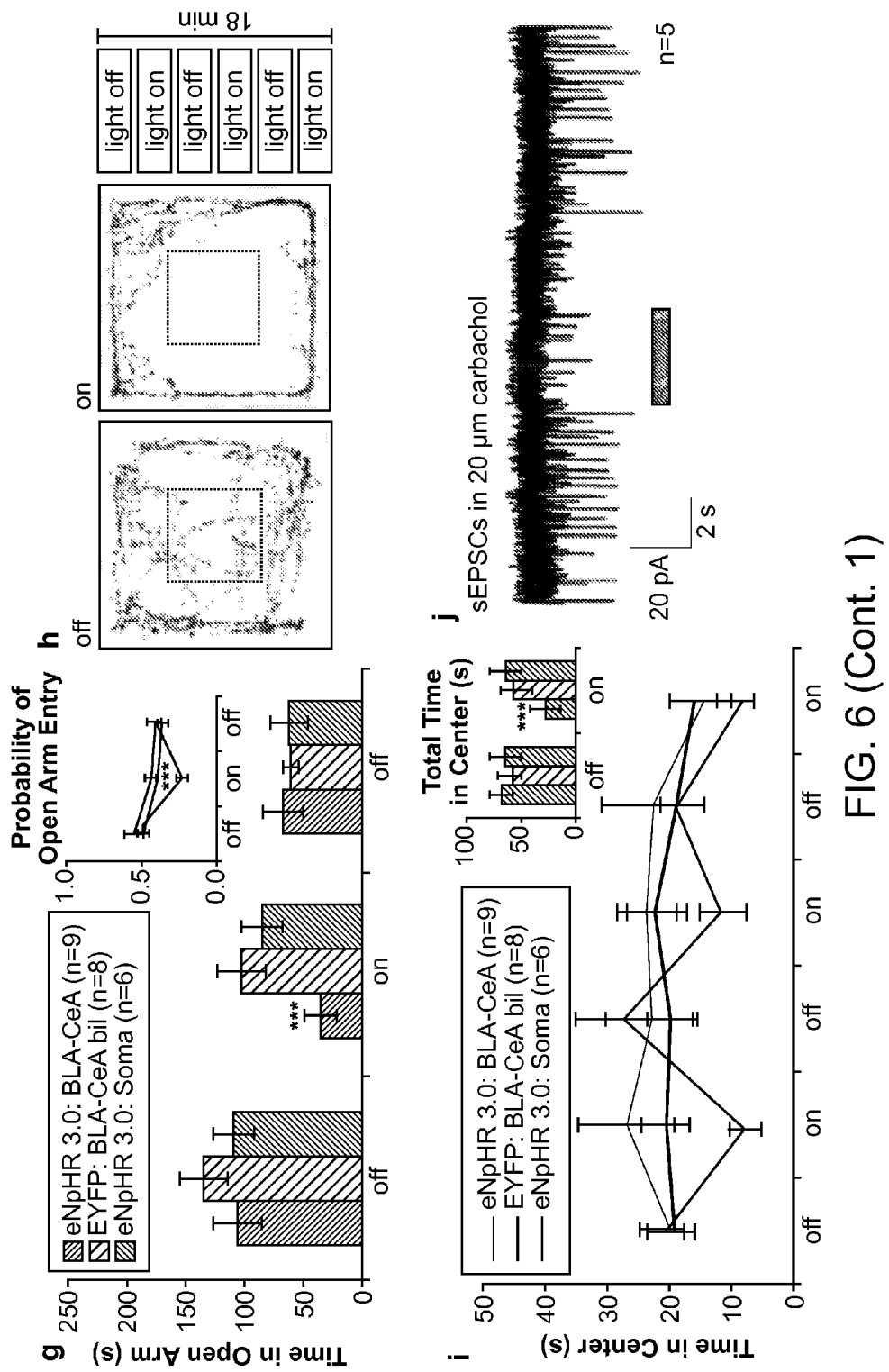
FIG. 6 (Cont. 1)

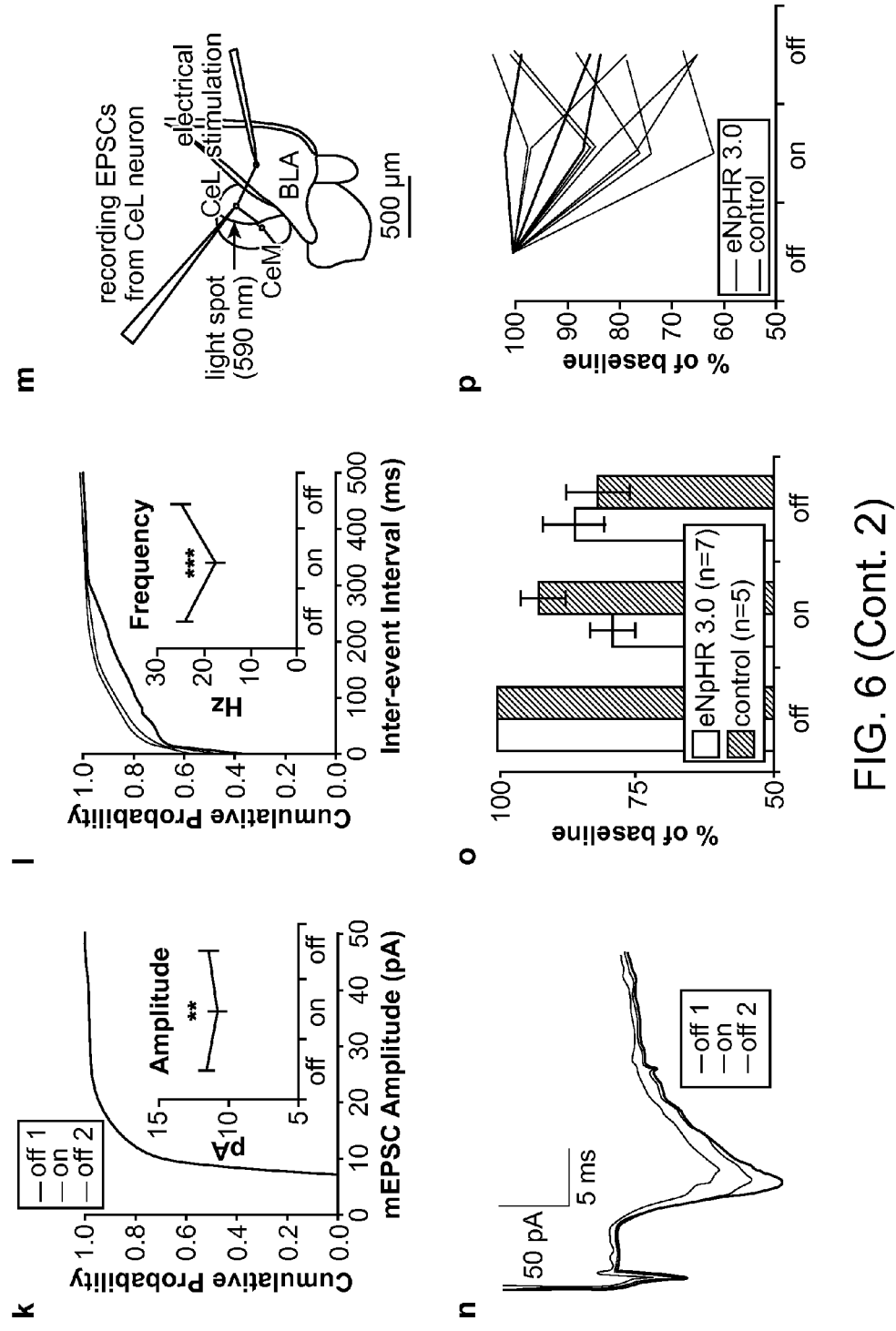
FIG. 6 (Cont. 2)

SEQUENCE LISTING

<160> NUMBER OF SEQ ID NOS: 14

<210> SEQ ID NO 1
<211> LENGTH: 273
<212> TYPE: PRT
<213> ORGANISM: Natronomonas pharaonis

<400> SEQUENCE: 1

Val Thr Gln Arg Glu Leu Phe Glu Phe Val Leu Asn Asp Pro Leu Leu
1               5                   10                  15

Ala Ser Ser Leu Tyr Ile Asn Ile Ala Leu Ala Gly Leu Ser Ile Leu
            20                  25                  30

Leu Phe Val Phe Met Thr Arg Gly Leu Asp Asp Pro Arg Ala Lys Leu
        35                  40                  45

Ile Ala Val Ser Thr Ile Leu Val Pro Val Val Ser Ile Ala Ser Tyr
50                  55                  60

Thr Gly Leu Ala Ser Gly Leu Thr Ile Ser Val Leu Glu Met Pro Ala
65                  70                  75                  80

Gly His Phe Ala Glu Gly Ser Ser Val Met Leu Gly Gly Glu Glu Val
                85                  90                  95

Asp Gly Val Val Thr Met Trp Gly Arg Tyr Leu Thr Trp Ala Leu Ser
            100                 105                 110

Thr Pro Met Ile Leu Leu Ala Leu Gly Leu Leu Ala Gly Ser Asn Ala
        115                 120                 125

Thr Lys Leu Phe Thr Ala Ile Thr Phe Asp Ile Ala Met Cys Val Thr
        130                 135                 140

Gly Leu Ala Ala Ala Leu Thr Thr Ser Ser His Leu Met Arg Trp Phe
145                 150                 155                 160

Trp Tyr Ala Ile Ser Cys Ala Cys Phe Leu Val Val Leu Tyr Ile Leu
                165                 170                 175

Leu Val Glu Trp Ala Gln Asp Ala Lys Ala Ala Gly Thr Ala Asp Met
            180                 185                 190

Phe Asn Thr Leu Lys Leu Leu Thr Val Val Met Trp Leu Gly Tyr Pro
        195                 200                 205

Ile Val Trp Ala Leu Gly Val Glu Gly Ile Ala Val Leu Pro Val Gly
            210                 215                 220

Val Thr Ser Trp Gly Tyr Ser Phe Leu Asp Ile Val Ala Lys Tyr Ile
225                 230                 235                 240

Phe Ala Phe Leu Leu Leu Asn Tyr Leu Thr Ser Asn Glu Ser Val Val
                245                 250                 255

Ser Gly Ser Ile Leu Asp Val Pro Ser Ala Ser Gly Thr Pro Ala Asp
            260                 265                 270

Asp

<210> SEQ ID NO 2
<211> LENGTH: 559
<212> TYPE: PRT
<213> ORGANISM: Artificial Sequence
<220> FEATURE:
<223> OTHER INFORMATION: Synthetic polypeptide

<400> SEQUENCE: 2

Met Thr Glu Thr Leu Pro Pro Val Thr Glu Ser Ala Val Ala Leu Gln
1               5                   10                  15

Ala Glu Val Thr Gln Arg Glu Leu Phe Glu Phe Val Leu Asn Asp Pro
            20                  25                  30

Leu Leu Ala Ser Ser Leu Tyr Ile Asn Ile Ala Leu Ala Gly Leu Ser
        35                  40                  45

Ile Leu Leu Phe Val Phe Met Thr Arg Gly Leu Asp Asp Pro Arg Ala
50                  55                  60

Lys Leu Ile Ala Val Ser Thr Ile Leu Val Pro Val Val Ser Ile Ala
65                  70                  75                  80

```
Ser Tyr Thr Gly Leu Ala Ser Gly Leu Thr Ile Ser Val Leu Glu Met
             85                  90                  95

Pro Ala Gly His Phe Ala Glu Gly Ser Ser Val Met Leu Gly Gly Glu
            100                 105                 110

Glu Val Asp Gly Val Val Thr Met Trp Gly Arg Tyr Leu Thr Trp Ala
            115                 120                 125

Leu Ser Thr Pro Met Ile Leu Ala Leu Gly Leu Leu Ala Gly Ser
130                 135                 140

Asn Ala Thr Lys Leu Phe Thr Ala Ile Thr Phe Asp Ile Ala Met Cys
145                 150                 155                 160

Val Thr Gly Leu Ala Ala Leu Thr Thr Ser Ser His Leu Met Arg
            165                 170                 175

Trp Phe Trp Tyr Ala Ile Ser Cys Ala Cys Phe Leu Val Val Leu Tyr
            180                 185                 190

Ile Leu Leu Val Glu Trp Ala Gln Asp Ala Lys Ala Ala Gly Thr Ala
            195                 200                 205

Asp Met Phe Asn Thr Leu Lys Leu Leu Thr Val Met Trp Leu Gly
            210                 215                 220

Tyr Pro Ile Val Trp Ala Leu Gly Val Glu Gly Ile Ala Val Leu Pro
225                 230                 235                 240

Val Gly Val Thr Ser Trp Gly Tyr Ser Phe Leu Asp Ile Val Ala Lys
            245                 250                 255

Tyr Ile Phe Ala Phe Leu Leu Leu Asn Tyr Leu Thr Ser Asn Glu Ser
            260                 265                 270

Val Val Ser Gly Ser Ile Leu Asp Val Pro Ser Ala Ser Gly Thr Pro
            275                 280                 285

Ala Asp Asp Ala Ala Ala Lys Ser Arg Ile Thr Ser Glu Gly Glu Tyr
            290                 295                 300

Ile Pro Leu Asp Gln Ile Asp Ile Asn Val Val Ser Lys Gly Glu Glu
305                 310                 315                 320

Leu Phe Thr Gly Val Val Pro Ile Leu Val Glu Leu Asp Gly Asp Val
            325                 330                 335

Asn Gly His Lys Phe Ser Val Ser Gly Glu Gly Glu Gly Asp Ala Thr
            340                 345                 350

Tyr Gly Lys Leu Thr Leu Lys Phe Ile Cys Thr Thr Gly Lys Leu Pro
            355                 360                 365

Val Pro Trp Pro Thr Leu Val Thr Thr Phe Gly Tyr Gly Leu Gln Cys
            370                 375                 380

Phe Ala Arg Tyr Pro Asp His Met Lys Gln His Asp Phe Phe Lys Ser
385                 390                 395                 400

Ala Met Pro Glu Gly Tyr Val Gln Glu Arg Thr Ile Phe Phe Lys Asp
            405                 410                 415

Asp Gly Asn Tyr Lys Thr Arg Ala Glu Val Lys Phe Glu Gly Asp Thr
            420                 425                 430

Leu Val Asn Arg Ile Glu Leu Lys Gly Ile Asp Phe Lys Glu Asp Gly
            435                 440                 445

Asn Ile Leu Gly His Lys Leu Glu Tyr Asn Tyr Asn Ser His Asn Val
450                 455                 460

Tyr Ile Met Ala Asp Lys Gln Lys Asn Gly Ile Lys Val Asn Phe Lys
465                 470                 475                 480

Ile Arg His Asn Ile Glu Asp Gly Ser Val Gln Leu Ala Asp His Tyr
            485                 490                 495

Gln Gln Asn Thr Pro Ile Gly Asp Gly Pro Val Leu Leu Pro Asp Asn
```

```
                    500                 505                 510
His Tyr Leu Ser Tyr Gln Ser Ala Leu Ser Lys Asp Pro Asn Glu Lys
            515                 520                 525

Arg Asp His Met Val Leu Leu Glu Phe Val Thr Ala Ala Gly Ile Thr
        530                 535                 540

Leu Gly Met Asp Glu Leu Tyr Lys Phe Cys Tyr Glu Asn Glu Val
545                 550                 555

<210> SEQ ID NO 3
<211> LENGTH: 542
<212> TYPE: PRT
<213> ORGANISM: Artificial Sequence
<220> FEATURE:
<223> OTHER INFORMATION: Synthetic polypeptide

<400> SEQUENCE: 3

Met Val Thr Gln Arg Glu Leu Phe Glu Phe Val Leu Asn Asp Pro Leu
1               5                   10                  15

Leu Ala Ser Ser Leu Tyr Ile Asn Ile Ala Leu Ala Gly Leu Ser Ile
            20                  25                  30

Leu Leu Phe Val Phe Met Thr Arg Gly Leu Asp Asp Pro Arg Ala Lys
        35                  40                  45

Leu Ile Ala Val Ser Thr Ile Leu Val Pro Val Val Ser Ile Ala Ser
    50                  55                  60

Tyr Thr Gly Leu Ala Ser Gly Leu Thr Ile Ser Val Leu Glu Met Pro
65                  70                  75                  80

Ala Gly His Phe Ala Glu Gly Ser Ser Val Met Leu Gly Gly Glu Glu
                85                  90                  95

Val Asp Gly Val Val Thr Met Trp Gly Arg Tyr Leu Thr Trp Ala Leu
            100                 105                 110

Ser Thr Pro Met Ile Leu Leu Ala Leu Gly Leu Leu Ala Gly Ser Asn
        115                 120                 125

Ala Thr Lys Leu Phe Thr Ala Ile Thr Phe Asp Ile Ala Met Cys Val
    130                 135                 140

Thr Gly Leu Ala Ala Ala Leu Thr Thr Ser Ser His Leu Met Arg Trp
145                 150                 155                 160

Phe Trp Tyr Ala Ile Ser Cys Ala Cys Phe Leu Val Val Leu Tyr Ile
                165                 170                 175

Leu Leu Val Glu Trp Ala Gln Asp Ala Lys Ala Ala Gly Thr Ala Asp
            180                 185                 190

Met Phe Asn Thr Leu Lys Leu Leu Thr Val Val Met Trp Leu Gly Tyr
        195                 200                 205

Pro Ile Val Trp Ala Leu Gly Val Glu Gly Ile Ala Val Leu Pro Val
    210                 215                 220

Gly Val Thr Ser Trp Gly Tyr Ser Phe Leu Asp Ile Val Ala Lys Tyr
225                 230                 235                 240

Ile Phe Ala Phe Leu Leu Leu Asn Tyr Leu Thr Ser Asn Glu Ser Val
                245                 250                 255

Val Ser Gly Ser Ile Leu Asp Val Pro Ser Ala Ser Gly Thr Pro Ala
            260                 265                 270

Asp Asp Ala Ala Ala Lys Ser Arg Ile Thr Ser Glu Gly Glu Tyr Ile
        275                 280                 285

Pro Leu Asp Gln Ile Asp Ile Asn Val Val Ser Lys Gly Glu Glu Leu
    290                 295                 300

Phe Thr Gly Val Val Pro Ile Leu Val Glu Leu Asp Gly Asp Val Asn
```

```
                305                 310                 315                 320
Gly His Lys Phe Ser Val Ser Gly Glu Gly Glu Gly Asp Ala Thr Tyr
                    325                 330                 335
Gly Lys Leu Thr Leu Lys Phe Ile Cys Thr Thr Gly Lys Leu Pro Val
                    340                 345                 350
Pro Trp Pro Thr Leu Val Thr Thr Phe Gly Tyr Gly Leu Gln Cys Phe
                    355                 360                 365
Ala Arg Tyr Pro Asp His Met Lys Gln His Asp Phe Phe Lys Ser Ala
                    370                 375                 380
Met Pro Glu Gly Tyr Val Gln Glu Arg Thr Ile Phe Phe Lys Asp Asp
385                 390                 395                 400
Gly Asn Tyr Lys Thr Arg Ala Glu Val Lys Phe Glu Gly Asp Thr Leu
                    405                 410                 415
Val Asn Arg Ile Glu Leu Lys Gly Ile Asp Phe Lys Glu Asp Gly Asn
                    420                 425                 430
Ile Leu Gly His Lys Leu Glu Tyr Asn Tyr Asn Ser His Asn Val Tyr
                    435                 440                 445
Ile Met Ala Asp Lys Gln Lys Asn Gly Ile Lys Val Asn Phe Lys Ile
                    450                 455                 460
Arg His Asn Ile Glu Asp Gly Ser Val Gln Leu Ala Asp His Tyr Gln
465                 470                 475                 480
Gln Asn Thr Pro Ile Gly Asp Gly Pro Val Leu Leu Pro Asp Asn His
                    485                 490                 495
Tyr Leu Ser Tyr Gln Ser Ala Leu Ser Lys Asp Pro Asn Glu Lys Arg
                    500                 505                 510
Asp His Met Val Leu Leu Glu Phe Val Thr Ala Ala Gly Ile Thr Leu
                    515                 520                 525
Gly Met Asp Glu Leu Tyr Lys Phe Cys Tyr Glu Asn Glu Val
                    530                 535                 540

<210> SEQ ID NO 4
<211> LENGTH: 223
<212> TYPE: PRT
<213> ORGANISM: Guillardia theta

<400> SEQUENCE: 4

Ala Ser Ser Phe Gly Lys Ala Leu Leu Glu Phe Val Phe Ile Val Phe
1                   5                   10                  15
Ala Cys Ile Thr Leu Leu Leu Gly Ile Asn Ala Ala Lys Ser Lys Ala
                    20                  25                  30
Ala Ser Arg Val Leu Phe Pro Ala Thr Phe Val Thr Gly Ile Ala Ser
                    35                  40                  45
Ile Ala Tyr Phe Ser Met Ala Ser Gly Gly Gly Trp Val Ile Ala Pro
                    50                  55                  60
Asp Cys Arg Gln Leu Phe Val Ala Arg Tyr Leu Asp Trp Leu Ile Thr
65                  70                  75                  80
Thr Pro Leu Leu Leu Ile Asp Leu Gly Leu Val Ala Gly Val Ser Arg
                    85                  90                  95
Trp Asp Ile Met Ala Leu Cys Leu Ser Asp Val Leu Met Ile Ala Thr
                    100                 105                 110
Gly Ala Phe Gly Ser Leu Thr Val Gly Asn Val Lys Trp Val Trp Trp
                    115                 120                 125
Phe Phe Gly Met Cys Trp Phe Leu His Ile Ile Phe Ala Leu Gly Lys
                    130                 135                 140
```

Ser Trp Ala Glu Ala Ala Lys Ala Lys Gly Gly Asp Ser Ala Ser Val
145                 150                 155                 160

Tyr Ser Lys Ile Ala Gly Ile Thr Val Ile Thr Trp Phe Cys Tyr Pro
                165                 170                 175

Val Val Trp Val Phe Ala Glu Gly Phe Gly Asn Phe Ser Val Thr Phe
            180                 185                 190

Glu Val Leu Ile Tyr Gly Val Leu Asp Val Ile Ser Lys Ala Val Phe
        195                 200                 205

Gly Leu Ile Leu Met Ser Gly Ala Ala Thr Gly Tyr Glu Ser Ile
    210                 215                 220

<210> SEQ ID NO 5
<211> LENGTH: 310
<212> TYPE: PRT
<213> ORGANISM: Artificial Sequence
<220> FEATURE:
<223> OTHER INFORMATION: Synthetic polypeptide

<400> SEQUENCE: 5

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
        35                  40                  45

Gln Thr Ala Ser Asn Val Leu Gln Trp Leu Ala Ala Gly Phe Ser Ile
    50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Cys
        115                 120                 125

Pro Val Ile Leu Ile His Leu Ser Asn Leu Thr Gly Leu Ser Asn Asp
    130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
290                 295                 300

Glu Ala Gly Ala Val Pro
305                 310

<210> SEQ ID NO 6
<211> LENGTH: 310
<212> TYPE: PRT
<213> ORGANISM: Artificial Sequence
<220> FEATURE:
<223> OTHER INFORMATION: Synthetic polypeptide

<400> SEQUENCE: 6

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
    20                  25                  30

Gln Cys Tyr Cys Ala Gly Trp Ile Glu Ser Arg Gly Thr Asn Gly Ala
            35                  40                  45

Gln Thr Ala Ser Asn Val Leu Gln Trp Leu Ala Ala Gly Phe Ser Ile
50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Ser
            115                 120                 125

Pro Val Ile Leu Ile His Leu Ser Asn Leu Thr Gly Leu Ser Asn Asp
130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
290                 295                 300

Glu Ala Gly Ala Val Pro
305                 310

<210> SEQ ID NO 7
<211> LENGTH: 310

<212> TYPE: PRT
<213> ORGANISM: Artificial Sequence
<220> FEATURE:
<223> OTHER INFORMATION: Synthetic polypeptide

<400> SEQUENCE: 7

```
Met Asp Tyr Gly Gly Ala Leu Ser Ala Val Gly Arg Glu Leu Leu Phe
 1               5                  10                  15
Val Thr Asn Pro Val Val Asn Gly Ser Val Leu Val Pro Glu Asp
             20                  25                  30
Gln Cys Tyr Cys Ala Gly Trp Ile Glu Ser Arg Gly Thr Asn Gly Ala
             35                  40                  45
Gln Thr Ala Ser Asn Val Leu Gln Trp Leu Ala Ala Gly Phe Ser Ile
         50                  55                  60
Leu Leu Leu Met Phe Tyr Ala Tyr Gln Thr Trp Lys Ser Thr Cys Gly
 65                  70                  75                  80
Trp Glu Glu Ile Tyr Val Cys Ala Ile Glu Met Val Lys Val Ile Leu
                 85                  90                  95
Glu Phe Phe Phe Glu Phe Lys Asn Pro Ser Met Leu Tyr Leu Ala Thr
            100                 105                 110
Gly His Arg Val Gln Trp Leu Arg Tyr Ala Glu Trp Leu Leu Thr Ser
        115                 120                 125
Pro Val Ile Leu Ile His Leu Ser Asn Leu Thr Gly Leu Ser Asn Asp
    130                 135                 140
Tyr Ser Arg Arg Thr Met Gly Leu Leu Val Ser Ala Ile Gly Thr Ile
145                 150                 155                 160
Val Trp Gly Ala Thr Ser Ala Met Ala Thr Gly Tyr Val Lys Val Ile
                165                 170                 175
Phe Phe Cys Leu Gly Leu Cys Tyr Gly Ala Asn Thr Phe Phe His Ala
            180                 185                 190
Ala Lys Ala Tyr Ile Glu Gly Tyr His Thr Val Pro Lys Gly Arg Cys
        195                 200                 205
Arg Gln Val Val Thr Gly Met Ala Trp Leu Phe Phe Val Ser Trp Gly
    210                 215                 220
Met Phe Pro Ile Leu Phe Ile Leu Gly Pro Glu Gly Phe Gly Val Leu
225                 230                 235                 240
Ser Val Tyr Gly Ser Thr Val Gly His Thr Ile Ile Asp Leu Met Ser
                245                 250                 255
Lys Asn Cys Trp Gly Leu Leu Gly His Tyr Leu Arg Val Leu Ile His
            260                 265                 270
Glu His Ile Leu Ile His Gly Asp Ile Arg Lys Thr Thr Lys Leu Asn
        275                 280                 285
Ile Gly Gly Thr Glu Ile Glu Val Glu Thr Leu Val Glu Asp Glu Ala
    290                 295                 300
Glu Ala Gly Ala Val Pro
305                 310
```

<210> SEQ ID NO 8
<211> LENGTH: 344
<212> TYPE: PRT
<213> ORGANISM: Artificial Sequence
<220> FEATURE:
<223> OTHER INFORMATION: Synthetic polypeptide

<400> SEQUENCE: 8

```
Met Ser Arg Arg Pro Trp Leu Leu Ala Leu Ala Leu Ala Val Ala Leu
 1               5                  10                  15
```

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
 50                  55                  60

Ile Cys Ile Pro Asn Asn Gly Gln Cys Phe Cys Leu Ala Trp Leu Lys
 65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
        115                 120                 125

Glu Met Ile Lys Phe Ile Ile Glu Tyr Phe His Glu Phe Asp Glu Pro
130                 135                 140

Ala Val Ile Tyr Ser Ser Asn Gly Asn Lys Thr Val Trp Leu Arg Tyr
145                 150                 155                 160

Ala Glu Trp Leu Leu Thr Cys Pro Val Leu Leu Ile His Leu Ser Asn
                165                 170                 175

Leu Thr Gly Leu Lys Asp Asp Tyr Ser Lys Arg Thr Met Gly Leu Leu
            180                 185                 190

Val Ser Asp Val Gly Cys Ile Val Trp Gly Ala Thr Ser Ala Met Cys
        195                 200                 205

Thr Gly Trp Thr Lys Ile Leu Phe Phe Leu Ile Ser Leu Ser Tyr Gly
210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
            260                 265                 270

Thr Glu Gly Phe Gly His Ile Ser Pro Tyr Gly Ser Ala Ile Gly His
        275                 280                 285

Ser Ile Leu Asp Leu Ile Ala Lys Asn Met Trp Gly Val Leu Gly Asn
290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Glu Asp
            340

<210> SEQ ID NO 9
<211> LENGTH: 344
<212> TYPE: PRT
<213> ORGANISM: Artificial Sequence
<220> FEATURE:
<223> OTHER INFORMATION: Synthetic polypeptide

<400> SEQUENCE: 9

Met Ser Arg Arg Pro Trp Leu Leu Ala Leu Ala Leu Ala Val Ala Leu
 1               5                  10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
            35                  40                  45

Arg Met Leu Phe Gln Thr Ser Tyr Thr Leu Glu Asn Asn Gly Ser Val
 50                  55                  60

Ile Cys Ile Pro Asn Asn Gly Gln Cys Phe Cys Leu Ala Trp Leu Lys
 65                  70                  75                  80

Ser Asn Gly Thr Asn Ala Glu Lys Leu Ala Asn Ile Leu Gln Trp
                85                  90                  95

Ile Thr Phe Ala Leu Ser Ala Leu Cys Leu Met Phe Tyr Gly Tyr Gln
                100                 105                 110

Thr Trp Lys Ser Thr Cys Gly Trp Glu Thr Ile Tyr Val Ala Thr Ile
                115                 120                 125

Glu Met Ile Lys Phe Ile Ile Glu Tyr Phe His Glu Phe Asp Glu Pro
                130                 135                 140

Ala Val Ile Tyr Ser Ser Asn Gly Asn Lys Thr Val Trp Leu Arg Tyr
145                 150                 155                 160

Ala Glu Trp Leu Leu Thr Cys Pro Val Leu Leu Ile His Leu Ser Asn
                165                 170                 175

Leu Thr Gly Leu Lys Asp Asp Tyr Ser Lys Arg Thr Met Gly Leu Leu
                180                 185                 190

Val Ser Asp Val Gly Cys Ile Val Trp Gly Ala Thr Ser Ala Met Cys
                195                 200                 205

Thr Gly Trp Thr Lys Ile Leu Phe Phe Leu Ile Ser Leu Ser Tyr Gly
                210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
                260                 265                 270

Thr Glu Gly Phe Gly His Ile Ser Pro Tyr Gly Ser Ala Ile Gly His
                275                 280                 285

Ser Ile Leu Asp Leu Ile Ala Lys Asn Met Trp Gly Val Leu Gly Asn
                290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Glu Asp
            340

<210> SEQ ID NO 10
<211> LENGTH: 344
<212> TYPE: PRT
<213> ORGANISM: Artificial Sequence
<220> FEATURE:
<223> OTHER INFORMATION: Synthetic polypeptide

<400> SEQUENCE: 10

Met Ser Arg Arg Pro Trp Leu Leu Ala Leu Ala Leu Ala Val Ala Leu
 1                   5                  10                  15

Ala Ala Gly Ser Ala Gly Ala Ser Thr Gly Ser Asp Ala Thr Val Pro
                20                  25                  30

Val Ala Thr Gln Asp Gly Pro Asp Tyr Val Phe His Arg Ala His Glu
            35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
                100                 105                 110

Thr Trp Lys Ser Thr Cys Gly Trp Glu Glu Ile Tyr Val Ala Thr Ile
                115                 120                 125

Glu Met Ile Lys Phe Ile Ile Glu Tyr Phe His Glu Phe Asp Glu Pro
    130                 135                 140

Ala Val Ile Tyr Ser Ser Asn Gly Asn Lys Thr Val Trp Leu Arg Tyr
145                 150                 155                 160

Ala Thr Trp Leu Leu Thr Cys Pro Val Leu Leu Ile His Leu Ser Asn
                165                 170                 175

Leu Thr Gly Leu Lys Asp Asp Tyr Ser Lys Arg Thr Met Gly Leu Leu
                180                 185                 190

Val Ser Asp Val Gly Cys Ile Val Trp Gly Ala Thr Ser Ala Met Cys
    195                 200                 205

Thr Gly Trp Thr Lys Ile Leu Phe Phe Leu Ile Ser Leu Ser Tyr Gly
    210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
                260                 265                 270

Thr Glu Gly Phe Gly His Ile Ser Pro Tyr Gly Ser Ala Ile Gly His
    275                 280                 285

Ser Ile Leu Asp Leu Ile Ala Lys Asn Met Trp Gly Val Leu Gly Asn
    290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Glu Asp
                340

<210> SEQ ID NO 11
<211> LENGTH: 344
<212> TYPE: PRT
<213> ORGANISM: Artificial Sequence
<220> FEATURE:
<223> OTHER INFORMATION: Synthetic polypeptide

<400> SEQUENCE: 11

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
                20                  25                  30

Val Ala Thr Gln Asp Gly Pro Asp Tyr Val Phe His Arg Ala His Glu
            35                  40                  45

Arg Met Leu Phe Gln Thr Ser Tyr Thr Leu Glu Asn Asn Gly Ser Val
    50                  55                  60

```
Ile Cys Ile Pro Asn Asn Gly Gln Cys Phe Cys Leu Ala Trp Leu Lys
 65                  70                  75                  80

Ser Asn Gly Thr Asn Ala Glu Lys Leu Ala Ala Asn Ile Leu Gln Trp
                 85                  90                  95

Ile Thr Phe Ala Leu Ser Ala Leu Cys Leu Met Phe Tyr Gly Tyr Gln
                100                 105                 110

Thr Trp Lys Ser Thr Cys Gly Trp Glu Thr Ile Tyr Val Ala Thr Ile
            115                 120                 125

Glu Met Ile Lys Phe Ile Ile Glu Tyr Phe His Glu Phe Asp Glu Pro
        130                 135                 140

Ala Val Ile Tyr Ser Ser Asn Gly Asn Lys Thr Val Trp Leu Arg Tyr
145                 150                 155                 160

Ala Thr Trp Leu Leu Thr Cys Pro Val Leu Leu Ile His Leu Ser Asn
                165                 170                 175

Leu Thr Gly Leu Lys Asp Asp Tyr Ser Lys Arg Thr Met Gly Leu Leu
                180                 185                 190

Val Ser Asp Val Gly Cys Ile Val Trp Gly Ala Thr Ser Ala Met Cys
            195                 200                 205

Thr Gly Trp Thr Lys Ile Leu Phe Phe Leu Ile Ser Leu Ser Tyr Gly
        210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
                260                 265                 270

Thr Glu Gly Phe Gly His Ile Ser Pro Tyr Gly Ser Ala Ile Gly His
            275                 280                 285

Ser Ile Leu Asp Leu Ile Ala Lys Asn Met Trp Gly Val Leu Gly Asn
290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Glu Asp
            340

<210> SEQ ID NO 12
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (2)...(2)
<223> OTHER INFORMATION: X = any amino acid

<400> SEQUENCE: 12

Phe Xaa Tyr Glu Asn Glu
 1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic peptide
```

```
<400> SEQUENCE: 13

Phe Cys Tyr Glu Asn Glu Val
 1               5

<210> SEQ ID NO 14
<211> LENGTH: 20
<212> TYPE: PRT
<213> ORGANISM: Artificial Sequence
<220> FEATURE:
<223> OTHER INFORMATION: Synthetic peptide

<400> SEQUENCE: 14

Lys Ser Arg Ile Thr Ser Glu Gly Glu Tyr Ile Pro Leu Asp Gln Ile
 1               5                  10                  15

Asp Ile Asn Val
            20
```

OPTICALLY-CONTROLLED CNS DYSFUNCTION

CROSS REFERENCE TO RELATED APPLICATION

This application is a divisional of U.S. patent application Ser. No. 14/555,048, filed Nov. 26, 2014, now U.S. Pat. No. 9,421,258, which is a divisional of U.S. patent application Ser. No. 13/882,719, filed Jul. 29, 2013, now U.S. Pat. No. 8,932,562, which is a national stage filing under 35 U.S.C. § 371 of PCT/US2011/059298, filed Nov. 4, 2011, which claims the priority benefit of U.S. provisional application Ser. No. 61/410,748 filed on Nov. 5, 2010, and 61/464,806 filed on Mar. 8, 2011, the contents of each of which are incorporated herein by reference in their entirety.

BACKGROUND OF THE INVENTION

Anxiety is a sustained state of heightened apprehension in the absence of immediate threat, which in disease states becomes severely debilitating. Anxiety disorders represent the most common of the psychiatric diseases (with 28% lifetime prevalence), and have been linked to the etiology of major depression and substance abuse. While the amygdala, a brain region important for emotional processing, has long been hypothesized to play a role in anxiety, the neural mechanisms which control and mediate anxiety have yet to be identified. Despite the high prevalence and severity of anxiety disorders, the corresponding neural circuit substrates are poorly understood, impeding the development of safe and effective treatments. Available treatments tend to be inconsistently effective or, in the case of benzodiazepines, addictive and linked to significant side effects including sedation and respiratory suppression that can cause cognitive impairment and death. A deeper understanding of anxiety control mechanisms in the mammalian brain is necessary to develop more efficient treatments that have fewer side-effects. Of particular interest and novelty would be the possibility of recruiting native pathways for anxiolysis.

SUMMARY OF THE INVENTION

Provided herein is an animal comprising a light-responsive opsin expressed in glutamatergic pyramidal neurons of the basolateral amygdala (BLA), wherein the selective illumination of the opsin in the BLA-CeL induces anxiety or alleviates anxiety of the animal.

Provided herein is an animal comprising a light-responsive opsin expressed in glutamatergic pyramidal neurons of the BLA, wherein the opsin is an opsin which induces hyperpolarization by light, and wherein the selective illumination of the opsin in the BLA-CeL induces anxiety of the animal. In some embodiments, the opsin is NpHR, BR, AR, or GtR3. In some embodiments, the NpHR comprises the amino acid sequence of SEQ ID NO:1, 2, or 3. In some embodiments, the animal further comprises a second light-responsive opsin expressed in glutamatergic pyramidal neurons of the BLA, wherein the second opsin is an opsin that induces depolarization by light, and wherein the selective illumination of the second opsin in the BLA-CeL reduces anxiety of the animal. In some embodiments, the second opsin is ChR2, VChR1, or DChR. In some embodiments, the second opsin is a C1V1 chimeric protein comprising the amino acid sequence of SEQ ID NO:8, 9, 10, or 11. In some embodiments, the second opsin comprises the amino acid sequence of SEQ ID NO:6 or 7.

Provided herein is an animal comprising a light-responsive opsin expressed in the glutamatergic pyramidal neurons of the BLA, wherein the opsin is an opsin that induces depolarization by light, and wherein the selective illumination of the opsin in the BLA-CeL reduces anxiety of the animal. In some embodiments, the opsin is ChR2, VChR1, or DChR. In some embodiments, the opsin is a C1V1 chimeric protein comprising the amino acid sequence of SEQ ID NO:8, 9, 10, or 11. In some embodiments, the opsin comprises the amino acid sequence of SEQ ID NO:6 or 7.

Also provided herein is a vector for delivering a nucleic acid to glutamatergic pyramidal neurons of the BLA in an individual, wherein the vector comprises the nucleic acid encoding a light-responsive opsin and the nucleic acid is operably linked to a promoter that controls the specific expression of the opsin in the glutamatergic pyramidal neurons. In some embodiments, the promoter is a CaMKIIα promoter. In some embodiments, the vector is an AAV vector. In some embodiments, the opsin is an opsin that induces depolarization by light, and wherein selective illumination of the opsin in the BLA-CeL alleviates anxiety. In some embodiments, the opsin that induces depolarization by light is ChR2, VChR1, or DChR. In some embodiments, the opsin is a C1V1 chimeric protein comprising the amino acid sequence of SEQ ID NO:8, 9, 10, or 11. In some embodiments, the opsin comprises the amino acid sequence of SEQ ID NO:6 or 7. In some embodiments, the opsin is an opsin that induces hyperpolarization by light, and wherein selective illumination of the opsin in the BLA-CeL and induces anxiety. In some embodiments, the opsin that induces hyperpolarization by light is NpHR, BR, AR, or GtR3. In some embodiments, the NpHR comprises the amino acid sequence of SEQ ID NO:1, 2, or 3. In some embodiments, the individual is a mouse or a rat. In some embodiments, the individual is a human.

Also provided here is a method of delivering a nucleic acid to glutamatergic pyramidal neurons of the BLA in an individual, comprising administering to the individual an effective amount of a vector comprising a nucleic acid encoding a light-responsive opsin and the nucleic acid is operably linked to a promoter that controls the specific expression of the opsin in the glutamatergic pyramidal neurons. In some embodiments, the promoter is a CaMKIIα promoter. In some embodiments, the vector is an AAV vector. In some embodiments, the opsin is an opsin that induces depolarization by light, and wherein selective illumination of the opsin in the BLA-CeL alleviates anxiety. In some embodiments, the opsin that induces depolarization by light is ChR2, VChR1, or DChR. In some embodiments, the opsin is a C1V1 chimeric protein comprising the amino acid sequence of SEQ ID NO:8, 9, 10, or 11. In some embodiments, the opsin comprises the amino acid sequence of SEQ ID NO:6 or 7. In some embodiments, the opsin is an opsin that induces hyperpolarization by light, and wherein selective illumination of the opsin in the BLA-CeL and induces anxiety. In some embodiments, the opsin that induces hyperpolarization by light is NpHR, BR, AR, or GtR3. In some embodiments, the NpHR comprises the amino acid sequence of SEQ ID NO:1, 2, or 3. In some embodiments, the individual is a mouse or a rat. In some embodiments, the individual is a human.

Also provided herein is a coronal brain tissue slice comprising BLA, CeL, and CeM, wherein a light-responsive opsin is expressed in the glutamatergic pyramidal neurons of the BLA. In some embodiments, the opsin is an opsin that induces depolarization by light. In some embodiments, the opsin that induces depolarization by light is ChR2, VChR1, or DChR. In some embodiments, the opsin is a C1V1 chimeric protein comprising the amino acid sequence of SEQ ID NO:8, 9, 10, or 11. In some embodiments, the opsin comprises the amino acid sequence of SEQ ID NO:6 or 7. In some embodiments, the opsin is an opsin that induces hyperpolarization by light. In some embodiments, the opsin that induces hyperpolarization by light is NpHR, BR, AR, or GtR3. In some embodiments, the NpHR comprises the amino acid sequence of SEQ ID NO:1, 2, or 3. In some embodiments, the tissue is a mouse or a rat tissue.

Also provided herein is a method for screening for a compound that alleviates anxiety, comprising (a) administering a compound to an animal having anxiety induced by selectively illumination of an opsin expressed in the glutamatergic pyramidal neurons of the BLA, wherein the animal comprises a light-responsive opsin expressed in the glutamatergic pyramidal neurons of the BLA, wherein the opsin is an opsin that induces hyperpolarization by light; and (b) determining the anxiety level of the animal, wherein a reduction of the anxiety level indicates that the compound may be effective in treating anxiety. In some embodiments, the opsin is NpHR, BR, AR, or GtR3. In some embodiments, the NpHR comprises the amino acid sequence of SEQ ID NO:1, 2, or 3.

Also provided herein is a method for alleviating anxiety in an individual, comprising: (a) administering to the individual an effective amount of a vector comprising a nucleic acid encoding a light-responsive opsin and the nucleic acid is operably linked to a promoter that controls the specific expression of the opsin in the glutamatergic pyramidal neurons of the BLA, wherein the opsin is expressed in the glutamatergic pyramidal neurons of the BLA, wherein the opsin is an opsin that induces depolarization by light; and (b) selectively illuminating the opsin in the glutamatergic pyramidal neurons in the BLA-CeL to alleviate anxiety. In some embodiments, the promoter is a CaMKIIα promoter. In some embodiments, the vector is an AAV vector. In some embodiments, the opsin is ChR2, VChR1, or DChR. In some embodiments, the opsin is a C1V1 chimeric protein comprising the amino acid sequence of SEQ ID NO:8, 9, 10, or 11. In some embodiments, the opsin comprises the amino acid sequence of SEQ ID NO:6 or 7.

Also provided herein is a method for inducing anxiety in an individual, comprising: (a) administering to the individual an effective amount of a vector comprising a nucleic acid encoding an opsin and the nucleic acid is operably linked to a promoter that controls the specific expression of the opsin in the glutamatergic pyramidal neurons of the BLA, wherein the opsin is expressed in the glutamatergic pyramidal neurons, wherein the opsin is an opsin that induces hyperpolarization by light; and (b) selectively illuminating the opsin in the glutamatergic pyramidal neurons in the BLA-CeL to induce anxiety. In some embodiments, the promoter is a CaMKIIα promoter. In some embodiments, the vector is an AAV vector. In some embodiments, the opsin is NpHR, BR, AR, or GtR3. In some embodiments, the NpHR comprises the amino acid sequence of SEQ ID NO:1, 2, or 3.

It is to be understood that one, some, or all of the properties of the various embodiments described herein may be combined to form other embodiments of the present invention. These and other aspects of the invention will become apparent to one of skill in the art.

BRIEF DESCRIPTION OF THE DRAWINGS

Various example embodiments may be more completely understood in consideration of the following description and the accompanying drawings, in which.

DETAILED DESCRIPTION

Figure 1:
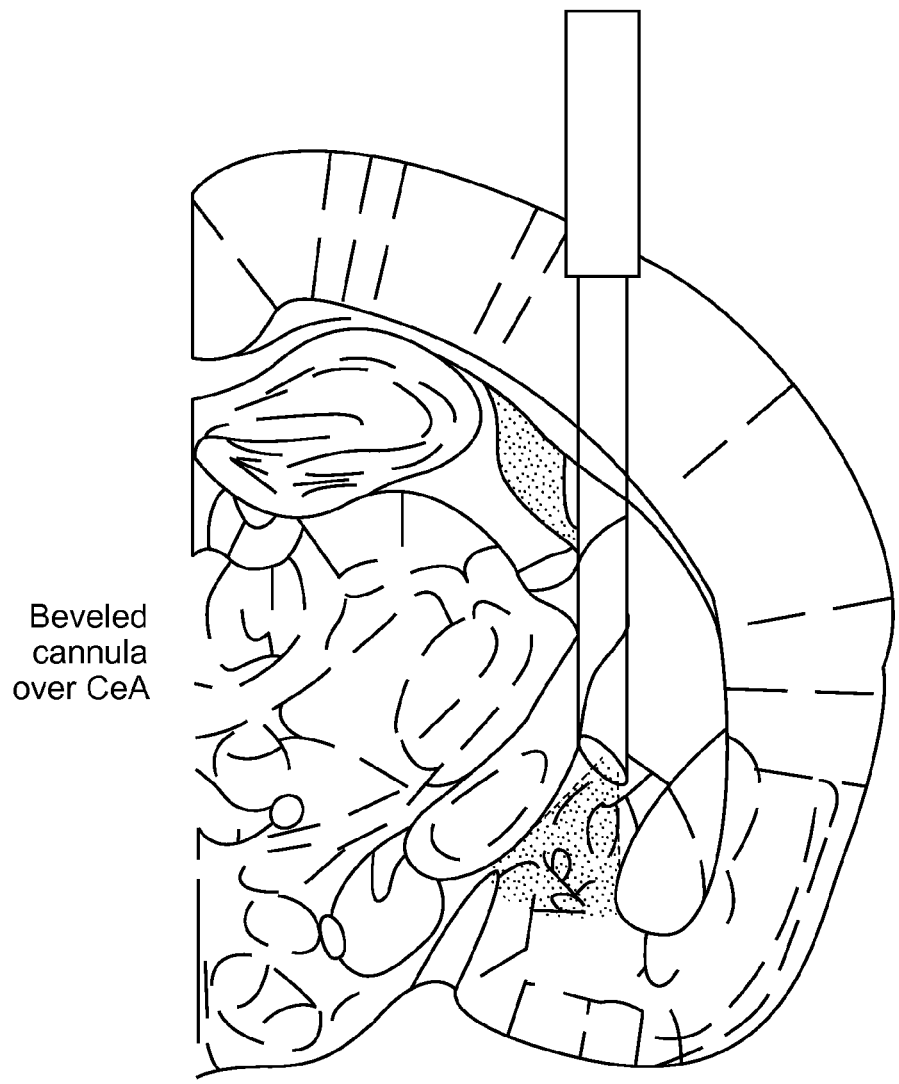
FIG. 1 shows a system for providing optogenetic targeting of specific projections of the brain, consistent with an embodiment of the present disclosure.

The present disclosure relates to control over nervous system disorders, such as disorders associated with anxiety and anxiety symptoms, as described herein. While the present disclosure is not necessarily limited in these contexts, various aspects of the invention may be appreciated through a discussion of examples using these and other contexts.

Various embodiments of the present disclosure relate to an optogenetic system or method that correlates temporal control over a neural circuit with measurable metrics. For instance, various metrics or symptoms might be associated with a neurological disorder exhibiting various symptoms of anxiety. The optogenetic system targets a neural circuit within a patient for selective control thereof. The optogenetic system involves monitoring the patient for the metrics or symptoms associated with the neurological disorder. In this manner, the optogenetic system can provide detailed information about the neural circuit, its function and/or the neurological disorder.

Consistent with the embodiments discussed herein, particular embodiments relate to studying and probing disorders. Other embodiments relate to the identification and/or study of phenotypes and endophenotypes. Still other embodiments relate to the identification of treatment targets.

Aspects of the present disclosure are directed to using an artificially-induced anxiety state for the study of anxiety in otherwise healthy animals. This can be particularly useful for monitoring symptoms and aspects that are poorly understood and otherwise difficult to accurately model in living animals. For instance, it can be difficult to test and/or study anxiety states due to the lack of available animals exhibiting the anxiety state. Moreover, certain embodiments allow for reversible anxiety states, which can be particularly useful in establishing baseline/control points for testing and/or for testing the effects of a treatment on the same animal when exhibiting the anxiety state and when not exhibiting the anxiety state. The reversible anxiety states of certain embodiments can also allow for a reset to baseline between testing the effects of different treatments on the same animal.

Certain aspects of the present disclosure are directed to a method related to control over anxiety and/or anxiety symptoms in a living animal. In certain more specific embodiments, the monitoring of the symptoms also includes assessing the efficacy of the stimulus in mitigating the symptoms of anxiety. Various other methods and applications exist, some of which are discussed in more detail herein.

Light-responsive opsins that may be used in the present invention includes opsins that induce hyperpolarization in neurons by light and opsins that induce depolarization in neurons by light. Examples of opsins are shown in Tables 1 and 2 below.

Table 1 shows identified opsins for inhibition of cellular activity across the visible spectrum:

TABLE 1

Fast optogenetics: inhibition across the visible spectrum

| Opsin Type | Biological Origin | Wavelength Sensitivity | Defined action |
|---|---|---|---|
| NpHR | Natronomonas pharaonis | 589 nm max | Inhibition (hyperpolarization) |
| BR | Halobacterium helobium | 570 nm max | Inhibition (hyperpolarization) |
| AR | Acetabulaira acetabulum | 518 nm max | Inhibition (hyperpolarization) |
| GtR3 | Guillardia theta | 472 nm max | Inhibition (hyperpolarization) |
| Mac | Leptosphaeria maculans | 470-500 nm max | Inhibition (hyperpolarization) |
| NpHr3.0 | Natronomonas pharaonis | 680 nm utility 589 nm max | Inhibition (hyperpolarization) |
| NpHR3.1 | Natronomonas pharaonis | 680 nm utility 589 nm max | Inhibition (hyperpolarization) |

Table 2 shows identified opsins for excitation and modulation across the visible spectrum:

TABLE 2

Fast optogenetics: excitation and modulation across the visible spectrum

| Opsin Type | Biological Origin | Wavelength Sensitivity | Defined action |
|---|---|---|---|
| VChR1 | Volvox carteri | 589 nm utility 535 nm max | Excitation (depolarization) |
| DChR | Dunaliella sauna | 500 nm max | Excitation (depolarization) |
| ChR2 | Chlamydomonas reinhardtii | 470 nm max 380-405 nm utility | Excitation (depolarization) |
| ChETA | Chlamydomonas reinhardtii | 470 nm max 380-405 nm utility | Excitation (depolarization) |
| SFO | Chlamydomonas reinhardtii | 470 nm max 530 nm max | Excitation (depolarization) Inactivation |
| SSFO | Chlamydomonas reinhardtii | 445 nm max 590 nm; 390-400 nm | Step-like activation (depolarization) Inactivation |
| C1V1 | Volvox carteri and Chlamydomonas reinhardtii | 542 nm max | Excitation (depolarization) |
| C1V1 E122 | Volvox carteri and Chlamydomonas reinhardtii | 546 nm max | Excitation (depolarization) |
| C1V1 E162 | Volvox carteri and Chlamydomonas reinhardtii | 542 nm max | Excitation (depolarization) |
| C1V1 E122/E162 | Volvox carteri and Chlamydomonas reinhardtii | 546 nm max | Excitation (depolarization) |

As used herein, a light-responsive opsin (such as NpHR, BR, AR, GtR3, Mac, ChR2, VChR1, DChR, and ChETA) includes naturally occurring protein and functional variants, fragments, fusion proteins comprising the fragments or the full length protein. For example, the signal peptide may be deleted. A variant may have an amino acid sequence at least about any of 90%, 91%, 92%, 93%, 94%, 95%, 96%, 97%, 98%, 99%, or 100% identical to the naturally occurring protein sequence. A functional variant may have the same or similar hyperpolarization function or depolarization function as the naturally occurring protein.

In some embodiments, the NpHR is eNpHR3.0 or eNpHR3.1 (See www.stanford.edu/group/dlab/optogenetics/sequence_info.html). In some embodiments, the light-responsive opsin is a C1V1 chimeric protein or a C1V1-E162 (SEQ ID NO:10), C1V1-E122 (SEQ ID NO:9), or C1V1-E122/E162 (SEQ ID NO:11) mutant chimeric protein (See, Yizhar et al, Nature, 2011, 477(7363):171-78 and www.stanford.edu/group/dlab/optogenetics/sequence_info.html). In some embodiments, the light-responsive opsin is a SFO (SEQ ID NO:6) or SSFO (SEQ ID NO:7) (See, Yizhar et al, Nature, 2011, 477(7363):171-78; Berndt et al., Nat. Neurosci., 12(2):229-34 and www.stanford.edu/group/dlab/optogenetics/sequence_info.html).

In some embodiments, the light-activated protein is a NpHR opsin comprising an amino acid sequence at least 95%, at least 96%, at least 97%, at least 98%, at least 99% or 100% identical to the sequence shown in SEQ. ID NO:1. In some embodiments, the NpHR opsin further comprises an endoplasmic reticulum (ER) export signal and/or a membrane trafficking signal. For example, the NpHR opsin comprises an amino acid sequence at least 95% identical to the sequence shown in SEQ ID NO:1 and an endoplasmic reticulum (ER) export signal. In some embodiments, the amino acid sequence at least 95% identical to the sequence shown in SEQ ID NO:1 is linked to the ER export signal through a linker. In some embodiments, the ER export signal comprises the amino acid sequence FXYENE, where X can be any amino acid. In another embodiment, the ER export signal comprises the amino acid sequence VXXSL, where X can be any amino acid. In some embodiments, the ER export signal comprises the amino acid sequence FCYENEV. In some embodiments, the NpHR opsin comprises an amino acid sequence at least 95% identical to the sequence shown in SEQ ID NO:1, an ER export signal, and a membrane trafficking signal. In other embodiments, the NpHR opsin comprises, from the N-terminus to the C-terminus, the amino acid sequence at least 95% identical to the sequence shown in SEQ ID NO:1, the ER export signal, and the membrane trafficking signal. In other embodiments, the NpHR opsin comprises, from the N-terminus to the C-terminus, the amino acid sequence at least 95% identical to the sequence shown in SEQ ID NO:1, the membrane trafficking signal, and the ER export signal. In some embodiments, the membrane trafficking signal is derived from the amino acid sequence of the human inward rectifier potassium channel $K_{ir}2.1$. In some embodiments, the membrane trafficking signal comprises the amino acid sequence K S R I T S E G E Y I P L D Q I D I N V. In some embodiments, the membrane trafficking signal is linked to the amino acid sequence at least 95% identical to the sequence shown in SEQ ID NO:1 by a linker. In some embodiments, the membrane trafficking signal is linked to the ER export signal through a linker. The linker may comprise any of 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments, the light-activated opsin further comprises an N-terminal signal peptide. In some embodiments, the light-activated opsin comprises the amino acid sequence of SEQ ID NO:2. In some embodiments, the light-activated protein comprises the amino acid sequence of SEQ ID NO:3.

In some embodiments, the light-activated opsin is a chimeric protein derived from VChR1 from *Volvox carteri* and ChR1 from *Chlamydomonas reinhardti*. In some embodiments, the chimeric protein comprises the amino acid sequence of VChR1 having at least the first and second transmembrane helices replaced by the corresponding first and second transmembrane helices of ChR1. In other embodiments, the chimeric protein comprises the amino acid sequence of VChR1 having the first and second transmembrane helices replaced by the corresponding first and second transmembrane helices of ChR1 and further comprises at least a portion of the intracellular loop domain located between the second and third transmembrane helices replaced by the corresponding portion from ChR1. In some embodiments, the entire intracellular loop domain between the second and third transmembrane helices of the chimeric light-activated protein can be replaced with the corresponding intracellular loop domain from ChR1. In some embodiments, the light-activated chimeric protein comprises an amino acid sequence at least 90%, 91%, 92%, 93%, 94%, 95%, 96%, 97%, 98%, 99%, or 100% identical to the sequence shown in SEQ ID NO:8 without the signal peptide sequence. In some embodiments, the light-activated chimeric protein comprises an amino acid sequence at least 90%, 91%, 92%, 93%, 94%, 95%, 96%, 97%, 98%, 99%, or 100% identical to the sequence shown in SEQ ID NO:8. C1V1 chimeric light-activated opsins that may have specific amino acid substitutions at key positions throughout the retinal binding pocket of the VChR1 portion of the chimeric polypeptide. In some embodiments, the C1V1 protein has a mutation at amino acid residue E122 of SEQ ID NO:8. In some embodiments, the C1V1 protein has a mutation at amino acid residue E162 of SEQ ID NO:8. In other embodiments, the C1V1 protein has a mutation at both amino acid residues E162 and E122 of SEQ ID NO:8. In some embodiments, each of the disclosed mutant C1V1 chimeric proteins can have specific properties and characteristics for use in depolarizing the membrane of an animal cell in response to light.

As used herein, a vector comprises a nucleic acid encoding a light-responsive opsin described herein and the nucleic acid is operably linked to a promoter that controls the specific expression of the opsin in the glutamatergic pyramidal neurons. Any vectors that are useful for delivering a nucleic acid to glutamatergic pyramidal neurons may be used. Vectors include viral vectors, such as AAV vectors, retroviral vectors, adenoviral vectors, HSV vectors, and lentiviral vectors. Examples of AAV vectors are AAV1, AAV2, AAV3, AAV4, AAV5, AAV6, AAV7, AAV8, AAV9, AAV10, AAV11, AAV12, AAV13, AAV14, AAV15, and AAV16. A CaMKIIα promoter and any other promoters that can control the expression of the opsin in the glutamatergic pyramidal neurons may be used.

An "individual" is a mammal, such as a human. Mammals also include, but are not limited to, farm animals, sport animals, pets (such as cats, dogs, horses), primates, mice and rats. An "animal" is a non-human mammal.

As used herein, "treatment" or "treating" or "alleviation" is an approach for obtaining beneficial or desired results including and preferably clinical results. For purposes of this invention, beneficial or desired clinical results include, but are not limited to, one or more of the following: showing observable and/or measurable reduction in one or more signs of the disease (such as anxiety), decreasing symptoms resulting from the disease, increasing the quality of life of those suffering from the disease, decreasing the dose of other medications required to treat the disease, and/or delaying the progression of the disease.

As used herein, an "effective dosage" or "effective amount" of a drug, compound, or pharmaceutical composition is an amount sufficient to effect beneficial or desired results. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, and/or delaying the progression of the disease. As is understood in the clinical context, an effective dosage of a drug, compound, or pharmaceutical composition may or may not be achieved in conjunction with another drug, compound, pharmaceutical composition, or another treatment. Thus, an "effective dosage" may be considered in the context of administering one or more therapeutic agents or treatments, and a single agent may be considered to be given in an effective amount if, in conjunction with one or more other agents or treatments, a desirable result may be or is achieved.

The above overview is not intended to describe each illustrated embodiment or every implementation of the present disclosure.

DETAILED DESCRIPTION AND EXAMPLE EXPERIMENTAL EMBODIMENTS

The present disclosure is believed to be useful for controlling anxiety states and/or symptoms of anxiety. Specific applications of the present invention relate to optogenetic systems or methods that correlate temporal, spatio and/or cell-type control over a neural circuit associated with anxiety states and/or symptoms thereof. As many aspects of the example embodiments disclosed herein relate to and significantly build on previous developments in this field, the following discussion summarizes such previous developments to provide a solid understanding of the foundation and underlying teachings from which implementation details and modifications might be drawn, including those found in the Examples. It is in this context that the following discussion is provided and with the teachings in the references incorporated herein by reference. While the present invention is not necessarily limited to such applications, various aspects of the invention may be appreciated through a discussion of various examples using this context.

Anxiety refers to a sustained state of heightened apprehension in the absence of an immediate threat, which in disease states becomes severely debilitating. Embodiments of the present disclosure are directed toward the use of one or more of cell type-specific optogenetic tools with two-photon microscopy, electrophysiology, and anxiety assays to study and develop treatments relating to neural circuits underlying anxiety-related behaviors.

Aspects of the present disclosure are related to the optogenetic targeting of specific projections of the brain, rather than cell types, in the study of neural circuit function relevant to psychiatric disease.

Consistent with particular embodiments of the present disclosure, temporally-precise optogenetic stimulation of basolateral amygdala (BLA) terminals in the central nucleus of the amygdala (CeA) are used to produce a reversible anxiolytic effect. The optogenetic stimulation can be implemented by viral transduction of BLA with a light-responsive opsin, such as ChR2, followed by restricted illumination in downstream CeA.

Consistent with other embodiments of the present disclosure, optogenetic inhibition of the basolateral amygdala (BLA) terminals in the central nucleus of the amygdala (CeA) are used to increase anxiety-related behaviors. The optogenetic stimulation can be implemented by viral transduction of BLA with a light-responsive opsin, such as eNpHR3.0, followed by restricted illumination in downstream CeA.

Embodiments of the present disclosure are directed towards the specific targeting of neural cell populations, as anxiety-based effects were not observed with direct optogenetic control of BLA somata. For instance, targeting of specific BLA-CeA projections as circuit elements have been experimentally shown to be sufficient for endogenous anxiety control in the mammalian brain.

Consistent with embodiments of the present disclosure, the targeting of the specific BLA-CeA projections as circuit elements is based upon a number of factors discussed in more detail hereafter. The amygdala is composed of functionally and morphologically heterogeneous subnuclei with complex interconnectivity. A primary subdivision of the amygdala is the basolateral amygdala complex (BLA), which encompasses the lateral (LA), basolateral (BL) and basomedial (BM) amygdala nuclei (~90% of BLA neurons are glutamatergic). In contrast, the central nucleus of the amygdala (CeA), which is composed of the centrolateral (CeL) and centromedial (CeM) nuclei, is predominantly (~95%) comprised of GABAergic medium spiny neurons. The BLA is ensheathed in dense clusters of GABAergic intercalated cells (ITCs), which are functionally distinct from both local interneurons and the medium spiny neurons of the CeA. The primary output nucleus of the amygdala is the CeM, which, when chemically or electrically excited, is believed to mediate autonomic and behavioral responses that are associated with fear and anxiety via projections to the brainstem. While the CeM is not directly controlled by the primary amygdala site of converging environmental and cognitive information (LA), LA and BLA neurons excite GABAergic CeL neurons, which can provide feed-forward inhibition onto CeM "output" neurons and reduce amygdala output. The BLA-CeL-CeM is a less-characterized pathway suggested to be involved not in fear extinction but in conditioned inhibition. The suppression of fear expression, possibly due to explicit unpairing of the tone and shock, suggested to be related to the potentiation of BLA-CeL synapses.

BLA cells have promiscuous projections throughout the brain, including to the bed nucleus of the stria terminalis (BNST), nucleus accumbens, hippocampus and cortex. Aspects of the present disclosure relate to methods for selective control of BLA terminals in the CeL, without little or no direct affect/control of other BLA projections. Preferential targeting of BLA-CeL synapses can be facilitated by restricting opsin gene expression to BLA glutamatergic projection neurons and by restricting light delivery to the CeA.

For instance, control of BLA glutamatergic projection neurons can be achieved with an adeno-associated virus (AAV5) vector carrying light-activated optogenetic control genes under the control of a CaMKIIα promoter. Within the BLA, CaMKIIα is only expressed in glutamatergic pyramidal neurons, not in local interneurons or intercalated cells.

FIG. 1 shows a system for providing optogenetic targeting of specific projections of the brain, consistent with an embodiment of the present disclosure. For instance, a beveled guide cannula can be used to direct light, e.g., prevent light delivery to the BLA and allow selective illumination of the CeA. This preferential delivery of light to the CeA projection can be accomplished using stereotaxic guidance along with implantation over the CeL. Geometric and functional properties of the resulting light distribution can be quantified both in vitro and in vivo, e.g., using in vivo electrophysiological recordings to determine light power parameters for selective control of BLA terminals but not BLA cell bodies. Experimental results, such as those described in the Examples, support that such selective excitation or inhibition result in significant, immediate and reversible anxiety-based effects.

Embodiments of the present disclosure are directed toward the above realization being applied to various ones of the anatomical, functional, structural, and circuit targets identified herein. For instance, the circuit targets can be studied to develop treatments for the psychiatric disease of anxiety. These treatments can include, as non-limiting examples, pharmacological, electrical, magnetic, surgical and optogenetic, or other treatment means.

Figure 2:
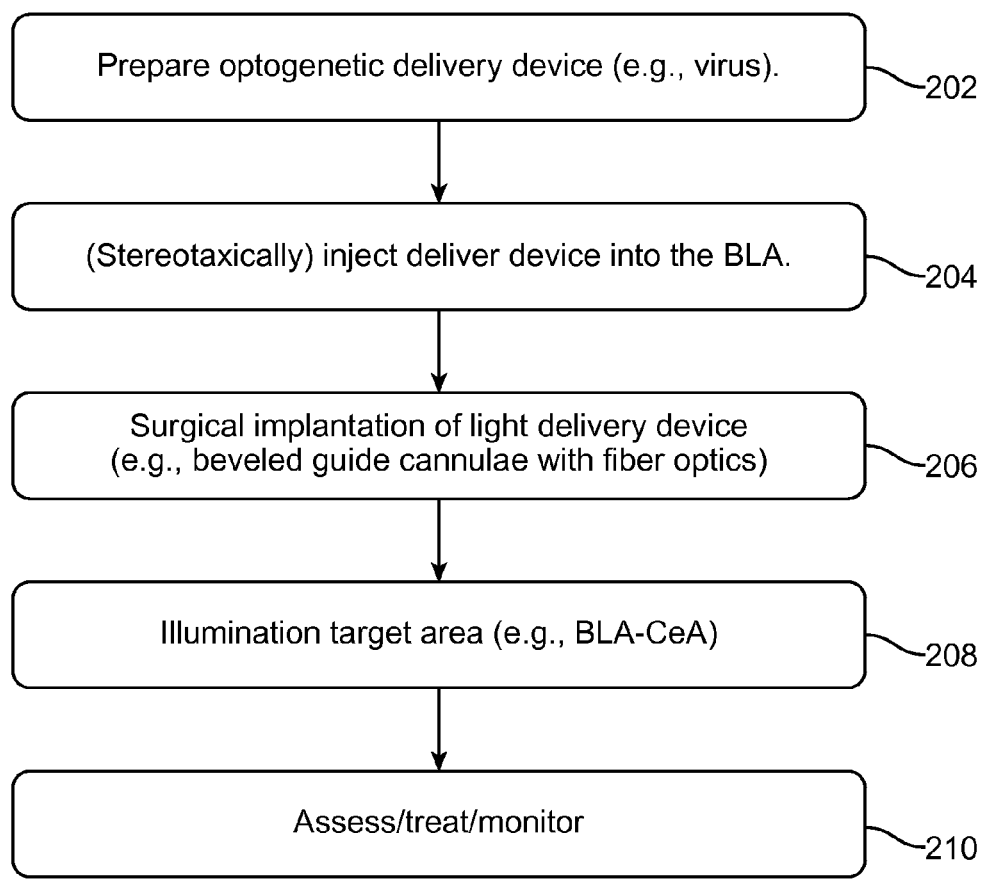
FIG. 2 shows a flow diagram for use of an anxiety-based circuit model, consistent with an embodiment of the present disclosure.

FIG. 2 shows a flow diagram for use of an anxiety-based circuit model, consistent with an embodiment of the present disclosure. An optogenetic delivery device, such as a. viral delivery device, is generated 202. This delivery device can be configured to introduce optically responsive opsins to the target cells and may include targeted promoters for specific cell types. The delivery device can then be stereotaxically (or otherwise) injected 204 into the BLA. A light delivery device can then be surgical implanted 206. This light delivery device can be configured to provide targeted illumination (e.g., using a directional optical element). The target area is then illuminated 208. The target area can be, for example, the BLA-CeA. The effects thereof can then be monitored and/or assessed 210. This can also be used in connection with treatments or drug screening.

Various embodiments of the present disclosure relate to the use of the identified model for screening new treatments for anxiety. For instance, anxiety can be artificially induced or repressed using the methods discussed herein, while pharmacological, electrical, magnetic, surgical, or optogenetic treatments are then applied and assessed. In other embodiments of the present disclosure, the model can be used to develop an in vitro approximation or simulation of the identified circuit, which can then be used in the screening of devices, reagents, tools, technologies, methods and approaches and for studying and probing anxiety and related disorders. This study can be directed towards, but not necessarily limited to, identifying phenotypes, endophenotypes, and treatment targets.

Embodiments of the present disclosure are directed toward modeling the BLA-CeL pathway as an endogenous neural substrate for bidirectionally modulating the unconditioned expression of anxiety. Certain embodiments are directed toward other downstream circuits, such as CeA projections to the BNST, for their role in the expression of anxiety or anxiety-related behaviors. For instance, it is believed that corticotropin releasing hormone (CRH) networks in the BNST may be critically involved in modulating anxiety-related behaviors, as the CeL is a primary source of CRH for the BNST. Other neurotransmitters and neuromodulators may modulate or gate effects on distributed neural circuits, including serotonin, dopamine, acetylcholine, glycine, GABA and CRH. Still other embodiments are directed toward control of the neural circuitry converging to and diverging from this pathway, as parallel or downstream circuits of the BLA-CeL synapse are believed to contribute to the modulation or expression of anxiety phenotypes. Moreover, upstream of the amygdala, this microcircuit is well-positioned to be recruited by top-down cortical control from regions important for processing fear and anxiety, including the prelimbic, infralimbic and insular cortices that provide robust innervation to the BLA and CeL.

Experimental results based upon the BLA anatomy suggest that the populations of BLA neurons projecting to CeL and CeM neurons are largely non-overlapping. In natural states, the CeL-projecting BLA neurons may excite CeM-projecting BLA neurons in a microcircuit homeostatic mechanism, which can then be used to study underlying anxiety disorders when there are synaptic changes that skew the balance of the circuit to allow uninhibited CeM activation.

The embodiments and specific applications discussed herein (including the Examples) may be implemented in connection with one or more of the above-described aspects, embodiments and implementations, as well as with those shown in the figures and described below. Reference may be made to the following Example, which is fully incorporated herein by reference. For further details on light-responsive molecules and/or opsins, including methodology, devices and substances, reference may also be made to the following background publications: U.S. Patent Publication No. 2010/0190229, entitled "System for Optical Stimulation of Target Cells" to Zhang et al.; U.S. Patent Publication No. 2010/0145418, also entitled "System for Optical Stimulation of Target Cells" to Zhang et al.; U.S. Patent Publication No. 2007/0261127, entitled "System for Optical Stimulation of Target Cells" to Boyden et al.; and PCT WO 2011/116238, Entitled "Light Sensitive Ion Passing Molecules". These applications form part of the patent document and are fully incorporated herein by reference. Consistent with these publications, numerous opsins can be used in mammalian cells in vivo and in vitro to provide optical stimulation and control of target cells. For example, when ChR2 is introduced into an electrically-excitable cell, such as a neuron, light activation of the ChR2 channel rhodopsin can result in excitation and/or firing of the cell. In instances when NpHR is introduced into an electrically-excitable cell, such as a neuron, light activation of the NpHR opsin can result in inhibition of firing of the cell. These and other aspects of the disclosures of the above-referenced patent applications may be useful in implementing various aspects of the present disclosure.

While the present disclosure is amenable to various modifications and alternative forms, specifics thereof have been shown by way of example in the drawings and will be described in further detail. It should be understood that the intention is not to limit the disclosure to the particular embodiments and/or applications described. On the contrary, the intention is to cover all modifications, equivalents, and alternatives falling within the spirit and scope of the present disclosure.

EXAMPLES

Introduction

Anxiety is a sustained state of heightened apprehension in the absence of immediate threat, which in disease states becomes severely debilitating[1]. Anxiety disorders represent the most common of the psychiatric diseases (with 28% lifetime prevalence)[2], and have been linked to the etiology of major depression and substance abuse[3-5]. While the amygdala, a brain region important for emotional processing[9-17], has long been hypothesized to play a role in anxiety[18-23], the neural mechanisms which control and mediate anxiety have yet to be identified. Here, we combine cell type-specific optogenetic tools with two-photon microscopy, electrophysiology, and anxiety assays in freely-moving mice to identify neural circuits underlying anxiety-related behaviors. Capitalizing on the unique capability of optogenetics[24-26] to control not only cell types, but also specific connections between cells, we observed that temporally-precise optogenetic stimulation of basolateral amygdala (BLA) terminals in the central nucleus of the amygdala (CeA), resolved by viral transduction of BLA with ChR2 followed by restricted illumination in downstream CeA, exerted a profound, immediate, and reversible anxiolytic effect. Conversely, selective optogenetic inhibition of the same defined projection with eNpHR3.0[25] potently, swiftly, and reversibly increased anxiety-related behaviors. Importantly, these effects were not observed with direct optogenetic control of BLA somata themselves. Together, these results implicate specific BLA-CeA projections as circuit elements both necessary and sufficient for endogenous anxiety control in the mammalian brain, and demonstrate the importance of optogenetically targeting specific projections, rather than cell types, in the study of neural circuit function relevant to psychiatric disease.

Despite the high prevalence and severity[1] of anxiety disorders, the corresponding neural circuit substrates are poorly understood, impeding the development of safe and effective treatments. Available treatments tend to be inconsistently effective or, in the case of benzodiazepines, addictive and linked to significant side effects including sedation and respiratory suppression that can cause cognitive impairment and death[27,28]. A deeper understanding of anxiety control mechanisms in the mammalian brain[29,30] is necessary to develop more efficient treatments that have fewer side-effects. Of particular interest and novelty would be the possibility of recruiting native pathways for anxiolysis.

The amygdala is critically involved in processing associations between neutral stimuli and positive or negative outcomes, and has also been implicated in processing unconditioned emotional states. While the amygdala microcircuit has been functionally dissected in the context of fear conditioning, amygdalar involvement has been implicated in a multitude of other functions and emotional states, including unconditioned anxiety. The amygdala is composed of functionally and morphologically heterogeneous subnuclei with complex interconnectivity. A primary subdivision of the amygdala is the basolateral amygdala complex (BLA), which encompasses the lateral (LA), basolateral (BL) and basomedial (BM) amygdala nuclei (~90% of BLA neurons are glutamatergic)[33, 34]. In contrast, the central nucleus of the amygdala (CeA), which is composed of the centrolateral (CeL) and centromedial (CeM) nuclei, is predominantly (~95%) comprised of GABAergic medium spiny neurons[35]. The BLA is ensheathed in dense clusters of GABAergic intercalated cells (ITCs), which are functionally distinct from both local interneurons and the medium spiny neurons of the CeA[36, 37]. The primary output nucleus of the amygdala is the CeM,[32, 35, 38-40] which when chemically or electrically excited mediates autonomic and behavioral responses associated with fear and anxiety via projections to the brainstem[6, 12, 32, 35]. While the CeM is not directly controlled by the primary amygdala site of converging environmental and cognitive information (LA)[12, 38, 41], LA and BLA neurons excite GABAergic CeL neurons[42] which can provide feed-forward inhibition onto CeM[40, 46] "output" neurons and reduce amygdala output. The BLA-CeL-CeM is a less-characterized pathway suggested to be involved not in fear extinction but in conditioned inhibition, the suppression of fear expression due to explicit unpairing of the tone and shock, due to the potentiation of BLA-CeL synapses[47]. Although fear is characterized to be a phasic state triggered by an external cue, while anxiety is a sustained state that may occur in the absence of an external trigger, we wondered if circuits modulating conditioned inhibition of fear might also be involved in modulating unconditioned inhibition of anxiety.

Materials and Methods

Figure 3:
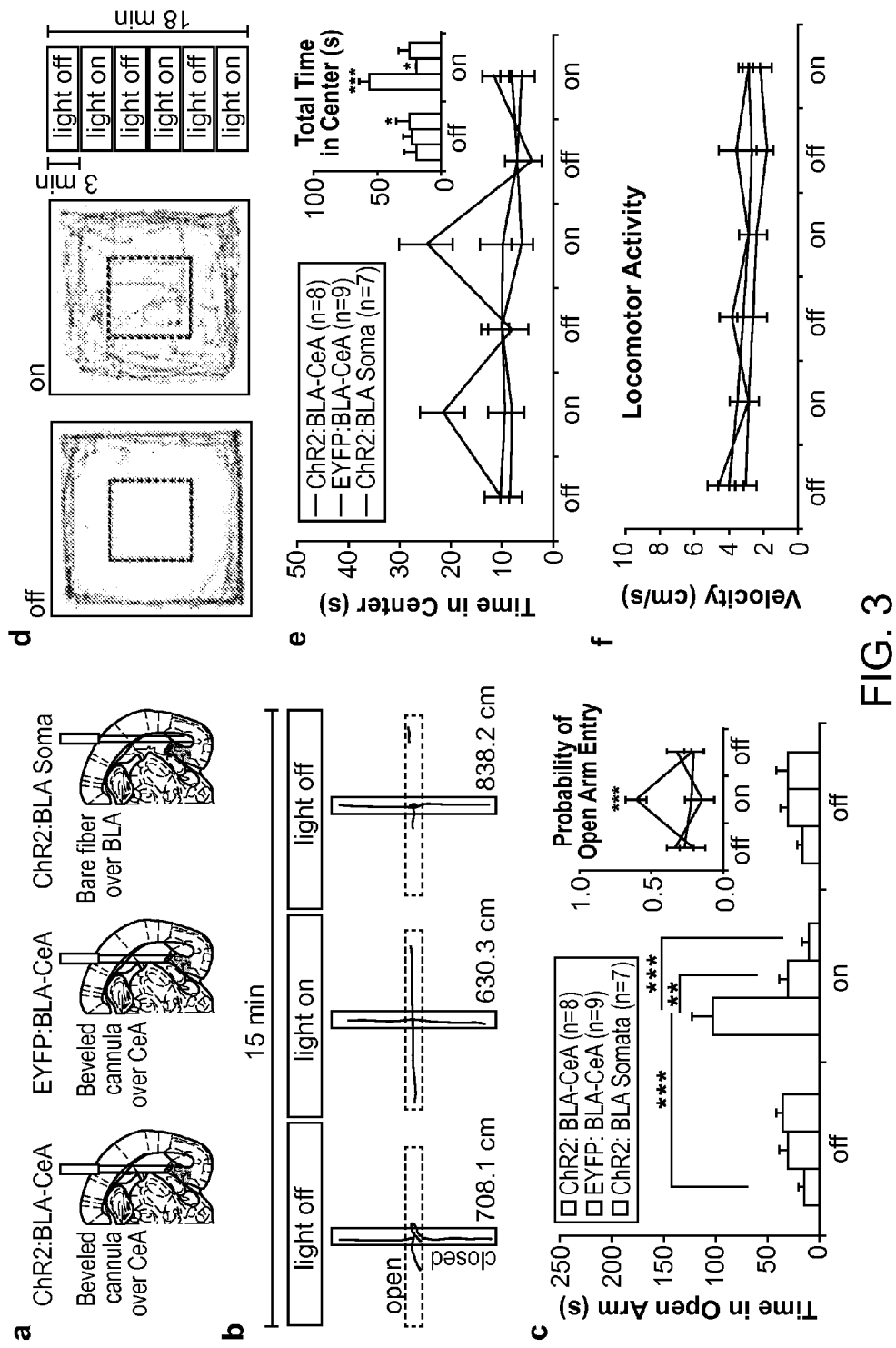
FIG. 3 shows that projection-specific excitation of BLA terminals in the CeA induced acute reversible anxiolysis. a) All mice were singly-housed in a high-stress environment for at least 1 week prior to behavioral manipulations and receive 5-ms light pulses at 20 Hz for all light on conditions. Mice in the ChR2:BLA-CeA group received viral transduction of ChR2 in BLA neurons under the CaMKII promoter and were implanted with a beveled cannula shielding light away from BLA somata to allow selective illumination of BLA terminals in the CeA, while control groups either received a virus including fluorophore only (EYFP:BLA-CeA group) or a light fiber directed to illuminate BLA somata (ChR2:BLA Somata group). (b-c) Mice in the ChR2:BLA-CeA group (n=8) received selective illumination of BLA terminals in the CeA during the light on epoch during the elevated plus maze, as seen in this ChR2:BLA-CeA representative path (b), which induced a 5-fold increase in open arm time during the light on epoch relative to the light off epochs and EYFP:BLA-CeA (n=9) and ChR2:BLA Somata (n=7) controls (c), as well as a significant increase in the probability of entering the open arm (see inset). (d-f) Mice in the ChR2:BLA-CeA group also showed an increase in the time spent in the center of the open field chamber, as seen in this representative trace (d), during light on epochs relative to light off epochs and EYFP:BLA-CeA and ChR2:BLA Somata controls (e), but did not show a significant change in locomotor activity during light on epochs (f). g) Confocal image of a coronal slice showing the CeA and BLA regions from a mouse in the ChR2:BLA-CeA group wherein 125 μm×125 μm squares indicate regions used for quantification. h) Expanded regions are arranged in rows by group and in columns by brain region. (i-k) Percent of EYFP-positive and c-fos-positive neurons of all DAPI-identified cells for all groups, by region. Numbers of counted per group and region are indicated in legends. None of the regions examined showed detectable differences in the proportion of EYFP-positive cells among groups. i) Proportion of BLA neurons that were EYFP-positive or c-fos-positive. The ChR2:BLA Somata group had a significantly higher proportion of c-fos-positive BLA neurons ($F_{2,9}$=10.12, p<0.01) relative to ChR2:BLA-CeA (p<0.01) or EYFP:BLA-CeA (p<0.05) groups. j) The ChR2:BLA-CeA group had a significantly higher proportion of c-fos-positive cells in the CeL relative to the EYFP:BLA-CeA group (p<0.05), but not the ChR2:BLA Somata group. k) Summary data for CeM neurons show no detectable differences among groups.
Figure 3:
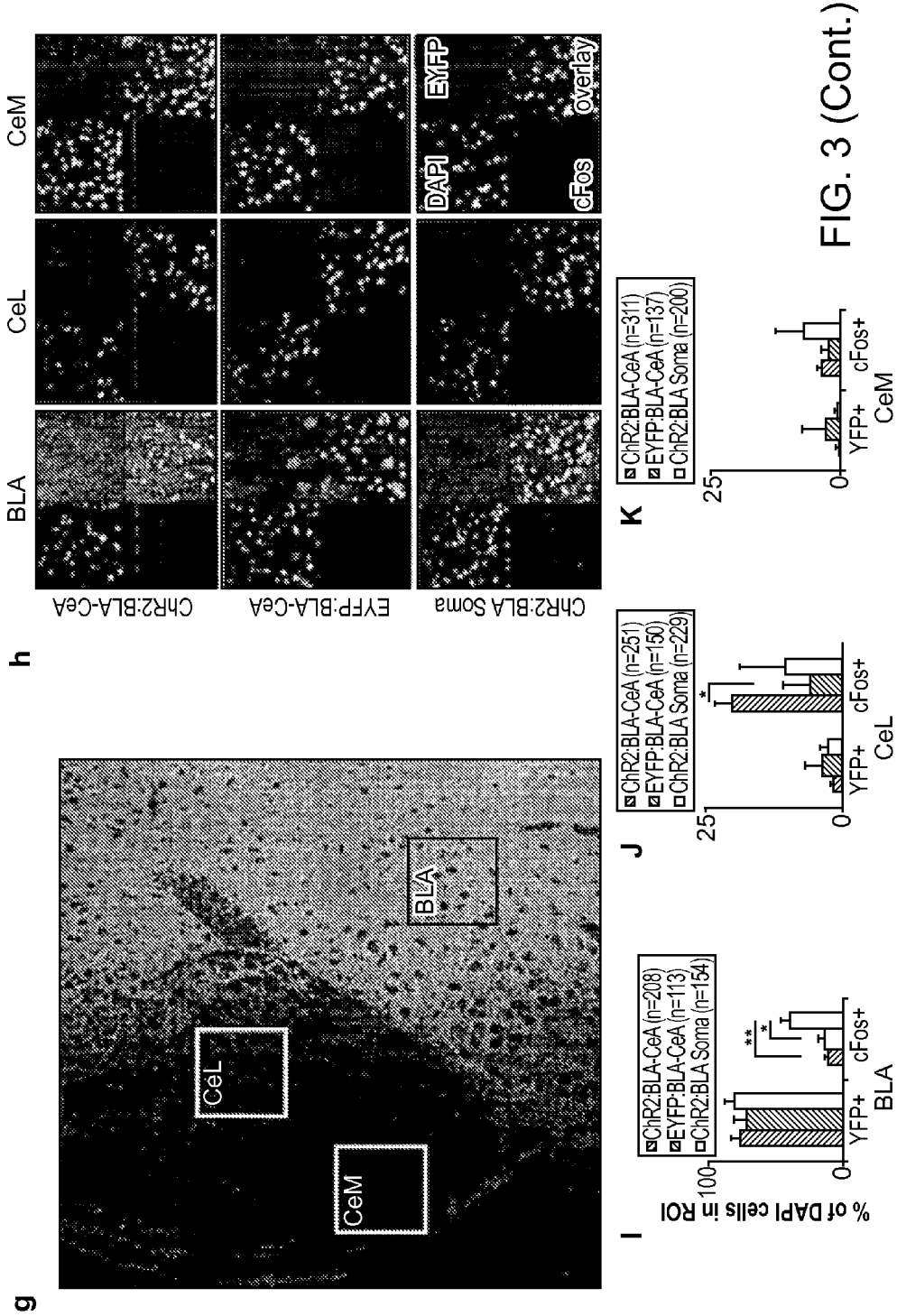
Figure 4:
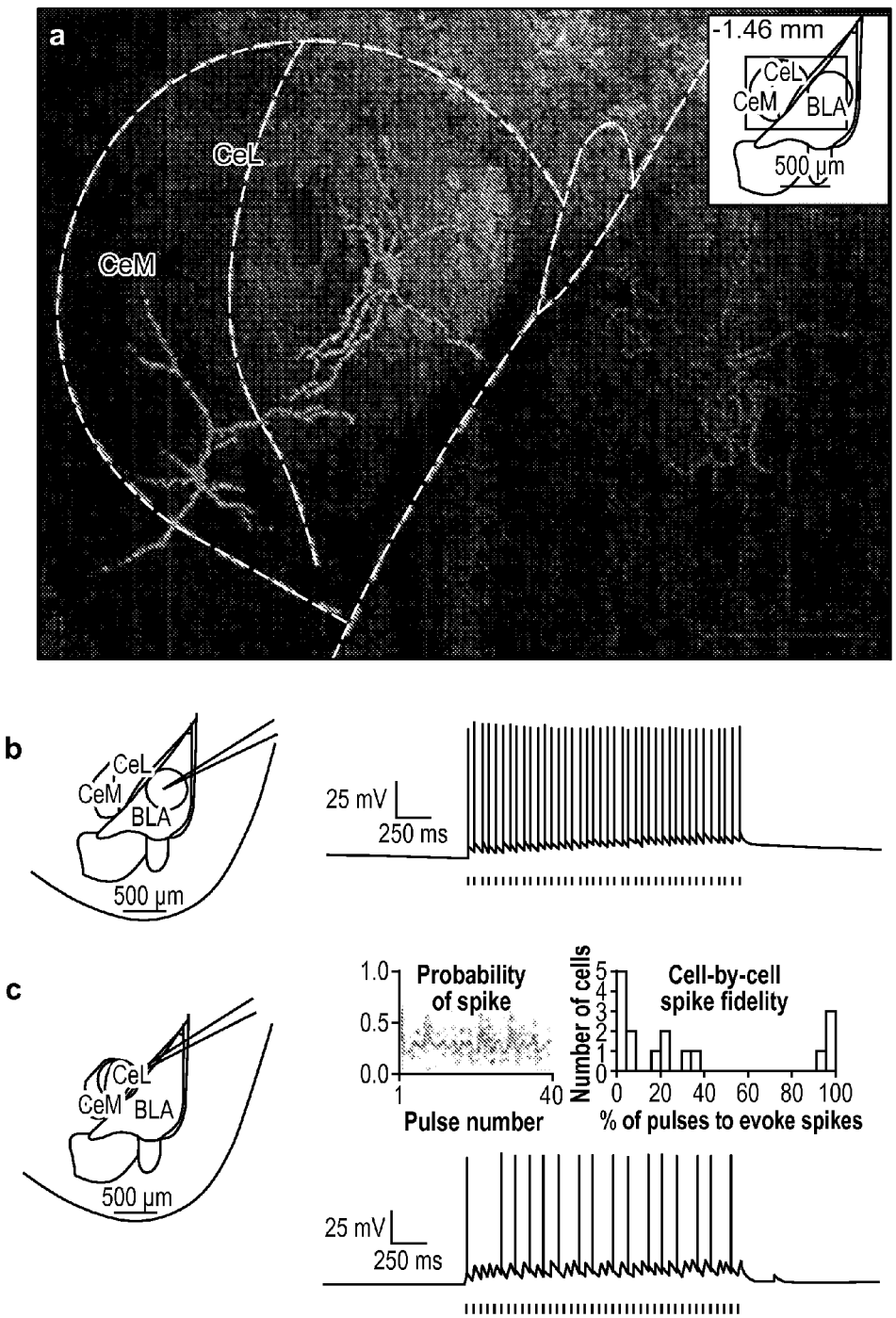
FIG. 4 shows projection-specific excitation of BLA terminals in the CeA activates CeL neurons and elicits feedforward inhibition of CeM neurons. a) Live two-photon images of representative light-responsive BLA, CeL and CeM cells all imaged from the same slice, overlaid on a brightfield image. (b-f) Schematics of the recording and illumination sites for the associated representative current-clamp traces ($V_m$=−70 mV). b) Representative trace from a BLA pyramidal neuron expressing ChR2, all BLA neurons expressing ChR2 in the BLA spiked for every 5 ms pulse (n=4). c) Representative trace from a CeL neuron in the terminal field of BLA projection neurons, showing both sub-threshold and supra-threshold excitatory responses to light-stimulation (n=16). Inset left, population summary of mean probability of spiking for each pulse in a 40-pulse train at 20 Hz, dotted lines indicate SEM. Inset right, frequency histogram showing individual cell spiking fidelity for 5 ms light pulses delivered at 20 Hz, y-axis is the number of cells per each 5% bin. d) Six sweeps from a CeM neuron spiking in response to a current step (~60 pA; indicated in black) and inhibition of spiking upon 20 Hz illumination of BLA terminals in the CeL. Inset, spike frequency was significantly reduced during light stimulation of CeL neurons (n=4). (e-f) Upon broad illumination of the CeM, voltage-clamp summaries show that the latency of EPSCs is significantly shorter than the latency of IPSCs, while there was a non-significant difference in the amplitude of EPSCs and IPSCs (n=11; *p=0.04, see insets). The same CeM neurons (n=7) showed either net excitation when receiving illumination of the CeM (e) or net inhibition upon selective illumination of the CeL (f).
Figure 4:
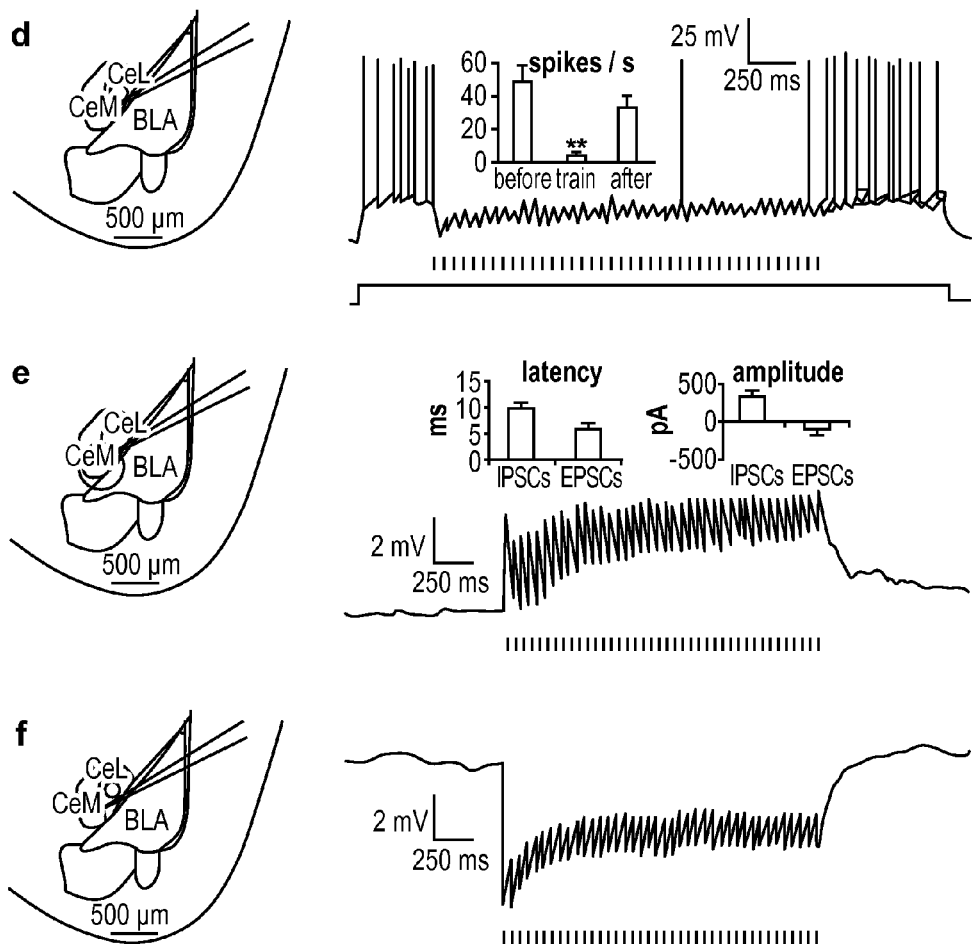
Figure 5:
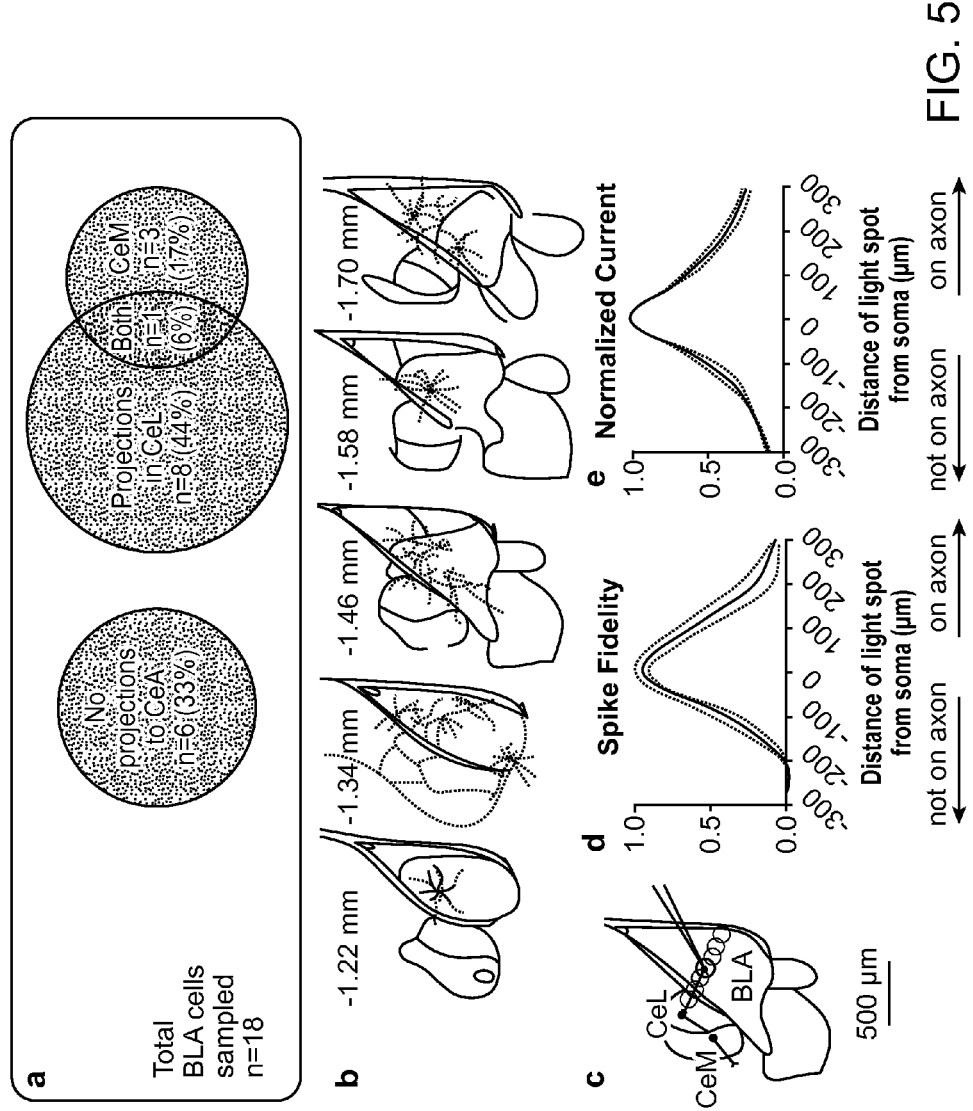
FIG. 5 shows light-induced anxiolytic effects were attributable to activation of BLA-CeL synapses alone. (a-b) 2-photon z-stack images of 18 dye-filled BLA neurons were reconstructed, and their projections to the CeL and CeM are summarized in (a), with their images shown in (b) wherein red indicates projections to CeL, blue indicates projections to CeM and purple indicates projections to both CeL and CeM. c) Schematic of the recording site and the light spot positions, as whole-cell recordings were performed at each location of the light spot, which was moved in 100 um-steps away from the cell soma both over a visualized axon and in a direction that was not over an axon. d) Normalized current-clamp summary of spike fidelity to a 20 Hz train delivered at various distances from the soma, showing that at ~300 um away from the cell soma, illumination of an axon terminal results in low (<5%) spike fidelity. e) Normalized voltage-clamp summary of depolarizing current seen at the cell soma upon illumination per distance from cell soma. (f-i) Representative current-clamp traces upon illumination with a ~150 um-diameter light spot over various locations within each slice preparation (n=7). Illumination of the cell soma elicits high-fidelity spiking (f). Illumination of BLA terminals in CeL elicits strong sub- and supra-threshold excitatory responses in the postsynaptic CeL neuron (g), but does not elicit reliable antidromic spiking in the BLA neuron itself (h), and light delivered off axon is shown for comparison as a control for light scattering (i). (k-j) A separate group of ChR2:BLA-CeL mice (n=8) were each run twice on the elevated plus maze and the open field test, one session preceded with intra-CeA infusions of saline (red) and the other session with the glutamate receptor antagonists NBQX and AP5 (purple), counterbalanced for order. k) Glutamate receptor blockade in the CeA attenuated light-induced increases in both time spent in open arms as well as the probability of open arm entry (inset) on the elevated plus maze without impairing performance during light off epochs. j) Local glutamate receptor antagonism significantly attenuated light-induced increases in center time on the open field test, inset shows pooled summary.
Figure 5:
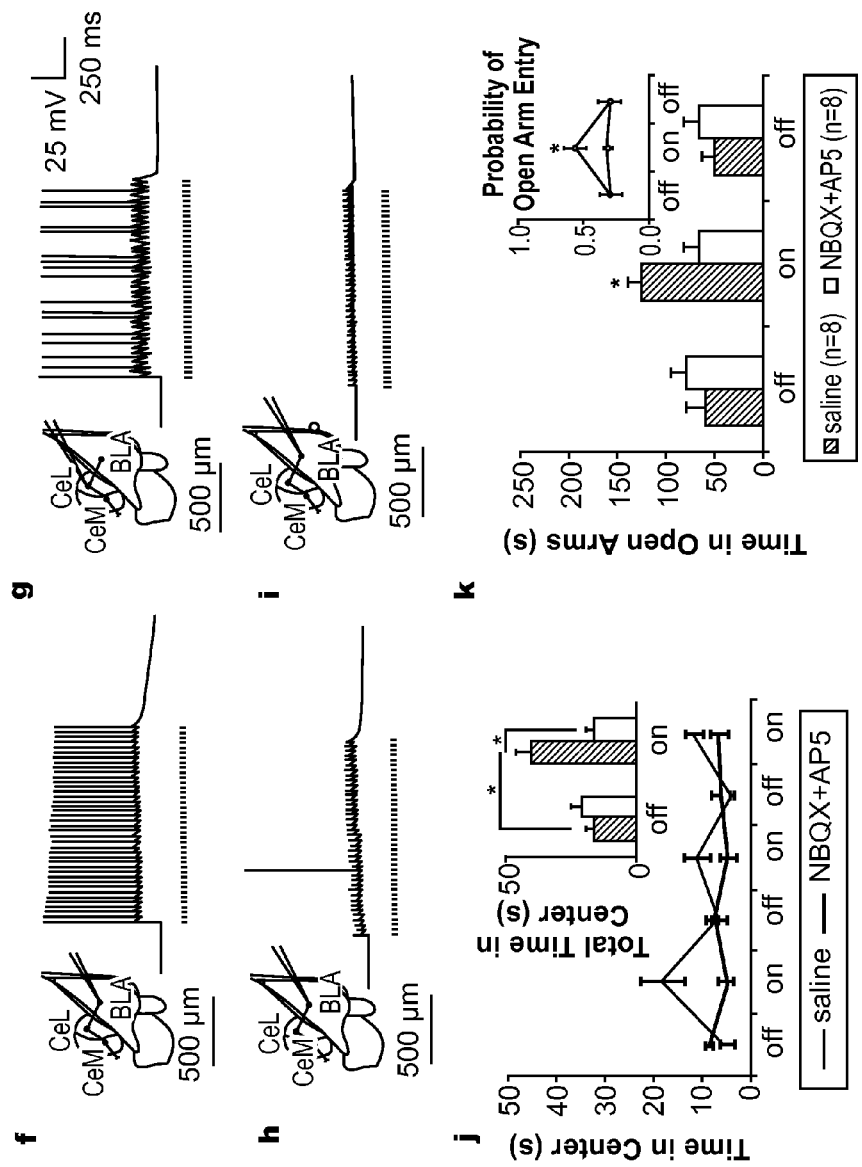
Figure 6:
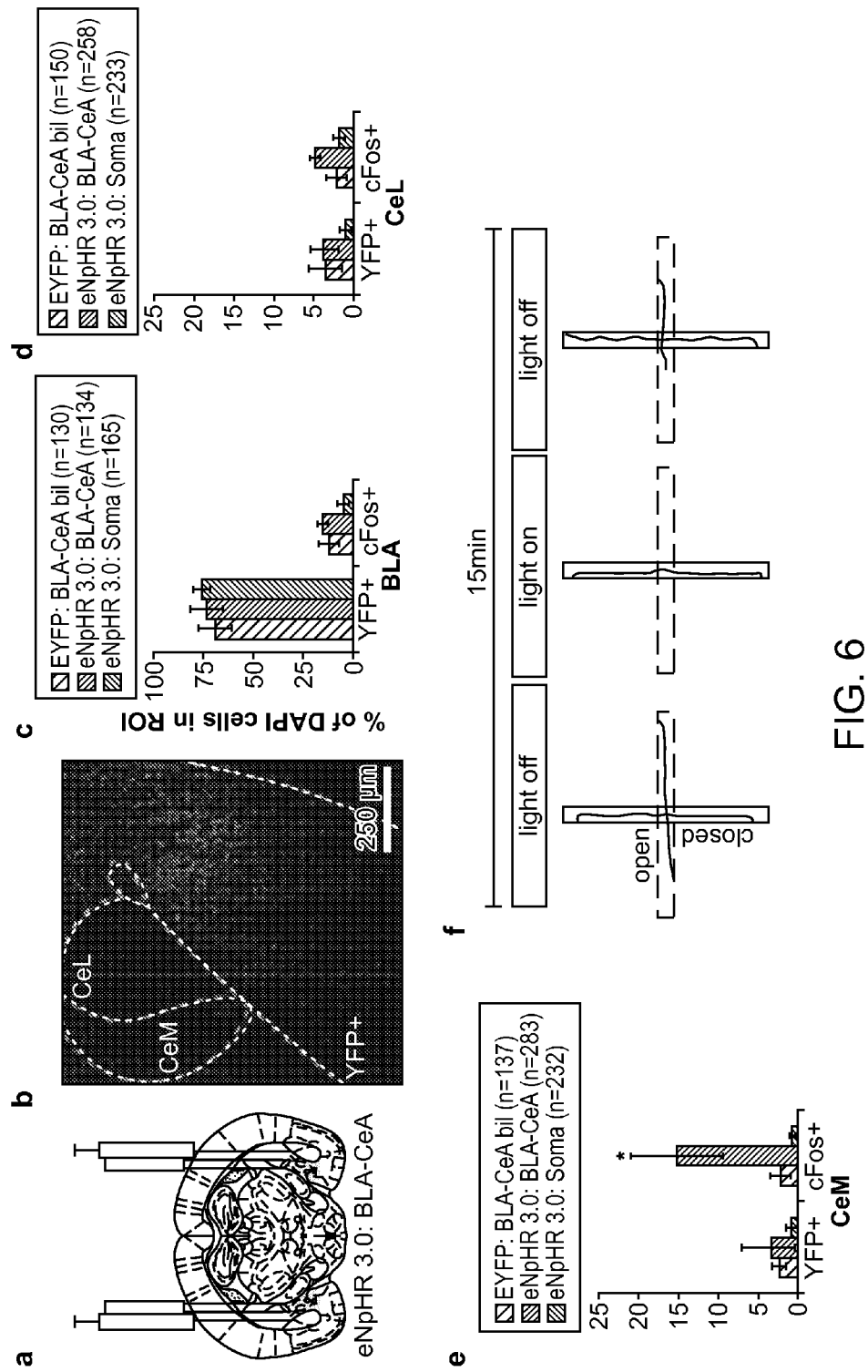
FIG. 6 shows that selective inhibition of BLA terminals in the CeA induced an acute and reversible increase in anxiety. a) All mice were group-housed in a low-stress environment and received bilateral constant 591 nm light during light on epochs. Mice in the eNpHR3.0:BLA-CeA group (n=9) received bilateral viral transduction of eNpHR3.0 in BLA neurons under the CaMKII promoter and were implanted with a beveled cannula shielding light away from BLA somata to allow selective illumination of BLA terminals in the CeA, while control groups either received bilateral virus transduction of a fluorophore only (EYFP:BLA-CeA bil group; n=8) or a light fiber directed to illuminate BLA somata (eNpHR3.0:BLA Somata group; n=6). b) Confocal image of the BLA and CeA of a mouse treated with eNpHR3.0. (c-e) In the same animals used in anxiety assays below, a significantly higher proportion of neurons in the CeM (e) from the eNpHR3.0 group expressed c-fos relative to the EYFP group (*p<0.05). f) Representative path of a mouse in the eNpHR3.0:BLA-CeA group, showing a decrease in open arm exploration on the elevated plus maze during epochs of selective illumination of BLA terminals in the CeA. g) eNpHR3.0 mice showed a reduction in the time spent in open arms and probability of open arm entry (inset) during light stimulation, relative to controls. h) Representative path of a mouse from the eNpHR3.0:BLA-CeA group during pooled light off and on epochs in the open field test. i) Significant reduction in center time in the open field chamber for the eNpHR3.0:BLA-CeA group during light on, but not light off, epochs as compared to controls, inset shows pooled data summary. (j-l) Selective illumination of eNpHR3.0-expressing BLA terminals is sufficient to reduce spontaneous vesicle release in the presence of carbachol. Representative trace of a CeL neuron (j) from an acute slice preparation in which BLA neurons expressed eNpHR 3.0, shows that when BLA terminals ~300 μm away from the BLA soma are illuminated, there is a reduction in the amplitude (k) and frequency (l) of sEPSCs seen at the postsynaptic CeL neuron. Cumulative distribution frequency of the amplitude (k) and frequency (l) of sEPSCs recorded at CeL neurons (n=5) upon various lengths of illumination 5-60 s, insets show respective mean+SEM in the epochs of matched duration before, during and after illumination (p<0.01; *p<0.001). (m-p) Selective illumination of BLA terminals expressing eNpHR 3.0 suppresses vesicle release evoked by electrical stimulation in the BLA. m) Schematic indicating the locations of the stimulating electrode, the recording electrode and the ~150 μm diameter light spot. n) Representative traces of EPSCs in a CeL neuron before ($Off_1$), during (On) and after ($Off_2$) selective illumination of BLA terminals expressing eNpHR3.0. Normalized EPSC amplitude summary data (o) and individual cell data (p) from slice preparations containing BLA neurons expressing eNpHR 3.0 (n=7) and non-transduced controls (n=5) show that selectively illuminating BLA terminals in the CeL significantly (*p=0.006) reduces the amplitude of electrically-evoked EPSCs in postsynaptic CeL neurons.

Subjects:

Male C57BL/6 mice, aged 4-6 weeks at the start of experimental procedures, were maintained with a reverse 12-hr light/dark cycle and given food and water ad libitum. Animals shown in FIGS. 3, 4 and 5 (mice in the ChR2 Terminals, EYFP Terminals and ChR2 Cell Bodies groups) were all single-housed in a typical high-traffic mouse facility to increase baseline anxiety levels. Each mouse belonged to a single treatment group. Animals shown in FIG. 6 (Bilateral EYFP and eNpHR 3.0 groups) were group-housed in a special low-traffic facility to decrease baseline anxiety levels. Animal husbandry and all aspects of experimental manipulation of our animals were in accordance with the guidelines from the National Institute of Health and have been approved by members of the Stanford Institutional Animal Care and Use Committee.

Optical Intensity Measurements:

Light transmission measurements were conducted with blocks of brain tissue from acutely sacrificed mice. The tissue was then placed over the photodetector of a power meter (ThorLabs, Newton, N.J.) to measure the light power of the laser penetrated the tissue. The tip of a 300 μm diameter optical fiber was coupled to a 473 nm blue laser (OEM Laser Systems, East Lansing, Mich.). To characterize the light transmission to the opposite side of the bevel, the photodetector of the power meter was placed parallel to the beveled cannula. For visualization of the light cone, we used Fluorescein isothiocyanate-dextran (FD150s; Sigma, Saint Louis, Mo.) at approximately 5 mg/ml placed in a cuvette with the optical fibers either with or without beveled cannula shielding aimed perpendicularly over the fluorescein solution. Power density at specific depths were calculated considering both fractional decrease in intensity due to the conical output of light from the optical fiber and the loss of light due to scattering in tissue (Aravanis et al., *J Neural Eng*, 4:S143-156, 2007) (Gradinaru et al., *J Neurosci*, 27:14231-14238, 2007). The half-angle of divergence $\theta_{div}$ for a multimode optical fiber, which determines the angular spread of the output light, is $$\theta_{div} = \sin^{-1}\left(\frac{NA_{fib}}{n_{tis}}\right)$$

where $n_{tis}$ is the index of refraction of gray matter (1.36, Vo-Dinh T 2003, Biomedical Photonics Handbook (Boca Raton, Fla.: CRC Press)) and $NA_{fib}$ (0.37) is the numerical aperture of the optical fiber. The fractional change in intensity due to the conical spread of the light with distance (z) from the fiber end was calculated using trigonometry $$\frac{I(z)}{I(z=0)} = \frac{\rho^2}{(z+\rho)}, \text{ where } \rho = r\sqrt{\left(\frac{n}{NA}\right)^2 - 1}$$

and r is the radius of the optical fiber (100 μm).

The fractional transmission of light after loss due to scattering was modeled as a hyperbolic function using empirical measurements and the Kubelka-Munk model[1, 2], and the combined product of the power density at the tip of the fiber and the fractional changes due to the conical spread and light scattering, produces the value of the power density at a specific depth below the fiber.

Virus Construction and Packaging:

The recombinant AAV vectors were serotyped with AAV$_5$ coat proteins and packaged by the viral vector core at the University of North Carolina. Viral titers were 2×10e$^{12}$ particles/mL, 3×10e$^{12}$ particles/mL, 4×10e$^{12}$ particles/mL respectively for AAV-CaMKIIα-hChR2(H134R)-EYFP, AAV-CaMKIIα-EYFP, and AAV-CaMKIIα-eNpHR 3.0-EYFP. The pAAV-CaMKIIα-eNpHR3.0-EYFP plasmid was constructed by cloning CaMKIIα-eNpHR3.0-EYFP into an AAV backbone using MluI and EcoRI restriction sites. Similarly, The pAAV-CaMKIIα-EYFP plasmid was constructed by cloning CaMKIIα-EYFP into an AAV backbone using MluI and EcoRI restriction sites. The maps are available online at www.optogenetics.org, which are incorporated herein by reference.

Stereotactic Injection and Optical Fiber Placement:

All surgeries were performed under aseptic conditions under stereotaxic guidance. Mice were anaesthetized using 1.5-3.0% isoflourane. All coordinates are relative to bregma in mm$^3$. In all experiments, both in vivo and in vitro, virus was delivered to the BLA only, and any viral expression in the CeA rendered exclusion from all experiments. Cannula guides were beveled to form a 45-55 degree angle for the restriction of the illumination to the CeA. The short side of the beveled cannula guide was placed antero-medially, the long side of the beveled cannula shielded the posterior-lateral portion of the light cone, facing the opposite direction of the viral injection needle. To preferentially target BLA- CeL synapses, we restricted opsin gene expression to BLA glutamatergic projection neurons and restricted light delivery to the CeA. Control of BLA glutamatergic projection neurons was achieved using an adeno-associated virus (AAV5) vector carrying light-activated optogenetic control genes under the control of a CaMKIIα promoter. Within the BLA, CaMKIIα is only expressed in glutamatergic pyramidal neurons, not in local interneurons[4]. Mice in the ChR2 Terminals and EYFP Terminals groups received unilateral implantations of beveled cannulae for the optical fiber (counter-balanced for hemisphere), while mice in the eNpHR 3.0 or respective EYFP group received bilateral implantations of the beveled cannulae over the CeA (−1.06 mm anteroposterior (AP); ±2.25 mm mediolateral (ML); and −4.4 mm dorsoventral (DV); PlasticsOne, Roanoke, Va.)[3]. Mice in the ChR2 Cell Bodies groups received unilateral implantation of a Doric patchcord chronically implantable fiber (NA=0.22; Doric lenses, Quebec, Canada) over the BLA at (−1.6 mm AP; ±3.1 mm ML; −4.5 mm DV)[3]. For all mice, 0.5 µl of purified $AAV_5$ was injected unilaterally or bilaterally in the BLA (±3.1 mm AP, 1.6 mm ML, −4.9 mm DV)[3] using beveled 33 or 35 gauge metal needle facing postero-lateral side to restrict the viral infusion to the BLA. 10 µl Hamilton microsyringe (nanofil; WPI, Sarasota, Fla.) were used to deliver concentrated AAV solution using a microsyringe pump (UMP3; WPI, Sarasota, Fla.) and its controller (Micro4; WPI, Sarasota, Fla.). Then, 0.5 µl of virus solution was injected at each site at a rate of 0.1 µl per min. After injection completion, the needle was lifted 0.1 mm and stayed for 10 additional minutes and then slowly withdrawn. One layer of adhesive cement (C&B metabond; Parkell, Edgewood, N.Y.) followed by cranioplastic cement (Dental cement; Stoelting, Wood Dale, Ill.) was used to secure the fiber guide system to the skull. After 20 min, the incision was closed using tissue adhesive (Vetbond; Fisher, Pittsburgh, Pa.). The animal was kept on a heating pad until it recovered from anesthesia. A dummy cap (rat: C312G, mouse: C313G) was inserted to keep the cannula guide patent. Behavioral and electrophysiological experiments were conducted 4-6 weeks later to allow for viral expression.

In Vivo Recordings:

Simultaneous optical stimulation of central amygdala (CeA) and electrical recording of basolateral amygdala (BLA) of adult male mice previously (4-6 weeks prior) transduced in BLA with AAV-CaMKIIa-ChR2-eYFP viral construct was carried out as described previously (Gradinaru et al., *J Neurosci*, 27:14231-14238, 2007). Animals were deeply anesthetized with isoflurane prior to craniotomy and had negative toe pinch. After aligning mouse stereotaxically and surgically removing approximately 3 $mm^2$ skull dorsal to amygdala. Coordinates were adjusted to allow for developmental growth of the skull and brain, as mice received surgery when they were 4-6 weeks old and experiments were performed when the mice were 8-10 weeks old (centered at −1.5 mm AP, ±2.75 mm ML)[3], a 1 Mohm 0.005-in extracellular tungsten electrode (A-M systems) was stereotactically inserted into the craniotomized brain region above the BLA (in mm: −1.65 AP, ±3.35 ML, −4.9 DV)[3]. Separately, a 0.2 N.A. 200 µm core diameter fiber optic cable (Thor Labs) was stereotactically inserted into the brain dorsal to CeA (−1.1 AP, ±2.25 ML, −4.2 DV)[3]. After acquiring a light evoked response, voltage ramps were used to vary light intensity during stimulation epochs (20 Hz, 5 ms pulse width) 2 s in length. After acquiring optically evoked signal, the exact position of the fiber was recorded, the fiber removed from the brain, inserted into a custom beveled cannula, reinserted to the same position, and the same protocol was repeated. In most trials, the fiber/cannula was then extracted from the brain, the cannula removed, and the bare fiber reinserted to ensure the fidelity of the population of neurons emitting the evoked signal. Recorded signals were bandpass filtered between 300 Hz and 20 kHz, AC amplified either 1000× or 10000× (A-M Systems 1800), and digitized (Molecular Devices Digidata 1322A) before being recorded using Clampex software (Molecular Devices). Clampex software was used for both recording field signals and controlling a 473 nm (OEM Laser Systems) solidstate laser diode source coupled to the optrode. Light power was titrated between <1 mW (~14 $mW/mm^2$) and 28 mW (~396 $mW/mm^2$) from the fiber tip and measured using a standard light power meter (ThorLabs). Electrophysiological recordings were initiated approximately 1 mm dorsal to BLA after lowering isoflurane anesthesia to a constant level of 1%. Optrode was lowered ventrally in ~0.1 mm steps until localization of optically evoked signal.

Behavioral Assays:

All animals used for behavior received viral transduction of BLA neurons and the implantation enabling unilateral (for ChR2 groups and controls) or bilateral (for eNpHR3.0 groups and controls) light delivery. For behavior, multimode optical fibers (NA 0.37; 300 µm core, BFL37-300; Thor-Labs, Newton, N.J.) were precisely cut to the optimal length for restricting the light to the CeA, which was shorter than the long edge of the beveled cannula, but longer than the shortest edge of the beveled cannula. For optical stimulation, the fiber was connected to a 473 nm or 594 nm laser diode (OEM Laser Systems, East Lansing, Mich.) through an FC/PC adapter. Laser output was controlled using a Master-8 pulse stimulator (A.M.P.I., Jerusalem, Israel) to deliver light trains at 20 Hz, 5 ms pulse-width for 473 nm light, and constant light for 594 nm light experiments. All included animals had the center of the viral injection located in the BLA, though there was sometimes leak to neighboring regions or along the needle tract. Any case in which there was any detectable viral expression in the CeA, the animals were excluded. All statistically significant effects of light were discussed, and undiscussed comparisons did not show detectable differences.

The elevated plus maze was made of plastic and consisted of two light gray open arms (30×5 cm), two black enclosed arms (30×5×30 cm) extending from a central platform (5×5×5 cm) at 90 degrees in the form of a plus. The maze was placed 30 cm above the floor. Mice were individually placed in the center. 1-5 minutes were allowed for recovery from handling before the session was initiated. Video tracking software (BiObserve, Fort Lee, N.J.) was used to track mouse location, velocity and movement of head, body and tail. All measurements displayed were relative to the mouse body. Light stimulation protocols are specified by group. ChR2:BLA-CeA mice and corresponding controls groups (EYFP:BLA-CeA and ChR2:BLA Somata) were singly-housed in a high-stress environment for at least 1 week prior to anxiety assays: unilateral illumination of BLA terminals in the CeA at 7-8 mW (~106 $mW/mm^2$ at the tip of the fiber, ~6.3 $mW/mm^2$ at CeL and ~2.4 $mW/mm^2$ at the CeM) of 473 nm light pulse trains (5 ms pulses at 20 Hz). For the ChR2 Cell Bodies group BLA neurons were directly illuminated with a lower light power because illumination with 7-8 mW induced seizure activity, so we unilaterally illuminated BLA neurons at 3-5 mW (~57 $mW/mm^2$) of 473 nm light pulse trains (5 ms pulses at 20 Hz). For the eNpHR 3.0 and corresponding EYFP group, all mice were group-housed and received bilateral viral injections and bilateral illumination of BLA terminals in the CeA at 4-6 mW (~71 mW/mm$^2$ at the tip of the fiber, ~4.7 mW/mm$^2$ at the CeL and ~1.9 mW/mm$^2$ at the CeM) of 594 nm light with constant illumination throughout the 5-min light on epoch. The 15-min session was divided into 3 5-min epochs, the first epoch there was no light stimulation (off), the second epoch light was delivered as specified above (on), and the third epoch there was no light stimulation (off).

The open-field chamber (50×50 cm) and the open field was divided into a central field (center, 23×23 cm) and an outer field (periphery). Individual mice were placed in the periphery of the field and the paths of the animals were recorded by a video camera. The total distance traveled was analyzed by using the same video-tracking software, Viewer$^2$ (BiObserve, Fort Lee, N.J.). The open field assessment was made immediately after the elevated-plus maze test. The open field test consisted of an 18-min session in which there were six 3-min epochs. The epochs alternated between no light and light stimulation periods, beginning with a light off epoch. For all analyses and charts where only "off" and "on" conditions are displayed, the 3 "off" epochs were pooled and the 3 "on" epochs were pooled.

Figure 7:
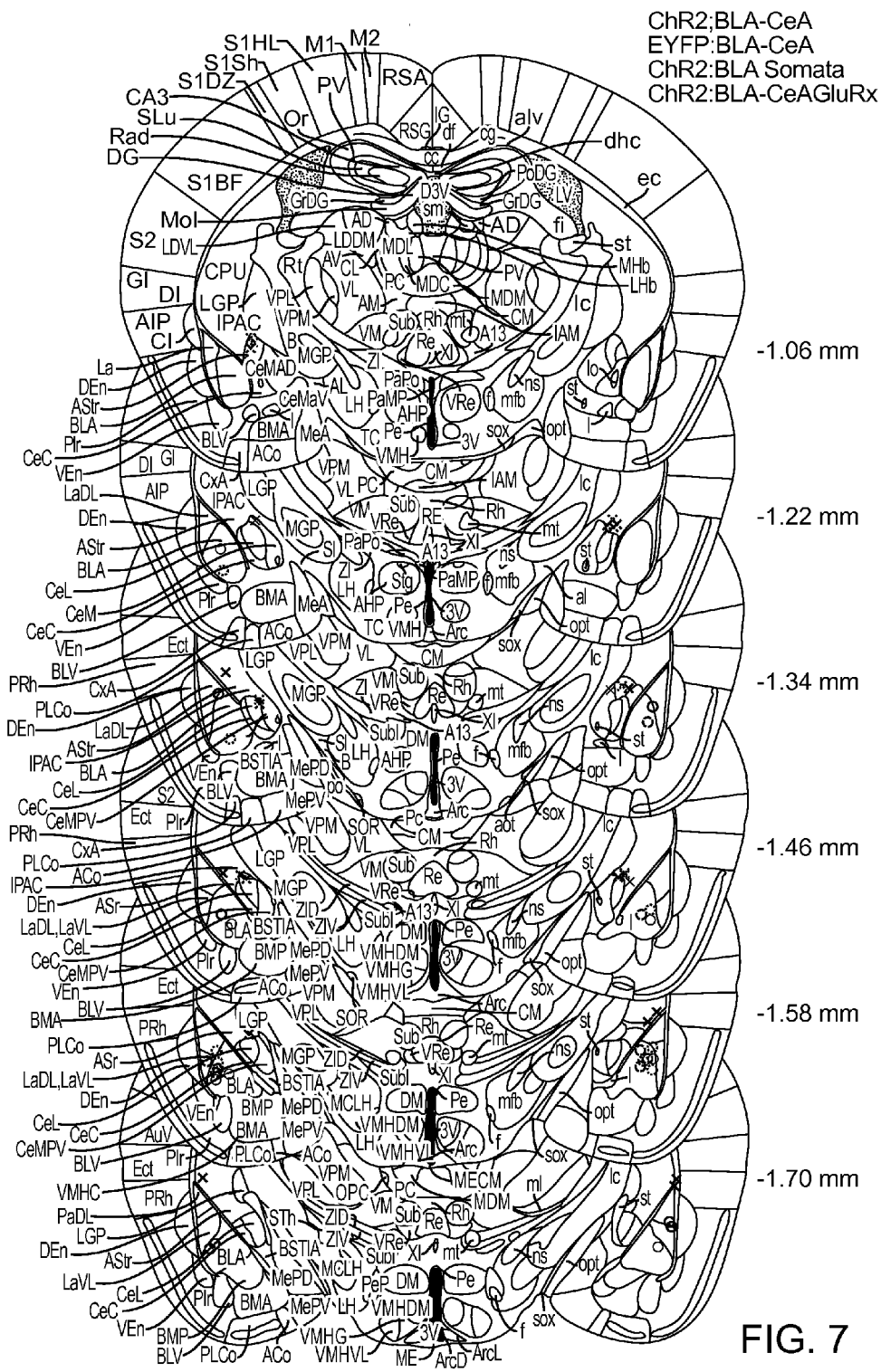
FIG. 7 is a diagram showing the histologically verified placements of mice treated with 473 nm light. Unilateral placements of the virus injection needle (circle) and the tip of beveled cannula (x) are indicated, counter-balanced for hemisphere. Colors indicate treatment group, see legend. Coronal sections containing the BLA and the CeA are shown here, numbers indicate the anteroposterior coordinates from bregma (Aravanis et al., *J Neural Eng,* 4:S143-156, 2007).
Figure 10:
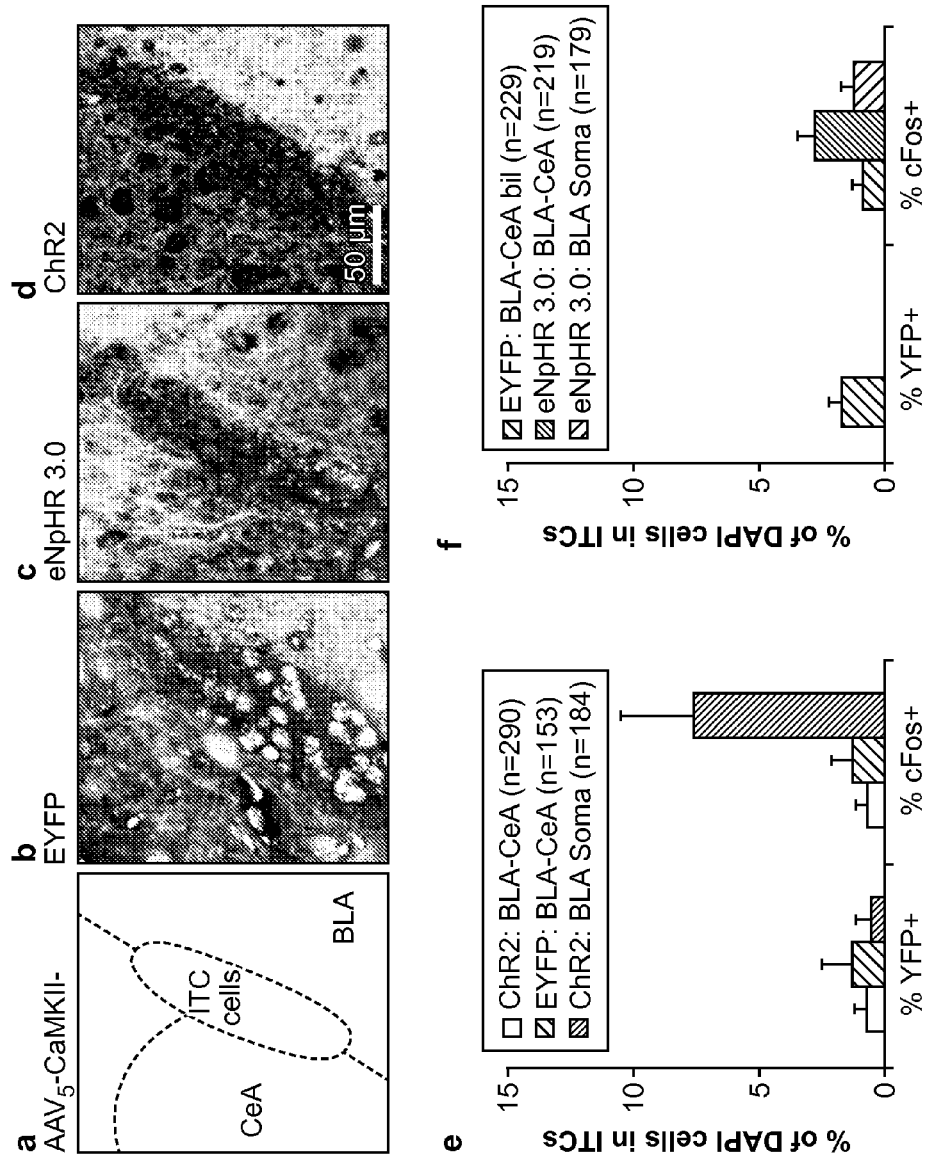
FIG. 10 demonstrates that viral transduction excluded intercalated cell clusters. a) Schematic of the intercalated cells displayed in subsequent confocal images. (b-d) Representative images of intercalated cells from mice that received EYFP b), eNpHR 3.0 c) and ChR2 d) injections into the BLA that were used for behavioral manipulations. Viral expression was not observed in intercalated cell clusters. (e-f) There were very low (<2%) levels of YFP expression in intercalated cell clusters for all 6 groups used in behavioral assays. There were no statistically significant differences among groups in c-fos expression.

For the glutamate receptor antagonist manipulation, a glutamate antagonist solution consisting of 22.0 mM of NBQX and 38.0 mM of D-APV (Tocris, Ellisville, Mo.) dissolved in saline (0.9% NaCl). 5-15 min before the anxiety assays, 0.3 µl of the glutamate antagonist solution was infused into the CeA via an internal infusion needle, inserted into the same guide cannulae used for light delivery via optical fiber, that was connected to a 10-µl Hamilton syringe (nanofil; WPI, Sarasota, Fla.). The flow rate (0.1 µl per min) was regulated by a syringe pump (Harvard Apparatus, MA). Placements of the viral injection, guide cannula and chronically-implanted fiber were histologically verified as indicated in FIGS. 7 and 10.

Two-Photon Optogenetic Circuit Mapping and Ex Vivo Electrophysiological Recording:

Mice were injected with AAV5-CaMKIIα-ChR2-EYFP at 4 weeks of age, and were sacrificed for acute slice preparation 4-6 weeks to allow for viral expression. Coronal slices containing the BLA and CeA were prepared to examine the functional connectivity between the BLA and the CeA. Two-photon images and electrophysiological recordings were made under the constant perfusion of aCSF, which contained (in mM): 126 NaCl, 26 NaHCO$_3$, 2.5 KCl, 1.25 NaH$_2$PO$_4$, 1 MgCl$_2$, 2 CaCl$_2$, and 10 glucose. All recordings were at 32° C. Patch electrodes (4-6 MOhms) were filled (in mM): 10 HEPES, 4 Mg-ATP, 0.5 MgCl$_2$, 0.4 Na$_3$-GTP, 10 NaCl, 140 potassium gluconate, and 80 Alexa-Fluor 594 hydrazide (Molecular Probes, Eugene Oreg.). Whole-cell patch-clamp recordings were performed in BLA, CeL and CeM neurons, and cells were allowed to fill for approximately 30 minutes before imaging on a modified two-photon microscope (Prairie Microscopes, Madison Wis.) where two-photon imaging, whole-cell recording and optogenetic stimulation could be done simultaneously. Series resistance of the pipettes was usually 10-20 MOhms Blue light pulses were elicited using a 473 nm LED at ~7 mW/mm$^2$ (Thorlabs, Newton N.J.) unless otherwise noted. A Coherent Ti-Saphire laser was used to image both ChR2-YFP (940 nm) and Alexa-Fluor 594 (800 nm). A FF560 dichroic with filters 630/69 and 542/27 (Semrock, Rochester N.Y.) was also used to separate both molecules' emission. All images were taken using a 40×/0.8 NA LUMPlanFL/IR Objective (Olympus, Center Valley Pa.). In order to isolate fibers projecting to CeL from the BLA and examine responses in the CeM, slices were prepared as described above with the BLA excluded from illumination. Whole-cell recordings were performed in the CeM with illumination from the objective aimed over the CeL. To further ensure activation of terminals from the BLA to CeL was selective, illumination was restricted to a ~125 µm diameter around the center of the CeL. Here, blue light pulses were elicited using an XCite halogen light source (EXPO, Mississauga, Ontario) with a 470/3 filter at 6.5 mW/mm$^2$ coupled to a shutter (Uniblitz, Rochester N.Y.). For functional mapping, we first recorded from a BLA neuron expressing ChR2 and simultaneously collected electrophysiological recordings and filled the cell with Alexa-Fluor 594 hydrazide dye to allow for two-photon imaging. Two-photon z-stacks were collected at multiple locations along the axon of the filled BLA neuron. We then followed the axon of the BLA neuron projecting to the CeL nucleus and recorded from a CeL neuron in the BLA terminal field. We then simultaneously recorded from a CeL neuron, filled the cell with dye and performed two-photon live imaging before following the CeL neuronal axons to the CeM. We then repeated this procedure in a CeM neuron, but moved the light back to the terminal field in the CeL to mimic the preferential illumination of BLA-CeL synapses with the same stimulation parameters as performed in vivo. Voltage-clamp recordings were made at both −70 mV, to isolate EPSCs, and at 0 mV, to isolate IPSCs. EPSCs were confirmed to be EPSCs via bath application of the glutamate receptor antagonists (n=5), NBQX (22 µM) and AP5 (38 µM), IPSCs were confirmed to be IPSCs via bath application of bicuculline (10 µM; n=2), which abolished them, respectively. We also performed current-clamp recordings when the cell was resting at approximately −70 mV.

For the characterization of optogenetically-driven antidromic stimulation in BLA axon terminals, animals were injected with AAV5-CaMKIIα-ChR2-EYFP at 4 weeks of age, and were sacrificed for acute slice preparation 4-6 weeks to allow for viral expression. Slice preparation was the same as above. To the aCSF we added 0.1 mM picrotoxin, 10 µM CNQX and 25 µM AP5 (Sigma, St. Louis, Mo.). Whole-cell patch-clamp recordings were performed in BLA neurons and were allowed to fill for approximately 30 minutes before two-photon imaging. Series resistance of the pipettes was usually 10-20 MOhms. All images were taken using a 40×/0.8 NA LUMPlanFL/IR Objective (Olympus, Center Valley Pa.). Blue light pulses were elicited using an XCite halogen light source (EXPO, Mississauga, Ontario) with a 470/30 filter at 6.5 mW/mm$^2$ coupled to a shutter (Uniblitz, Rochester N.Y.). Two-photon z-stacks were collected at multiple locations along the axon of the filled BLA neuron. Only neurons whose axons could be visualized for over ~300 µm diameter towards the CeL nucleus were included for the experiment, and neurons that had processes going in all directions were also excluded. Stimulation on/off axon was accomplished by moving the slice relative to a ~125 µm diameter blue light spot. In order to calibrate the slice for correct expression, whole-cell patch-clamp was performed on a CeL cell and a ~125 µm diameter spot blue pulse was used to ensure that synaptic release from the BLA terminals on to the CeL neuron was reliable.

For the dissection of direct and indirect projections to CeM, animals were injected with AAV$_5$-CaMKIIα-ChR2-EYFP at 4 weeks of age, and were sacrificed for acute slice preparation 4-6 weeks to allow for viral expression. Slice preparation was the same as above. Light was delivered through a 40×/0.8 NA LUMPlanFL/IR Objective (Olympus, Center Valley Pa.). Prior to whole cell patch clamping in the CeM nucleus, the location of the CeL nucleus was noted in order to revisit it with the light spot restricted to this region.

Whole-cell patch-clamp recordings were performed in CeM neurons. Series resistance of the pipettes was usually 10-20 MOhms. Blue light pulses were elicited using a XCite halogen light source (EXPO, Mississauga, Ontario) with a 470/30 filter at 6.5 mW/mm$^2$ coupled to a shutter (Uniblitz, Rochester N.Y.). During CeM recordings, broad illumination (~425-450 µM in diameter) of BLA terminals in the CeA and 20 Hz, 5 ms light train for 2 s was applied. Voltage-clamp recordings were made at 70 mV and 0 mV to isolate EPSCs and IPSCs respectively. Current-clamp recordings were also made. Then, illumination was moved to the CeL using a restricted light spot ~125 µm in diameter. We again performed voltage clamp recordings at −70 mV and 0 mV and used 20 Hz, 5 ms light train for 2 s. For the CeM neuron spiking inhibition experiments, in current-clamp, we applied the minimal current step required to induce spiking (~60 pA) and simultaneously applied preferential illumination of ChR2-expressing BLA terminals in the CeL with a 20 Hz, 5 ms light train for 2 s (mean over 6 sweeps per cell). For the experiments comparing the broad illumination of the BLA terminal field centered in the CeM to selective illumination of BLA-CeL terminals, these conditions were performed in repeated alternation in the same CeM cells (n=7).

To verify that terminal inhibition did not alter somatic spiking, animals were injected with AAV5-CaMKIIα-eNpHR3.0-EYFP at 4 weeks of age, and were sacrificed for acute slice preparation 4-6 weeks to allow for viral expression. Slice preparation was the same as above. Whole-cell patch-clamp recordings were performed in BLA neurons and were allowed to fill for approximately 30 minutes. Light was delivered through a 40×/0.8 NA LUMPlanFL/IR Objective (Olympus, Center Valley Pa.). Whole-cell patch-clamp recordings were performed on BLA neurons. Series resistance of the pipettes was usually 10-20 MOhms. Yellow light pulses were elicited using a XCite halogen light source (EXPO, Mississauga, Ontario) with a 589/24 filter at 6.5 mW/mm$^2$ coupled to a shutter (Uniblitz, Rochester N.Y.). After patching, an unrestricted light spot (~425-450 microns in diameter) was placed over the BLA soma and a 1 s pulse was applied. Cells were excluded if the current recorded was under 600 pA of hyperpolarizing current and the axon did not travel over ~300 µm towards the CeL nucleus. The light spot was then restricted to ~125 in diameter. On and off axon voltage clamp recordings were taken with a 1 s pulse of light. For the current clamp recordings, action potentials were generated by applying 250 pA of current to the cell soma through the patch pipette.

To demonstrate that selective illumination of eNpHR3.0-expressing BLA terminals reduced the probability of spontaneous vesicle release, animals were injected with AAV5-CaMKIIα-eNpHR3.0-EYFP at 4 weeks of age, and were sacrificed for acute slice preparation 4-6 weeks to allow for viral expression. Slice preparation was the same as above. Whole-cell patch-clamp recordings were performed in central lateral neurons. Light was delivered through a 40×/0.8 NA LUMPlanFL/IR Objective (Olympus, Center Valley Pa.). Series resistance of the pipettes was usually 10-20 MOhms Yellow light pulses were elicited using a XCite halogen light source (EXPO, Mississauga, Ontario) with a 589/24 filter at 6.5 mW/mm$^2$ coupled to a shutter (Uniblitz, Rochester N.Y.). The light spot was restricted to ~125 µm in diameter. Carbachol was added to the bath at a concentration of 20 µM. After sEPSC activity increased in the CeL neuron, light pulses were applied ranging in times from 5 s to 30 s.

To demonstrate that selective illumination of eNpHR3.0-expressing BLA terminals could reduce the probability of vesicle release evoked by electrical stimulation, animals were injected with AAV5-CaMKIIα-eNpHR3.0-EYFP at 4 weeks of age, and were sacrificed for acute slice preparation 4-6 weeks to allow for viral expression. Slice preparation was the same as above. A bipolar concentric stimulation probe (FHC, Bowdoin Me.) was placed in the BLA. Whole-cell patch-clamp recordings were performed in CeL neurons. Light was delivered through a 40×/0.8 NA LUMPlanFL/IR Objective (Olympus, Center Valley Pa.). Series resistance of the pipettes was usually 10-20 MOhms. Amber light pulses over the central lateral cell were elicited using a XCite halogen light source (EXPO, Mississauga, Ontario) with a 589/24 filter at 6.5 mW/mm$^2$ coupled to a shutter (Uniblitz, Rochester N.Y.). The light spot was restricted to ~125 µm in diameter. Electrical pulses were delivered for 40 seconds and light was delivered starting at 10 seconds and shut off at 30 seconds in the middle.

For the anatomical tracing experiments, neurons were excluded when the traced axons were observed to be severed and all BLA neurons included in the anatomical assay (FIG. 5 a-i) showed spiking patterns typical of BLA pyramidal neurons[18] upon a current step.

Slice Immunohistochemistry:

Anesthetized mice were transcardially perfused with ice-cold 4% paraformaldehyde (PFA) in PBS (pH 7.4) 100-110 min after termination of in vivo light stimulation. Brains were fixed overnight in 4% PFA and then equilibrated in 30% sucrose in PBS. 40 µm-thick coronal sections were cut on a freezing microtome and stored in cryoprotectant at 4° C. until processed for immunohistochemistry. Free-floating sections were washed in PBS and then incubated for 30 min in 0.3% Tx100 and 3% normal donkey serum (NDS). Primary antibody incubations were performed overnight at 4° C. in 3% NDS/PBS (rabbit anti-c-fos 1:500, Calbiochem, La Jolla, Calif.; mouse anti-CaMKII 1:500, Abcam, Cambridge, Mass.). Sections were then washed and incubated with secondary antibodies (1:1000) conjugated to Cy3 or Cy5 (Jackson Laboratories, West Grove, Pa.) for 3 hrs at room temperature. Following a 20 min incubation with DAPI (1:50,000) sections were washed and mounted on microscope slides with PVD-DABCO.

Confocal Microscopy and Analysis:

Confocal fluorescence images were acquired on a Leica TCS SP5 scanning laser microscope using a 20×/0.70 NA or a 40×/1.25 NA oil immersion objective. Serial stack images covering a depth of 10 µm through multiple sections were acquired using equivalent settings. The Volocity image analysis software (Improvision/PerkinElmer, Waltham, Mass.) calculated the number of c-fos positive cells per field by thresholding c-fos immunoreactivity above background levels and using the DAPI staining to delineate nuclei. All imaging and analysis was performed blind to the experimental conditions.

Statistics:

For behavioral experiments and the ex vivo electrophysiology data, binary comparisons were tested using nonparametric bootstrapped t-tests (paired or unpaired where appropriate)[5], while hypotheses involving more than two group means were tested using linear contrasts (using the "boot" and "lme4" packages in R[6], respectively); the latter were formulated as contrasts between coefficients of a linear mixed-effects model (a "two-way repeated-measures ANOVA") with the fixed-effects being the genetic or pharmacological manipulation and the light treatment (on or off). All hypothesis tests were specified a priori. Subjects were modeled as a random effects. For c-fos quantification comparisons, we used a one-way ANOVA followed by Tukey's multiple comparisons test.

Plots of the data clearly show a relationship between observation mean and observation variance (that is, they are heteroskedastic; see for example, FIG. 3e and FIG. 5j). We found that a standard square-root transformation corrected this well. Additionally, eNpHR3.0 elevated plus maze (EPM) data required detrending by a linear fit over time to account for a decrease in exploration behavior over time. As is standard for a two-way linear mixed effects model (also known as a two-way repeated-measures ANOVA), we model (the square-root corrected value of) the kth observation in the ijth cell ($y_{ijk}$) as $$\sqrt{y_{ijk}} = \mu + c_i + t_j + (c:t)_{ij} + b_j + e_{ijk} \quad (1)$$

where $\mu$ is the grand mean across all cells (where the ijth "cell" in the collection of observations corresponding to the ith condition and jth treatment)

$c_i$ is a fixed effect due to the ith animal condition across treatments (for example, a genetic manipulation)

$t_j$ is a fixed effect due to the jth treatment across conditions (for example, light on or light off)

$(c:t)_{ij}$ is a fixed effect due to the interaction of the ith condition and jth treatment in the ijth cell $b_j$ is a random effect corresponding to animals being used across treatments, and $e_{ijk}$ is an independent and identically distributed (i.i.d.) random normal disturbance in the ijkth observation with mean 0 and variance $\sigma^2$, and independent of $b_j$ for all j Collecting the fixed effects into a 2-way analysis of variance (ANOVA) design matrix $X \in \mathbb{R}^{n \times p}$, dummy coding the random effects in a sparse matrix $Z \in \mathbb{R}^{n \times q}$, and letting $\tilde{y} = \sqrt{y}$ we can express the model in matrix form as $$\tilde{y} = X\beta + Zb + e \quad (2)$$

where $\tilde{y} \in \mathbb{R}^n$, $b \in \mathbb{R}^q$, and $e \in \mathbb{R}^n$ are observations of random variables $\tilde{y}$, $\mathcal{B}$, and e respectively and our model assumes $\mathcal{B} \sim \mathcal{N}(0, \sigma^2 \Sigma)$ $e \sim \mathcal{N}(0, \sigma^2 I), e \perp \mathcal{B}$ $(\tilde{y} | \mathcal{B} = b) \sim \mathcal{N}(X\beta + Zb, \sigma^2 I)$ where N $(\mu, \Sigma)$ denotes the multivariate Gaussian distribution with mean vector $\mu$ and variance-covariance matrix $\Sigma$, and $\perp$ indicates that two variables are independent. To estimate the coefficient vectors $\beta \in \mathbb{R}^p$, $b \in \mathbb{R}^q$, and the variance parameter $\sigma$ and sparse (block-diagonal) relative variance-covariance matrix $\Sigma \in \mathbb{R}^{q \times q}$, we use the lme4 package in R written by Douglas Bates and Martin Maechler, which first finds a linear change of coordinates that "spheres" the random effects and then finds the maximum likelihood estimates for $\beta$, $\sigma$, and $\Sigma$ using penalized iteratively reweighted least-squares, exploiting the sparsity of the random effects matrix to speed computation. For more details see the documentation accompanying the package in the lme4 repository at http://www.r-project.org/.

To solve for the maximum likelihood estimates, the design matrix X in equation 2 must be of full column rank. It is well known that this is not the case for a full factorial design matrix with an intercept (as in equation 1), and thus linear combinations ("contrasts") must be used to define the columns of X in order for the fixed-effect coefficients to be estimable. As our designs are balanced (or nearly balanced), we used orthogonal (or nearly orthogonal) Helmert contrasts between the coefficients associated with light on as compared to light off conditions, terminal stimulation as compared to control conditions, and so on, as reported in the main text. Such contrasts allowed us to compare pooled data (e.g., from several sequential light on vs. light off conditions) against each other within a repeated-measures design—yielding improved parameter estimation and test power while accounting for within-animal correlations.

Results

Figure 8:
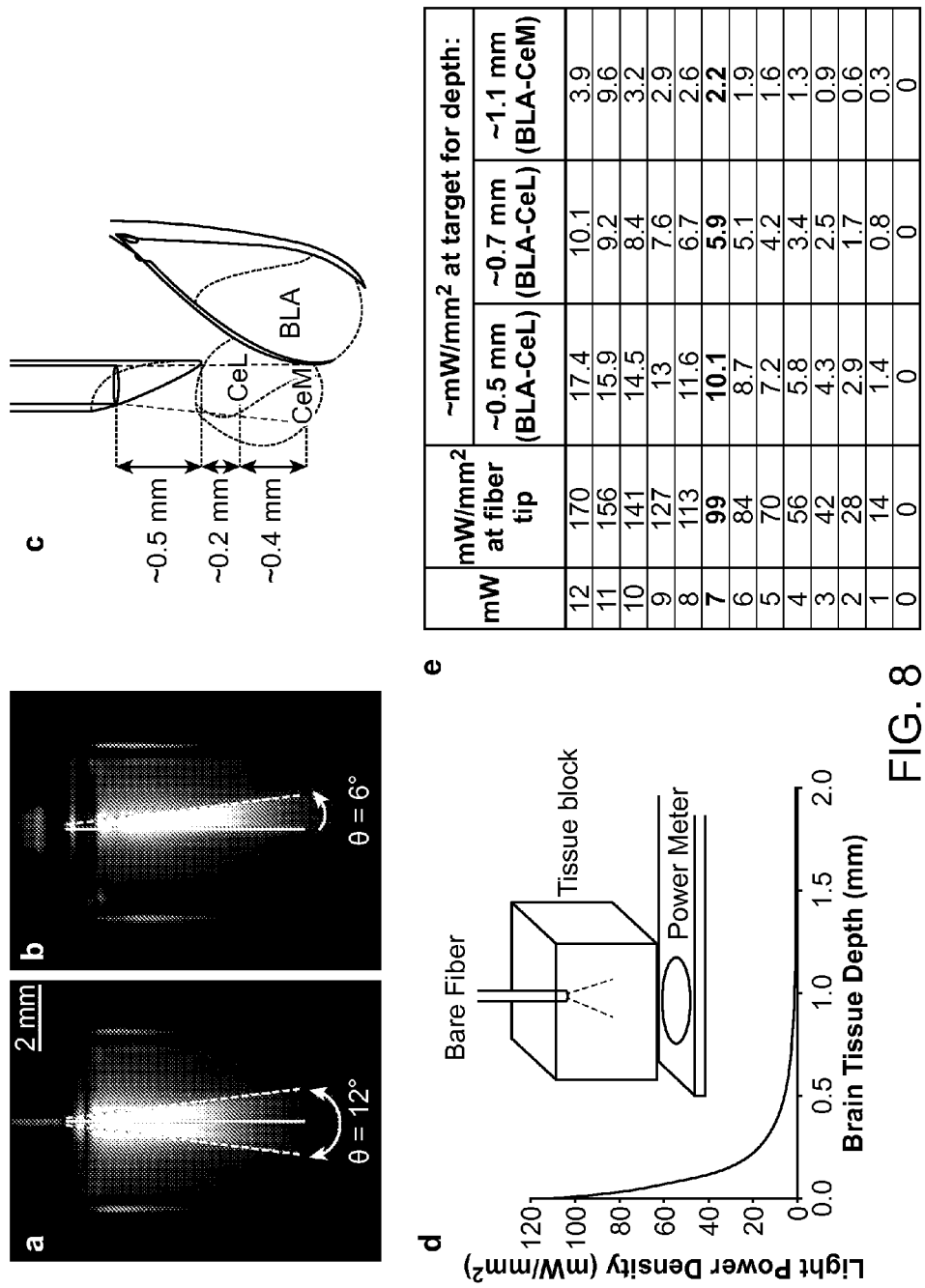
FIG. 8 shows the beveled cannula and illumination profile design. a) Light cone from bare fiber emitting 473 nm light over cuvette filled with fluorescein in water. The angle of the light cone is approximately 12 degrees. b) Light cone from the same fiber and light ensheathed in a beveled cannula. The beveled cannula blocks light delivery to one side, without detectably altering perpendicular light penetrance. c) Diagram of light delivery via the optical fiber with the beveled cannula over CeA. d) Chart indicating estimated light power density seen at various distances from the fiber tip in mouse brain tissue when the light power density seen at the fiber tip was 7 mW (~99 mW/mm$^2$). Inset, cartoon indicating the configuration. Optical fiber is perpendicular and aimed at the center of the power meter, through a block of mouse brain tissue. e) Table showing light power (mW) as measured by a standard power meter and the estimated light power density (mW/mm$^2$) seen at the tip, at the CeL (~0.5-0.7 mm depth in brain tissue) and at the CeM (~1.1 mm depth in brain tissue).
Figure 9:
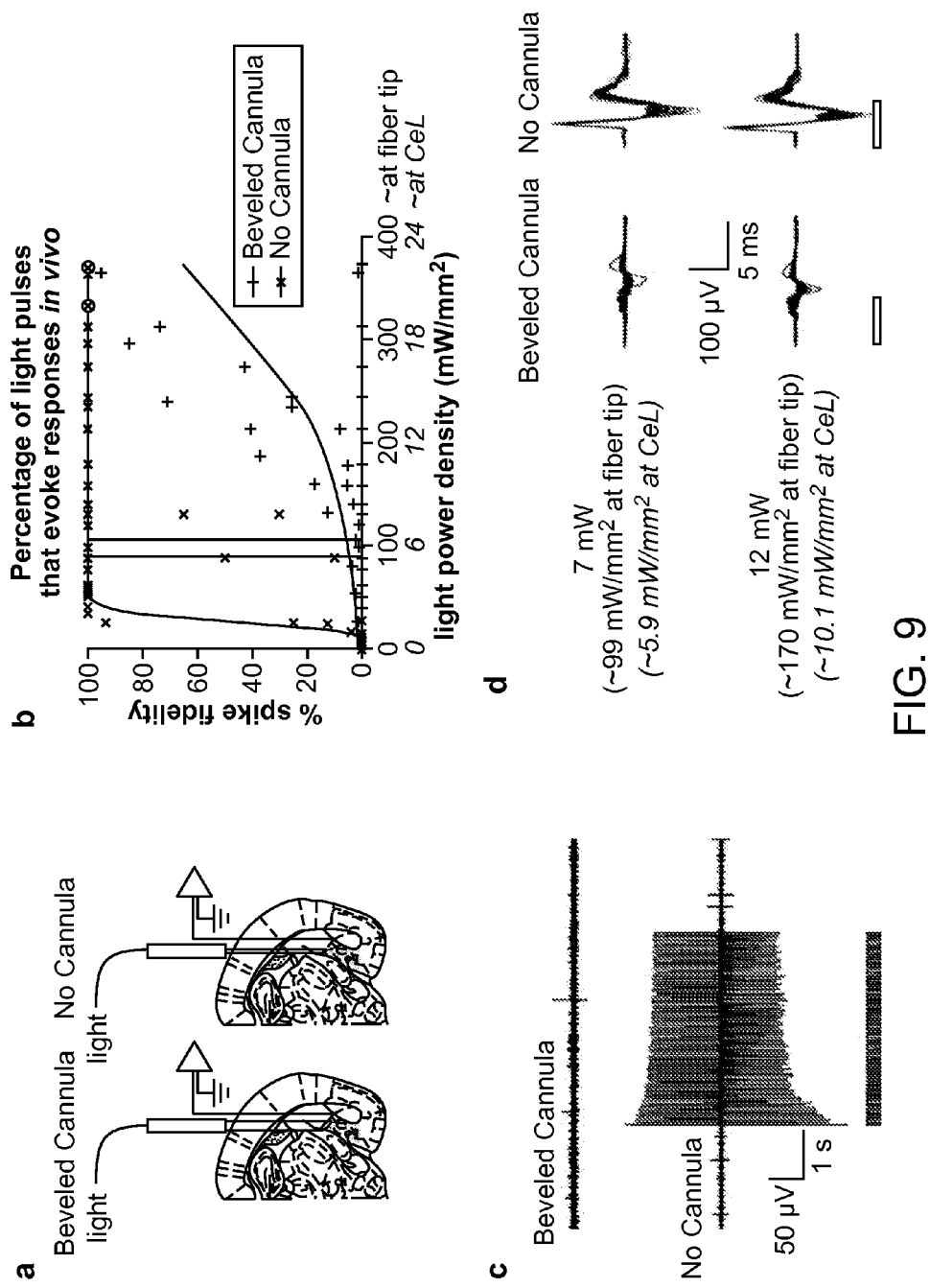
FIG. 9 demonstrates that the beveled cannula prevented light delivery to BLA and BLA spiking at light powers used for behavioral assays. a) Schematic indicating the configuration of light delivery by optical fiber to the CeA and recording electrode (red) in the BLA. b) Scatterplot summary of recordings in the BLA with various light powers delivered to the CeA with and without the beveled cannula (n=4 sites). For each site, repeated alternations of recordings were made with and without the beveled cannula. The x-axis shows both the light power density at the fiber tip (black) and the estimated light power density at the CeL (grey). The blue vertical or shaded region indicates the range of light power densities used for behavioral assays (~7 mW; ~99 mW/mm$^2$ at the tip of the fiber). Reliable responses from BLA neurons were not observed in this light power density range. c) Representative traces of BLA recordings with 20 Hz 5 ms pulse light stimulation at 7 mW (~99 mW/mm$^2$ at fiber tip; ~5.9 mW/mm$^2$ at CeL) at the same recording site in the CeA. d) Population spike waveforms in response to single pulses of light reveal substantial light restriction even at high 12 mV power (~170 mW/mm$^2$ at the tip of the fiber; ~10.1 mW/mm$^2$ at CeL).

BLA cells have promiscuous projections throughout the brain, including to the bed nucleus of the stria terminalis (BNST), nucleus accumbens, hippocampus and cortex[38, 43]. To test whether BLA-CeL synapses could be causally involved in anxiety, it was therefore necessary to develop a method to selectively control BLA terminals in the CeL, without directly affecting other BLA projections. To preferentially target BLA-CeL synapses, we restricted opsin gene expression to BLA glutamatergic projection neurons and restricted light delivery to the CeA. Control of BLA glutamatergic projection neurons was achieved with an adeno-associated virus (AAV5) vector carrying light-activated optogenetic control genes under the control of a CaMKIIα promoter; within the BLA, CaMKIIα is only expressed in glutamatergic pyramidal neurons, not in local interneurons or intercalated cells[48]. To preferentially deliver light to the CeA projection, virus was delivered unilaterally into the BLA under stereotaxic guidance (FIGS. 7 and 8) along with implantation of a beveled guide cannula over the CeL to prevent light delivery to the BLA and allow selective illumination of the CeA. Geometric and functional properties of the resulting light distribution were quantified both in vitro and in vivo, with in vivo electrophysiological recordings to determine light power parameters for selective control of BLA terminals but not BLA cell bodies (FIG. 9).

To test the hypothesis that the BLA-CeA pathway could implement an endogenous mechanism for anxiolysis, we probed freely-moving mice under projection-specific optogenetic control in two distinct and well-validated anxiety assays: the elevated plus maze and the open field test (FIG. 3a-f). Mice display anxiety-related behaviors when exposed to open or exposed spaces, therefore increased time spent in the exposed arms of the elevated plus maze or in the center of the open field chamber indicates reduced anxiety[49, 50]. To test for both induction and reversal of relevant behaviors, we first exposed mice to the elevated plus maze for three 5-min epochs, in which light was delivered during the second epoch only.

To determine whether the anxiolytic effect we observed would be specific to activation of BLA terminals in the CeA, and not BLA cells in general, we compared mice receiving projection-specific control (in the ChR2:BLA-CeA group; FIG. 3a) to both a negative control group receiving transduction with a control virus given the same pattern of illumination (EYFP:BLA-CeA) and a positive control group transduced with the AAV-CaMKIIα-ChR2-EYFP virus in the BLA with a fiber implanted directly over the BLA (ChR2:BLA Somata). For this group (ChR2:BLA Somata), light stimulation did not elicit the anxiolysis observed in the ChR2:BLA-CeA group (FIGS. 3b and c); indeed, the ChR2:BLA-CeA group spent significantly more time in open arms (t(42)=8.312; p<0.00001; FIG. 3b,c) during light-induced activation of BLA terminals in the CeA, in comparison to controls (EYFP:BLA-CeA and ChR2:BLA Somata groups). The ChR2:BLA-CeA mice also showed an increase in the probability of entering an open arm rather than a closed arm, from the choice point of the center of the maze (FIG. 3c inset), indicating an increased probability of selecting the normally anxiogenic environment.

We also probed mice on the open field arena for six 3-minute epochs, again testing for reversibility by alternating between no light (off) and light stimulation (on) conditions. Experimental (ChR2:BLA-CeA) mice displayed an immediate, robust, and reversible light-induced anxiolytic response as measured by the time in center of the open field chamber (FIGS. 3d and e), while mice in the EYFP:BLA-CeA and ChR2:BLA Somata groups did not (FIG. 3e). Light stimulation did not significantly alter locomotor activity (FIG. 3f). While there was no detectable difference among groups in the off conditions, there was a significant increase in center time of the open field spent by mice in the ChR2:BLA-CeA group relative to the EYFP:BLA-CeA or ChR2:BLA Somata groups during the on conditions (t(105) =4.96178; p<0.0001 for each contrast). We concluded that selective stimulation of BLA projections to the CeA, but not BLA somata, produces an acute, rapidly reversible anxiolytic effect, supporting the hypothesis that the BLA-CeL-CeM pathway could represent a native microcircuit for anxiety control.

We next investigated the physiological basis of this light-induced anxiolytic effect. Glutamatergic neurons in the BLA send robust excitatory projections to CeL neurons as well as to CeM neurons[38]; however, not only are the CeM synapses distant from the light source (FIG. 8), but also any residual direct excitation of these CeM neurons would be expected to result in an anxiogenic, rather than an anxiolytic, effect[12]. However, CeL neurons exert strong inhibition onto these brainstem-projecting CeM output neurons[32, 35, 40], and we therefore hypothesized that illumination of BLA terminals in the CeA could activate BLA-CeL neurons and thereby elicit feed-forward inhibition onto CeM neurons and implement the observed anxiolytic phenomenon.

To confirm the operation of this optogenetically-defined projection, we undertook in vivo experiments, with light delivery protocols matched to those delivered in the behavioral experiments, and activity-dependent immediate early gene (c-fos) expression analysis as the readout to verify the pattern of neuronal activation (FIG. 3g-k). Under blinded conditions, we quantified the proportion of neurons in the BLA, CeL and CeM (FIG. 3i-k) for ChR2:BLA-CeA, EYFP:BLA-CeA and ChR2:BLA Somata groups that expressed EYFP or showed c-fos immunoreactivity. Virus expression under the CaMKIIα promoter in the BLA targeted glutamatergic neurons[47], and we did not observe EYFP expression in local interneurons nor intercalated cells (FIG. 10). No significant differences among groups were detected in the proportion of EYFP-positive cells within each region (FIG. 3g-k), but we found a significantly higher proportion of c-fos positive BLA cells in the ChR2:BLA Somata group, relative to ChR2:BLA-CeA or EYFP:BLA-CeA groups (FIG. 3i; p<0.01 and p<0.05, respectively). There was no detectable difference in c-fos between the ChR2:BLA-CeA and EYFP:BLA-CeA groups, indicating that the beveled cannula shielding effectively prevented direct illumination to BLA cell bodies. A significantly higher proportion of CeL neurons expressed c-fos in the ChR2:BLA-CeA group relative to the EYFP:BLA-CeA group (p<0.05), but not the ChR2:BLA Somata group (FIG. 3j). Thus, selective illumination of BLA terminals expressing ChR2 in the CeA led to preferential activation of CeL neurons, without activating BLA somata. In the CeM, we found twice as many c-fos positive neurons (relative to total neurons) in the ChR2:BLA Somata group than in the ChR2:BLA-CeA (FIG. 3k), consistent with anatomical projections, as LA neurons selectively innervate CeL neurons, while neurons in the BL and BM nuclei of the amygdala have monosynaptic projections to both the CeL and the CeM[38, 43, 51]. Together, these data reveal that the in vivo illumination that triggers an acute anxiolytic behavioral phenotype implements selective illumination of BLA-CeL synapses without activating BLA cell bodies.

To test the hypothesis that selective illumination of BLA terminals in the CeL induces feed-forward inhibition of CeM output neurons, we combined whole-cell patch-clamp recording with live two-photon imaging to visualize the microcircuit while simultaneously probing the functional relationships among these cells during projection-specific optogenetic control (FIG. 4a-f). While the light-stimulation parameters used in vivo were delivered via a fiber optic and the parameters used in our ex vivo experiments were delivered onto acute slices, we matched the light power density at our target location ~6 mW/mm². A two-photon image of the BLA-CeL-CeM circuit is shown in FIG. 4a, with all three cells imaged from the same slice (FIG. 4a). The BLA neuron expressing ChR2-EYFP showed robust, high-fidelity spiking to direct illumination with 20 Hz, 5 ms pulses of 473 nm light (FIG. 4b). A representative trace from a CeL neuron, recorded during illumination of the terminal field of BLA neurons expressing ChR2-EYFP, demonstrates the typical excitatory responses seen in CeL (FIG. 4c), with population summaries revealing that spiking fidelity was steady throughout the 40-pulse light train and that responding cells include both weakly and strongly-excited CeL cells (n=16; FIG. 4c). To test whether illumination of BLA-CeL synapses would be functionally significant at the level of blocking spiking in CeM cells due to the robust feed-forward inhibition from CeL neurons, we recorded from CeM neurons while selectively illuminating BLA-CeL synapses (FIG. 4d). Indeed, we observed potent spiking inhibition ($F_{2,11}$=15.35, p=0.0044) in the CeM due to light stimulation of BLA terminals in the CeL (FIG. 4d; spikes per second before (49±9.0), during (1.5±0.87), and after (33±8.4) illumination; mean±s.e.m). Next, FIG. 4e shows CeM responses recorded during illumination of the terminal field of BLA neurons in the CeM expressing ChR2-EYFP, and the combined excitatory and inhibitory input. Population summaries from voltage-clamp recordings indicated that latencies of EPSCs were shorter than those of the disynaptic IPSCs, as expected, and that the mean IPSC amplitude was greater than mean EPSC amplitude (recorded at 0 and −70 mV, respectively; FIG. 4e). Importantly, the very same CeM neurons (n=7) yielded net excitation with broad illumination of BLA inputs to the CeM (FIG. 4e), but displayed net inhibition with selective illumination of BLA inputs to the CeL (FIG. 4f) in a repeatable fashion with alternation between sites. This demonstrates that the balance of direct and indirect inputs from the BLA to the CeM can modulate CeM output. Together, these data reveal a structurally- and functionally-identified physiological microcircuit, whereby selective illumination of BLA terminals in the CeA activates BLA-CeL synapses, thus increasing feed-forward inhibition from CeL neurons onto the brainstem-projecting CeM neurons.

To further elucidate the amygdalar microcircuits underlying this anxiolytic effect, we carefully dissected the anatomical and functional properties governing this phenomenon. While some efforts to map the projections of BLA collaterals in the CeA have been made in the rat, we empirically tested whether overlapping or distinct populations of BLA neurons projected to the CeL and CeM (FIG. 5a,b). A noteworthy caveat is that we visualized these neurons in ~350 um thick coronal sections and while every attempt was made to exclude neurons in which the axons were severed, we cannot exclude the possibility that this occurred nor can we deny that this induced some sampling bias for BLA neurons closer to the CeA. FIG. 5a summarizes the anatomical projections of the BLA neurons sampled (n=18) and shows that the 44% of neurons projected to the CeL alone and 17% projected to the CeM alone. However, a minority of BLA cells (n=1; 6%), projected to both the CeL and the CeM, one of which sent separate collaterals to the CeL and CeM and one of which sent a collateral that sent branches to the CeL and CeM. FIG. 5b shows the 2-photon image of each cell sampled, all of which showed spiking patterns typical of BLA pyramidal neurons upon a current step.

Figure 15:
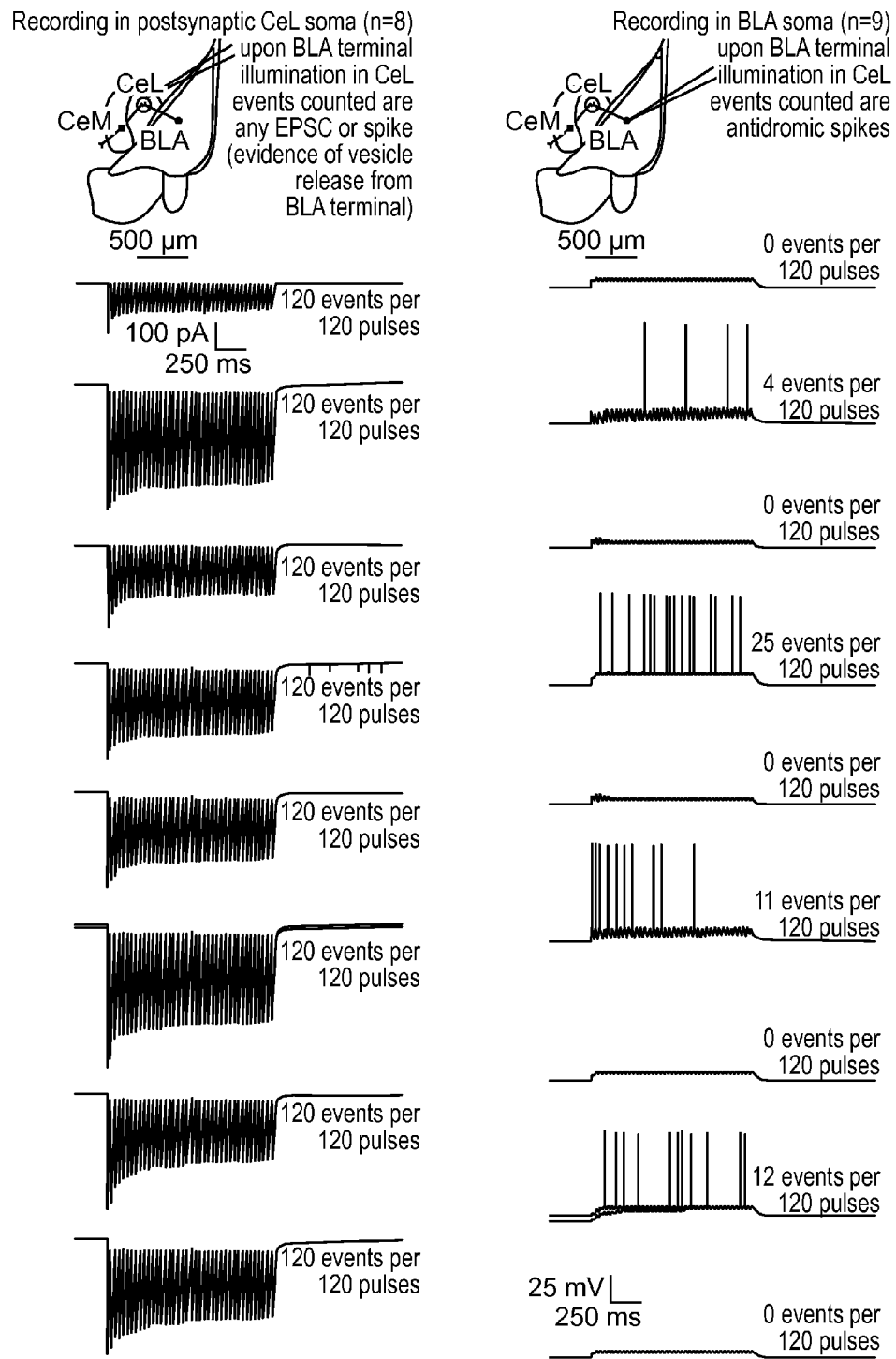
FIG. 15 demonstrates that selective illumination of BLA terminals induced vesicle release onto CeL neurons without reliably eliciting antidromic action potentials. Schematics and descriptions refer to the traces below, and trace color indicates cell type. Light illumination patterns are identical for both series of traces. Left column, CeL traces for three overlaid sweeps of a 40-pulse light train per cell (n=8). Here, both time-locked EPSCs indicate vesicle release from the presynaptic ChR2-expressing BLA terminal, and for all postsynaptic CeL cells, there were excitatory responses to 100% of light pulses. Right column, BLA traces for three overlaid 40-pulse sweeps per cell (n=9), with the mean number of light pulses delivered at the axon terminal resulting in a supra-threshold antidromic action potential (5.4%±2%, mean±SEM).

Next, as our c-fos assays suggested that illumination of BLA terminals in the CeL were sufficient to excite CeL neurons, but not BLA neurons themselves, we sought to confirm this hypothesis with whole-cell recordings. With electrical stimulation, depolarization of axon terminals leads to antidromic spiking at the cell soma. However, there has been evidence that optogenetically-induced depolarization functions via a distinct mechanism. To evaluate the properties of optogenetically-induced terminal stimulation in this amygdalar microcircuit, we recorded from BLA pyramidal neurons expressing ChR2 and moved a light spot (~120 μm in diameter) in 100 μm steps from the cell soma, both in a direction over a visually-identified axon collateral and in a direction where there was no axon (FIG. 5c). The spike fidelity of the BLA neuron given a 20 Hz train of light at each distance from the soma is summarized in FIG. 5d, while the depolarizing current is summarized in FIG. 5e. In all preparations, we confirmed that the light stimulation parameters used were sufficient to elicit high-fidelity spiking at the BLA cell soma (FIG. 5f) and reliable vesicle release at BLA terminals as shown by recordings from a postsynaptic CeL neuron (FIG. 5g; FIG. 15). In contrast, when recording from the same BLA neurons with the light spot 300 um away from the cell soma we did not observe reliable action potential induction, regardless of whether we were over an axon (FIG. 5h) or not (FIG. 5i). This absence of antidromic spiking was observed even upon bath application of GABA and AMPA receptor antagonists (n=7), thus excluding the possible contribution of local inhibitory constraints. While we demonstrate that optogenetically-induced vesicle release can occur in the absence of antidromic stimulation in BLA pyramidal neurons, it is possible that at antidromic stimulation could be achieved with greater light power density than we used here (~6 mW/mm$^2$) Thus far, we have demonstrated that the populations of BLA neurons projecting to the CeL and the CeM are largely distinct and that illumination of BLA-CeL synapses induces vesicle release and CeL excitation without strong activation of BLA somata themselves.

Figure 11:
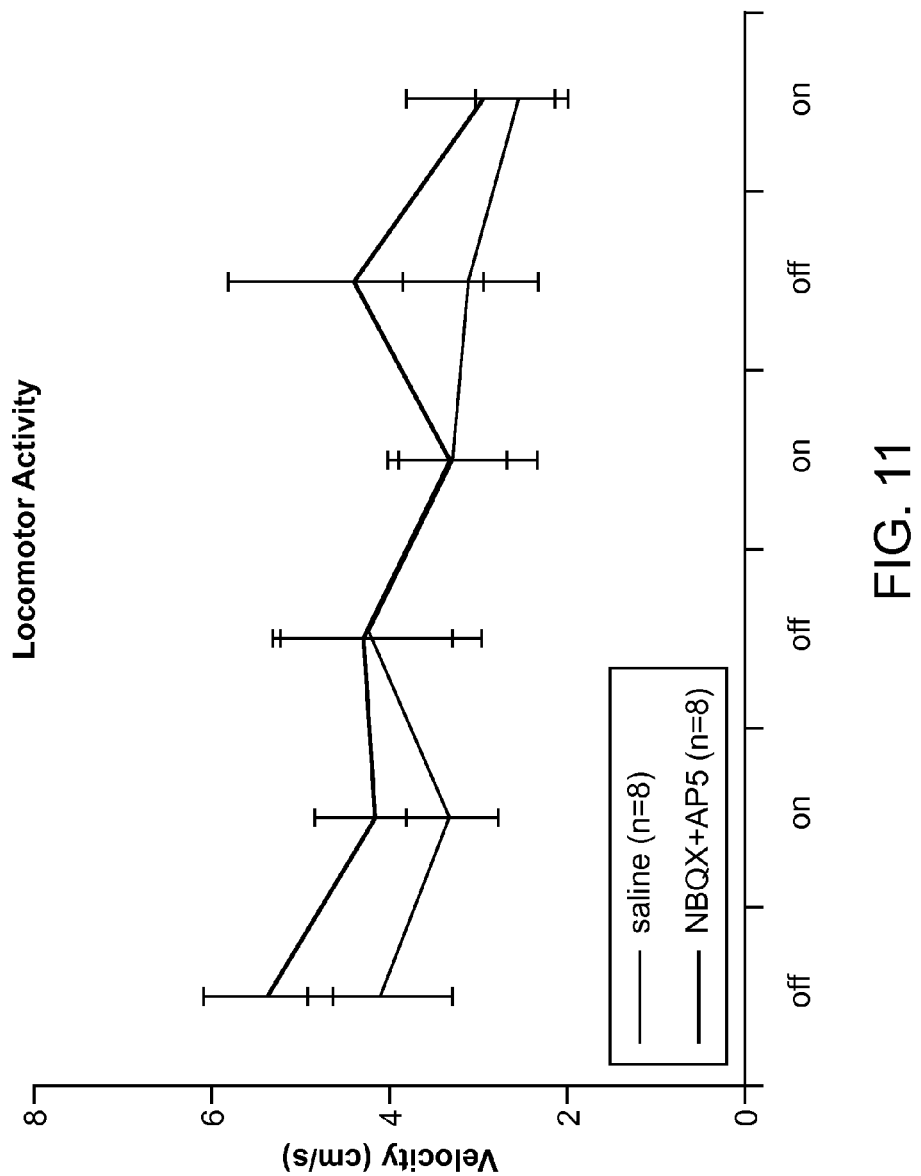
FIG. 11 shows that unilateral intra-CeA administration of glutamate antagonists did not alter locomotor activity. Administration of NBQX and AP5 prior to the open field test did not impair locomotor activity (as measured by mean velocity) relative to saline infusion ($F_{1,77}$=2.34, p=0.1239).
Figure 12:
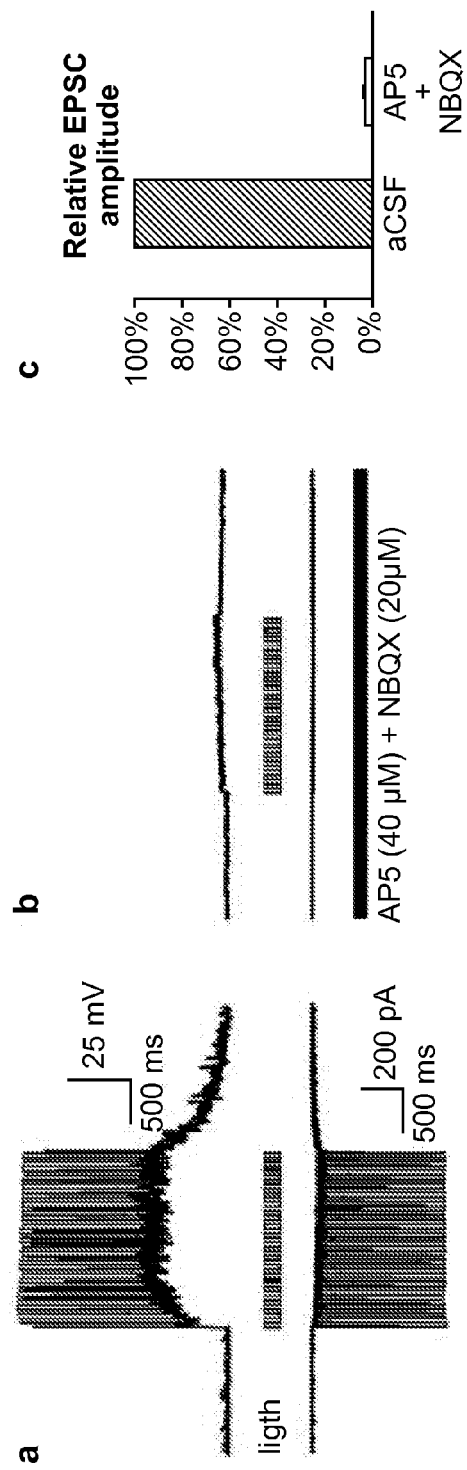
FIG. 12 demonstrates that bath application of glutamate antagonists blocked optically-evoked synaptic transmission. 4-6 weeks following intra-BLA infusions of AAV5-CamKII-ChR2-EYFP into the BLA of wild-type mice, we examined the ability of the glutamate receptor antagonists NBQX and AP5 to block glutamatergic transmission. a) Representative current-clamp (top) and voltage-clamp (bottom) traces of a representative CeL neuron upon a 20 Hz train of 473 nm light illumination of BLA terminals expressing ChR2. b) The same cell's responses following bath application of NBQX and AP5 show abolished spiking and EPSCs. c) Population summary (n=5) of the depolarizing current seen before and after bath application of NBQX and AP5, normalized to the pre-drug response.

Finally, we further explored the mechanism with in vivo pharmacological analysis in the setting of projection-specific optogenetic control. To determine whether the anxiolytic effect we observed could be due to the selective activation of BLA-CeL synapses alone, and not BLA fibers passing through the CeA, nor back-propagation of action potentials to BLA cell bodies which then would innervate all BLA projection target regions, we tested whether local glutamate receptor antagonism would attenuate light-induced anxiolytic effects. This question is of substantial interest since lesions in the CeA that alter anxiety are confounded by the likelihood of ablation of BLA projections to the BNST which pass through CeA[6]. We unilaterally transduced BLA neurons with AAV-CaMKIIα-ChR2-EYFP and implanted beveled cannulae to implement selective illumination of BLA terminals in the CeA as before (n=8; FIG. 8), and tested mice on the elevated plus maze and open field test. In this case, however, we infused either the glutamate antagonists NBQX and AP5 using the optical fiber guide cannula, or saline control on different trials in the same animals, with trials counter-balanced for order. Confirming a local synaptic mechanism rather than control of fibers of passage, for the same mice and light stimulation parameters, local glutamate receptor antagonism in the CeA abolished light-induced reductions in anxiety on both the elevated plus maze (FIG. 5k) and the open field test (FIG. 5j). Importantly, in control experiments, drug treatment did not impair locomotor activity (FIG. 11), and in acute slices time-locked light-evoked excitatory responses were abolished upon bath application of NBQX and AP5 (FIG. 12). Together these data indicate that the light-induced anxiolytic effects we observed were caused by the activation of BLA-CeL synapses, and not attributable to BLA projections to distal targets passing through the CeA.

Figure 13:
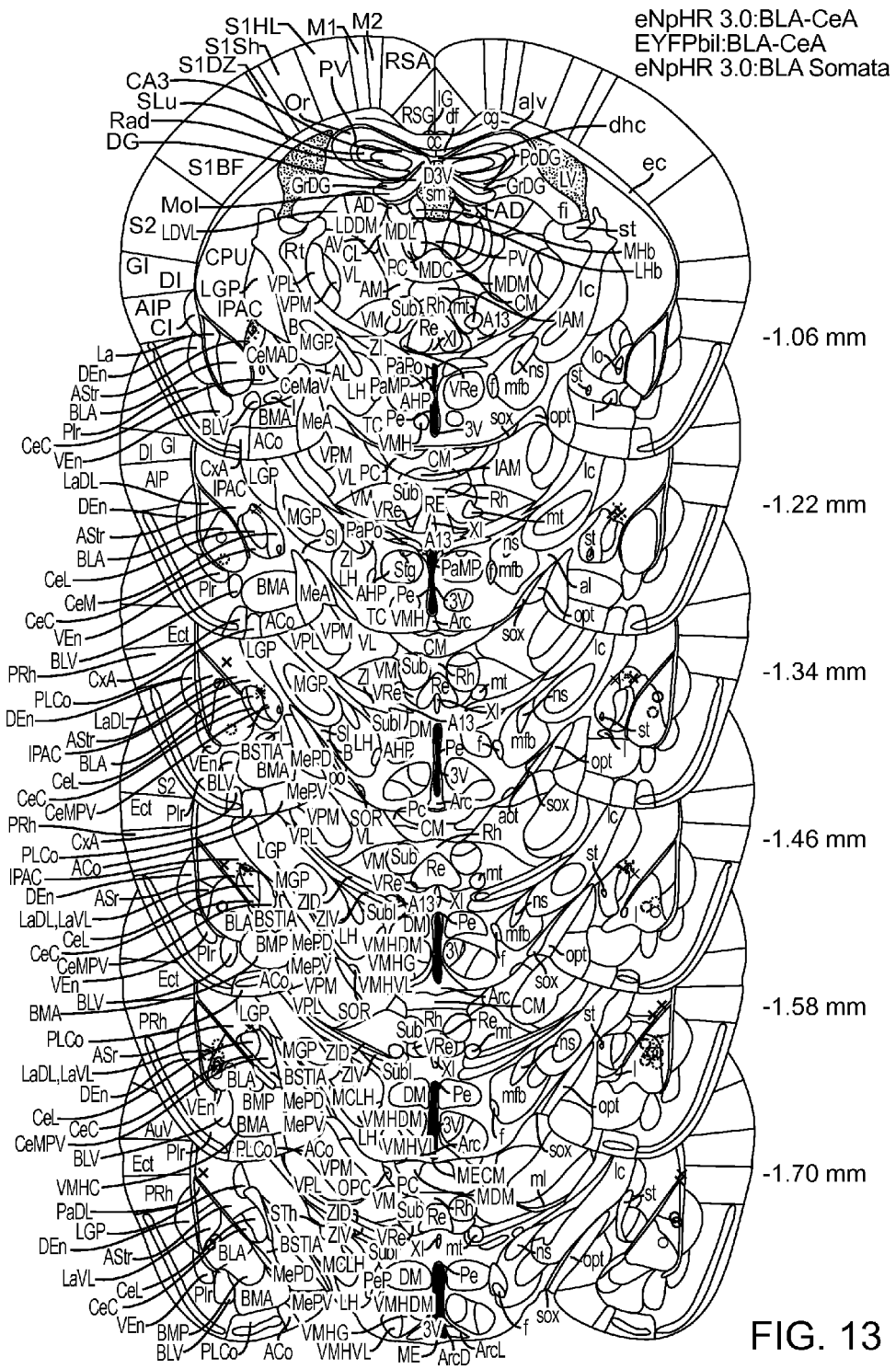
FIG. 13 is a diagram depicting the histologically verified placements of mice treated with 594 nm light. Bilateral placements of virus injection needle (circle) and tip of beveled cannula (x) are indicated. Colors indicate treatment group, see legend. Coronal sections containing BLA and CeA are shown; numbers indicate AP coordinates from bregma (Aravanis et al., *J Neural Eng,* 4:S143-156, 2007).
Figure 14:
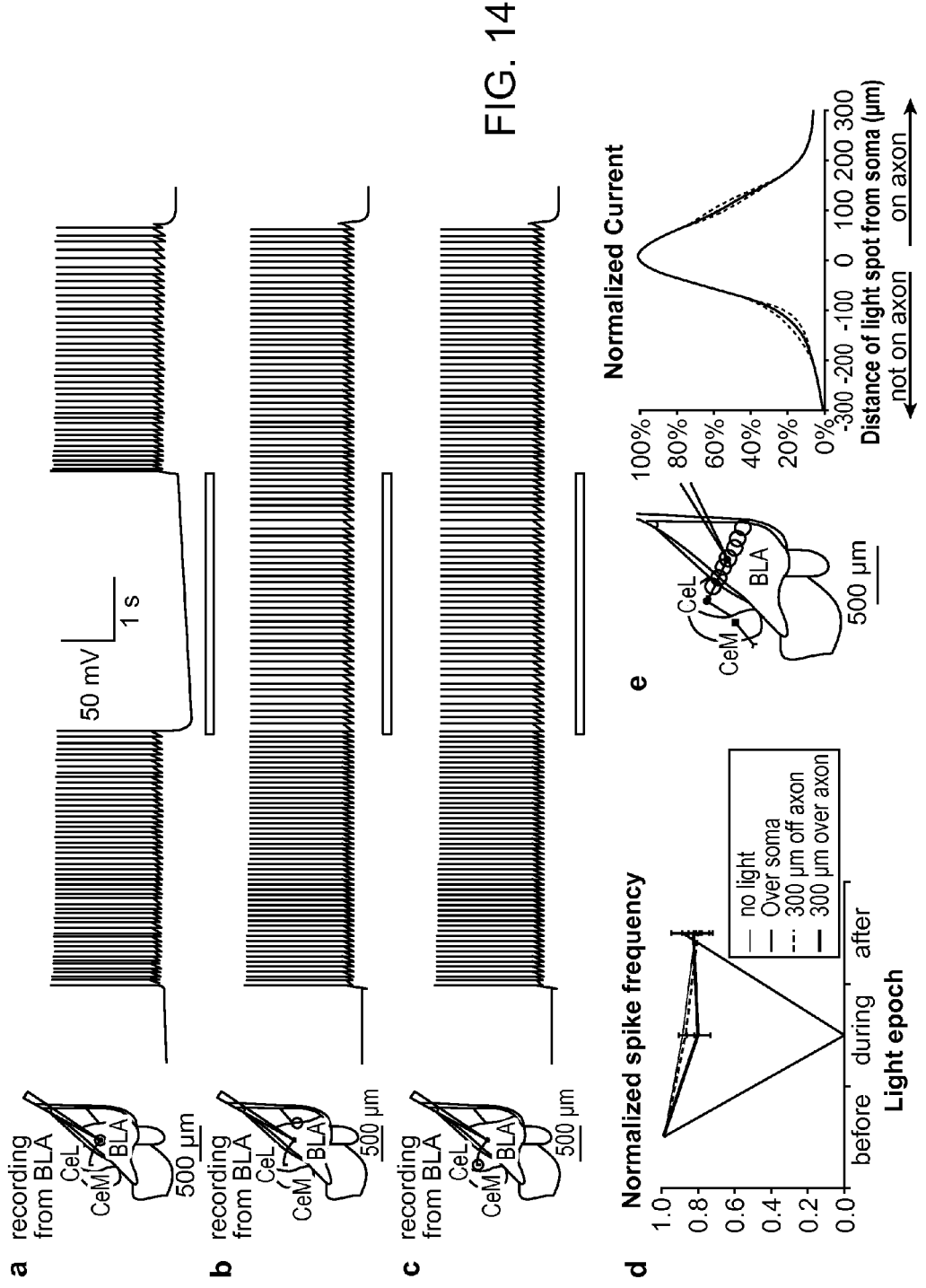
FIG. 14 shows that light stimulation parameters used in the eNpHR 3.0 terminal inhibition experiments does not block spiking at the cell soma. (a-c) Schematics of the light spot location and recording sites alongside corresponding representative traces upon a current step lasting the duration of the spike train, paired with yellow light illumination at each location during the middle epoch (indicated by yellow horizontal bar). a) Representative current-clamp trace from a BLA neuron expressing eNpHR 3.0 upon direct illumination shows potent inhibition of spiking during illumination of cell soma. b) Representative current-clamp trace from a BLA neuron expressing eNpHR 3.0 when a ~125 μm diameter light spot is presented ~300 μm away from the cell soma without illuminating an axon. c) Representative current-clamp trace from a BLA neuron expressing eNpHR 3.0 when a ~125 μm diameter light spot is presented ~300 μm away from the cell soma when illuminating an axon. d) While direct illumination of the cell soma induced complete inhibition of spiking that was significant from all other conditions ($F_{3,9}$=81.50, p<0.0001; n=3 or more per condition), there was no significant difference among the distal illumination ~300 μm away from the soma of BLA neurons expressing eNpHR 3.0 conditions and the no light condition ($F_{2,7}$=0.79, p=0.49), indicating that distal illumination did not significantly inhibit spiking at the cell soma. e) Schematic indicating light spot locations relative to recording site, regarding the population summary shown to the right. Population summary shows the normalized hyperpolarizing current recorded from the cell soma per distance of light spot from cell soma, both on and off axon collaterals (n=5).
Figure 16:
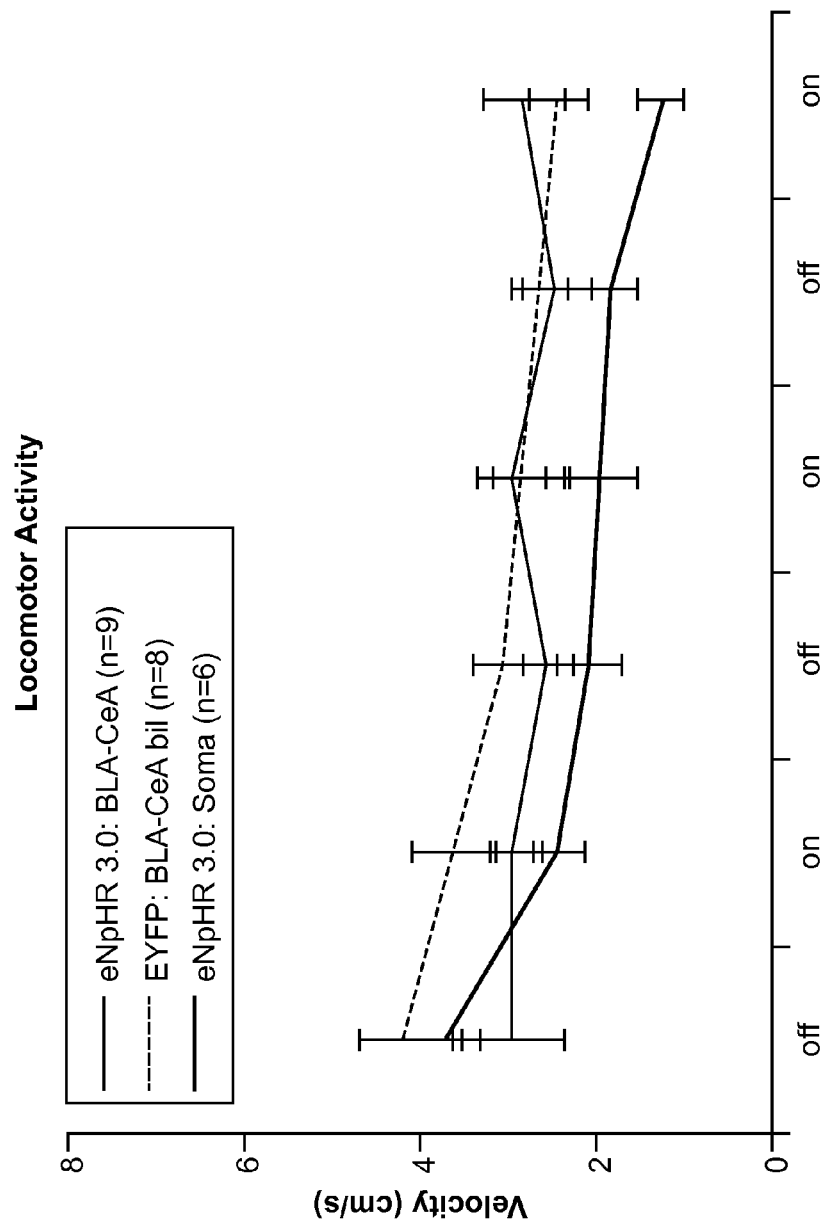
FIG. 16 is a graph demonstrating that light stimulation did not alter locomotor activity in eNpHR 3.0 and control groups. There were no detectable differences in locomotor activity among groups nor light epochs ($F_{1,20}$=0.023, p=0.3892; $F_{1,100}$=3.08, p=0.086).

In a final series of experiments, to determine if endogenous anxiety-reducing processes could be blocked by selectively inhibiting this pathway, we tested whether the selective inhibition of these optogenetically defined synapses could reversibly increase anxiety. We performed bilateral viral transduction of either eNpHR3.0, a light-activated chloride pump which hyperpolarizes neuronal membranes upon illumination with amber light[25], or EYFP alone, both under the CaMKIIα promoter in the BLA, and implanted bilateral beveled guide cannulae to allow selective illumination of BLA terminals in the CeA (FIG. 6a; FIG. 13). eNpHR3.0 expression was restricted to glutamatergic CaMKIIα-positive neurons in the BLA (FIG. 6b). The eNpHR3.0:BLA-CeA group only showed significantly elevated levels of c-fos expression, relative to the EYFP: BLA-CeA bil and eNpHR 3.0:Soma groups, in the CeM (p<0.05; FIG. 6c-e), consistent with the hypothesis that selective inhibition of BLA terminals in the CeA suppresses feed-forward inhibition from CeL neurons to CeM neurons, thus increasing CeM excitability and the downstream processes leading to increased anxiety phenotypes. Importantly, inhibition of BLA somata did not induce an anxiogenic response, likely due to the simultaneous decrease in direct BLA-CeM excitatory input. We also found that the eNpHR3.0:BLA-CeA group showed a significant reduction in open arm time and probability of open arm entry on the elevated plus maze during light-on epochs, but not light-off epochs, relative to the EYFP and Soma groups (FIG. 6f,g), without altering locomotor activity (FIG. 16). The eNpHR3.0:BLA-CeA group also showed a significant reduction in center time upon illumination with 594 nm light, relative to the EYFP and Soma groups (statistics, p=0.002; FIG. 6h,i) Finally, we also demonstrate that selective illumination of eNpHR3.0-expressing axon terminals can reduce the probability of both spontaneously occurring (FIG. 6j-l) and evoked (FIG. 6m-p) vesicle release, without preventing spiking at the cell soma (FIG. 14). These data demonstrate that selective inhibition of BLA terminals in the CeA induces an acute increase in anxiety-like behaviors.

CONCLUSIONS

In these experiments, we have identified the BLA-CeL pathway as an endogenous neural substrate for bidirectionally modulating the unconditioned expression of anxiety. While we identify the BLA-CeL pathway as the critical substrate rather than BLA fibers passing through the CeL, it is likely that other downstream circuits, such as CeA projections to the BNST play an important role in the expression of anxiety or anxiety-related behaviors[4, 6, 13]. Indeed, our findings may support the notion that corticotrophin releasing hormone (CRH) networks in the BNST can be critically involved in modulating anxiety-related behaviors[6, 52], as the CeL is a primary source of CRH for the BNST[53].

Other neurotransmitters and neuromodulators may modulate or gate effects on distributed neural circuits, including serotonin[54, 55], dopamine[56], acetylcholine[57], glycine[58], GABA[13] and CRH[59]. The neural circuitry converging to and diverging from this pathway will provide many opportunities for modulatory control, as parallel or downstream circuits of the BLA-CeL synapse likely contribute to modulate the expression of anxiety phenotypes[6, 56]. Moreover, upstream of the amygdala, this microcircuit is well-positioned to be recruited by top-down cortical control from regions important for processing fear and anxiety, including the prelimbic, infralimbic and insular cortices that provide robust innervation to the BLA and CeL.[4, 13, 23, 60]

Our examination of the BLA anatomy suggests that the populations of BLA neurons projecting to CeL and CeM neurons are largely non-overlapping. In natural states, the CeL-projecting BLA neurons may excite CeM-projecting BLA neurons in a microcircuit homeostatic mechanism. This may also represent a potential mechanism underlying anxiety disorders, when there are synaptic changes that skew the balance of the circuit to allow uninhibited CeM activation.

Together, the data presented here support identification of the BLA-CeL synapse as a critical circuit element both necessary and sufficient for the expression of endogenous anxiolysis in the mammalian brain, providing a novel source of insight into anxiety as well as a new kind of treatment target, and demonstrate the importance of resolving specific projections in the study of neural circuit function relevant to psychiatric disease.

Although the foregoing invention has been described in some detail by way of illustration and example for purposes of clarity of understanding, the descriptions and examples should not be construed as limiting the scope of the invention.

All references, publications, and patent applications disclosed herein are hereby incorporated by reference in their entirety.

REFERENCES

1. Lieb, R. Anxiety disorders: clinical presentation and epidemiology. *Handb Exp Pharmacol,* 405-432 (2005).
2. Kessler, R. C., et al. Lifetime prevalence and age-of-onset distributions of DSM-IV disorders in the National Comorbidity Survey Replication. Arch Gen Psychiatry 62, 593-602 (2005).
3. Koob, G. F. Brain stress systems in the amygdala and addiction. Brain Res 1293, 61-75 (2009).
4. Ressler, K. J. & Mayberg, H. S. Targeting abnormal neural circuits in mood and anxiety disorders: from the laboratory to the clinic. *Nat Neurosci* 10, 1116-1124 (2007).
5. Vanderschuren, L. J. & Everitt, B. J. Behavioral and neural mechanisms of compulsive drug seeking. Eur J Pharmacol 526, 77-88 (2005).
6. Davis, M., Walker, D. L., Miles, L. & Grillon, C. Phasic vs sustained fear in rats and humans: role of the extended amygdala in fear vs anxiety. Neuropsychopharmacology 35, 105-135.
7. Ehrlich, I., et al. Amygdala inhibitory circuits and the control of fear memory. Neuron 62, 757-771 (2009).
8. Han, J. H., et al. Selective erasure of a fear memory. *Science* 323, 1492-1496 (2009).
9. Herry, C., et al. Switching on and off fear by distinct neuronal circuits. Nature 454, 600-606 (2008).
10. LeDoux, J. The emotional brain, fear, and the amygdala. Cell Mol Neurobiol 23, 727-738 (2003).
11. Maren, S. & Quirk, G. J. Neuronal signaling of fear memory. Nat Rev Neurosci 5, 844-852 (2004).
12. Pare, D., Quirk, G. J. & Ledoux, J. E. New vistas on amygdala networks in conditioned fear. *J* Neurophysiol 92, 1-9 (2004).
13. Shin, L. M. & Liberzon, I. The neurocircuitry of fear, stress, and anxiety disorders. Neuropsychopharmacology 35, 169-191.
14. Davis, M. The role of the amygdala in conditioned and unconditioned fear and anxiety. in The Amygdala (ed. A. JP) p. 213-288 (Oxford University Press, Oxford, UK, 2000).
15. Killcross, S., Robbins, T. W. & Everitt, B. J. Different types of fear-conditioned behaviour mediated by separate nuclei within amygdala. Nature 388, 377-380 (1997).
16. Tye, K. M. & Janak, P. H. Amygdala neurons differentially encode motivation and reinforcement. *J* Neurosci 27, 3937-3945 (2007).
17. Tye, K. M., Stuber, G. D., de Ridder, B., Bonci, A. & Janak, P. H. Rapid strengthening of thalamo-amygdala synapses mediates cue-reward learning. Nature 453, 1253-1257 (2008).
18. Bahi, A., Mineur, Y. S. & Picciotto, M. R. Blockade of protein phosphatase 2B activity in the amygdala increases anxiety- and depression-like behaviors in mice. Biol Psychiatry 66, 1139-1146 (2009).
19. Davis, M. Are different parts of the extended amygdala involved in fear versus anxiety? *Biol* Psychiatry 44, 1239-1247 (1998).
20. Etkin, A., et al. Individual differences in trait anxiety predict the response of the basolateral amygdala to unconsciously processed fearful faces. Neuron 44, 1043-1055 (2004).
21. Kalin, N. H., Shelton, S. E. & Davidson, R. J. The role of the central nucleus of the amygdala in mediating fear and anxiety in the primate. J Neurosci 24, 5506-5515 (2004).
22. Roozendaal, B., McEwen, B. S. & Chattarji, S. Stress, memory and the amygdala. *Nat Rev* Neurosci (2009).
23. Stein, M. B., Simmons, A. N., Feinstein, J. S. & Paulus, M. P. Increased amygdala and insula activation during emotion processing in anxiety-prone subjects. Am J Psychiatry 164, 318-327 (2007).
24. Boyden, E. S., Zhang, F., Bamberg, E, Nagel, G. & Deisseroth, K. Millisecond-timescale, genetically targeted optical control of neural activity. Nat Neurosci 8, 1263-1268 (2005).
25. Gradinaru, V., at aL Molecular and cellular approaches for diversifying and extending optogenetics. Ce// 141, 154-165.
26. Nagel, G., at al. Channelrhodopsin-2, a directly light-gated cation-selective membrane channel Proc Nat/ Acad Sci USA 100, 13940-13945 (2003).
27. Fraser, A. D. Use and abuse of the benzodiazepines. Ther Drug Monit 20, 481-489 (1998).
28. Woods, J. H., Katz, J. L. & Winger, G. Benzodiazepines: use, abuse, and consequences. Pharmacol Rev 44, 151-347 (1992).
29. Hovatta, I. & Barlow, C. Molecular genetics of anxiety in mice and men. Anti Med 40, 92-109 (2008).
30. Hovatta, I., et al. Glyoxalase 1 and glutathione reductase 1 regulate anxiety in mice. *Nature* 438, 662-666 (2005).
31. Blanchard, R. J., Yudko, E. B., Rodgers, R. J. & Blanchard, D. C. Defense system psychopharmacology:

an ethological approach to the pharmacology of fear and anxiety. Behav Brain Res 58, 155-165 (1993).
32. LeDoux, J. E., Iwata, J., Cicchetti, P. & Reis, D. J. Different projections of the central amygdaloid nucleus mediate autonomic and behavioral correlates of conditioned fear. J Neurosci 8, 2517-2529 (1988).
33. Carlson, J. Immunocytochemical localization of glutamate decarboxylase in the rat basolateral amygdaloid nucleus, with special reference to GABAergic innervation of amygdalostriatal projection neurons. J Comp Neurol 273, 513-526 (1988).
34. Smith, Y. & Pare, D. Intra-amygdaloid projections of the lateral nucleus in the cat: PHA-L anterograde labeling combined with postembedding GABA and glutamate immunocytochemistry. *J Comp Neurol* 342, 232-248 (1994).
35. McDonald, A. J. Cytoarchitecture of the central amygdaloid nucleus of the rat. *J Comp Neurol* 208, 401-418 (1982).
36. Bissiere, S., Humeau, Y. & Luthi, A. Dopamine gates LTP induction in lateral amygdala by suppressing feedforward inhibition. Nat Neurosci 6, 587-592 (2003).
37. Marowsky, A., Yanagawa, Y., Obata, K. & Vogt, K. E. A specialized subclass of interneurons mediates dopaminergic facilitation of amygdala function. Neuron 48, 1025-1037 (2005).
38. Pitkanen, A. Connectivity of the rat amygdaloid complex. in *The Amygdala* (ed. A. JP) p. 31-99 (Oxford University Press, Oxford, UK, 2000).
39. Krettek, J. E. & Price, J. L. Amygdaloid projections to subcortical structures within the basal forebrain and brainstem in the rat and cat. J Comp Neurol 178, 225-254 (1978).
40. Petrovich, G. D. & Swanson, L. W. Projections from the lateral part of the central amygdalar nucleus to the postulated fear conditioning circuit. Brain Res 763, 247-254 (1997).
41. LeDoux, J. E., Cicchetti, P., Xagoraris, A. & Romanski, L. M. The lateral amygdaloid nucleus: sensory interface of the amygdala in fear conditioning. J Neurosci 10, 1062-1069 (1990).
42. Krettek, J. E. & Price, J. L. A description of the amygdaloid complex in the rat and cat with observations on intra-amygdaloid axonal connections. J Comp Neurol 178, 255-280 (1978).
43. Petrovich, G. D., Risold, P. Y. & Swanson, L. W. Organization of projections from the basomedial nucleus of the amygdala: a PHAL study in the rat. J Comp Neural 374, 387-420 (1996).
44. Pare, D. & Smith, Y. The intercalated cell masses project to the central and medial nuclei of the amygdala in cats. Neuroscience 57, 1077-1090 (1993).
45. Likhtik, E., Popa, D., Apergis-Schoute, J., Fidacaro, G. A. & Pare, D. Amygdala intercalated neurons are required for expression of fear extinction. Nature 454, 642-645 (2008).
46. Jolkkonen, E. & Pitkanen, A. Intrinsic connections of the rat amygdaloid complex: projections originating in the central nucleus. J Comp Neurol 395, 53-72 (1998).
47. Amano, T., Unal, C. T. & Pare, D. Synaptic correlates of fear extinction in the amygdala. *Nat* Neurosci 13, 489-494.
48. McDonald, A. J., Muller, J. F. & Mascagni, F. GABAergic innervation of alpha type II calcium/calmodulin-dependent protein kinase immunoreactive pyramidal neurons in the rat basolateral amygdala. J Comp Neurol 446, 199-218 (2002).
49. Choleris, E., Thomas, A. W., Kavaliers, M. & Prato, F. S. A detailed ethological analysis of the mouse open field test: effects of diazepam, chlordiazepoxide and an extremely low frequency pulsed magnetic field. Neurosci Biobehav Rev 25, 235-260 (2001).
50. Pellow, S., Chopin, P., File, S. E. & Briley, M. Validation of open:closed arm entries in an elevated plus-maze as a measure of anxiety in the rat. J Neurosci Methods 14, 149-167 (1985).
51. Sah, P. & Lopez De Armentia, M. Excitatory synaptic transmission in the lateral and central amygdala. Ann N Y Acad Sci 985, 67-77 (2003).
52. Davis, M. & Shi, C. The extended amygdala: are the central nucleus of the amygdala and the bed nucleus of the stria terminalis differentially involved in fear versus anxiety? Ann N Y Acad Sci 877, 281291 (1999).
53. Sakanaka, M., Shibasaki, T. & Lederis, K. Distribution and efferent projections of corticotropin-releasing factor-like immunoreactivity in the rat amygdaloid complex. Brain Res 382, 213-238 (1986).
54. Holmes, A., Yang, R. J., Lesch, K. P., Crawley, J. N. & Murphy, D. L. Mice lacking the serotonin transporter exhibit 5-HT(1A) receptor-mediated abnormalities in tests for anxiety-like behavior. *Neuropsychopharmacology* 28, 2077-2088 (2003).
55. Lesch, K. P., et al. Association of anxiety-related traits with a polymorphism in the serotonin transporter gene regulatory region. Science 274, 1527-1531 (1996).
56. Graybiel, A. M. & Rauch, S. L. Toward a neurobiology of obsessive-compulsive disorder. *Neuron* 28, 343-347 (2000).
57. Picciotto, M. R., Brunzell, D. H. & Caldarone, B. J. Effect of nicotine and nicotinic receptors on anxiety and depression. Neuroreport 13, 1097-1106 (2002).
58. Snyder, S. H. & Enna, S. J. The role of central glycine receptors in the pharmacologic actions of benzodiazepines. Adv Biochem Psychopharmacol, 81-91 (1975).
59. Lesscher, H. M., et al. Amygdala protein kinase C epsilon regulates corticotropin-releasing factor and anxiety-like behavior. Genes Brain Behav 7, 323-333 (2008).
60. Milad, M. R., Rauch, S. L., Pitman, R. K. & Quirk, G. J. Fear extinction in rats: implications for human brain imaging and anxiety disorders. Biol Psycho! 73, 61-71 (2006).

What is claimed is:

1. A system comprising:
   a) a non-human animal comprising a light-responsive opsin expressed in glutamatergic pyramidal neurons of the basolateral amygdala (BLA), wherein the opsin is an opsin which induces hyperpolarization of a neuron in response to light, and wherein the selective illumination of the opsin in the BLA-CeL induces anxiety of the animal;
   b) a beveled guide cannula configured to be placed over the CeL to prevent light delivery to the BLA and to allow selective illumination of the CeA; and
   c) a light source.

2. The system of claim 1, comprising a device configured to take electrophysiological recordings.

3. The system of claim 1, wherein the light source comprises an optical fiber.

4. The system of claim 1, further including a means for delivering one or more of a pharmacological agent, an electrical stimulus, or a magnetic stimulus to the non-human animal.

5. The system of claim 1, wherein the opsin comprises an amino acid sequence having at least 90% amino acid sequence identity to one of SEQ ID NOs:1-4.

6. The system of claim 1, wherein the opsin comprises an amino acid sequence having at least 95% amino acid sequence identity to one of SEQ ID NOs:1-4.

7. The system of claim 1, wherein the opsin comprises an endoplasmic reticulum (ER) export signal.

8. The system of claim 7, wherein the ER export signal comprises the amino acid sequence FXYENE (SEQ ID NO:12).

9. The system of claim 1, wherein the opsin comprises a membrane trafficking signal.

10. The system of claim 9, wherein the membrane trafficking signal comprises the amino acid sequence KSRITSEGEYIPLDQIDINV (SEQ ID NO:14).

11. The system of claim 1, wherein the opsin comprises an ER export signal and a membrane trafficking signal.

12. The system of claim 1, wherein the opsin is encoded by a nucleotide sequence that is operably linked to a CaMKIIα promoter.

* * * * *